(12) United States Patent
Fraser et al.

(10) Patent No.: US 8,088,733 B2
(45) Date of Patent: *Jan. 3, 2012

(54) METHODS OF USING MACROCYCLIC AGONISTS OF THE GHRELIN RECEPTOR FOR TREATMENT OF GASTROINTESTINAL MOTILITY DISORDERS

(75) Inventors: Graeme L. Fraser, Rixensart (BE); Hamid R. Hoveyda, Québec (CA); Mark L. Peterson, Sherbrooke (CA)

(73) Assignee: Tranzyme Pharma Inc. (CA)

( * ) Notice: Subject to any disclaimer, the term of this patent is extended or adjusted under 35 U.S.C. 154(b) by 994 days.

This patent is subject to a terminal disclaimer.

(21) Appl. No.: 11/774,185

(22) Filed: Jul. 6, 2007

(65) Prior Publication Data

US 2008/0051383 A1   Feb. 28, 2008

Related U.S. Application Data

(60) Provisional application No. 60/818,915, filed on Jul. 6, 2006.

(51) Int. Cl.
*A61K 38/12* (2006.01)
*C07K 5/12* (2006.01)
(52) U.S. Cl. .................................. 514/9.7; 530/317
(58) Field of Classification Search .................. None
See application file for complete search history.

(56) References Cited

U.S. PATENT DOCUMENTS

| | | | |
|---|---|---|---|
| 3,997,540 A | 12/1976 | Mehta et al. | |
| 4,801,604 A * | 1/1989 | Vonvoigtlander et al. | 514/429 |
| 6,011,155 A | 1/2000 | Villhauer | |
| 6,165,985 A | 12/2000 | Jasserand et al. | |
| 6,479,460 B1 | 11/2002 | Bab et al. | |
| 6,548,501 B2 | 4/2003 | Hakkinen | |
| 6,586,403 B1 | 7/2003 | Mathison et al. | |
| 6,653,334 B1 | 11/2003 | Yamazaki et al. | |
| 6,852,722 B2 | 2/2005 | Hakkinen | |
| 7,056,942 B2 * | 6/2006 | Hildesheim et al. | 514/411 |
| 7,109,226 B2 | 9/2006 | Yamazaki et al. | |
| 7,452,862 B2 | 11/2008 | Deslongchamps et al. | |
| 7,476,653 B2 | 1/2009 | Hoveyda et al. | |
| 7,491,695 B2 | 2/2009 | Fraser et al. | |
| 2005/0049234 A1 | 3/2005 | Deslongchamps et al. | |
| 2005/0054562 A1 | 3/2005 | Fraser et al. | |
| 2005/0119169 A1 | 6/2005 | Deslongchamps et al. | |
| 2008/0194672 A1* | 8/2008 | Hoveyda et al. | 514/450 |
| 2008/0281075 A1* | 11/2008 | Harwood et al. | 530/317 |
| 2010/0087381 A1 | 4/2010 | Polvino | |

FOREIGN PATENT DOCUMENTS

| | | |
|---|---|---|
| DE | 2235377 | 2/1973 |
| EP | 1159964 A2 | 12/2001 |
| GB | 1365201 | 8/1974 |
| WO | WO 96/22304 A1 | 7/1996 |
| WO | WO 97/48713 A1 | 12/1997 |
| WO | WO 98/46631 A1 | 10/1998 |
| WO | WO 98/54577 A1 | 12/1998 |
| WO | WO 01/25257 A2 | 4/2001 |
| WO | WO 01/92292 A2 | 12/2001 |
| WO | WO 02/08250 A2 | 1/2002 |
| WO | WO 2004/111077 | * 12/2004 |
| WO | WO 2004/111077 A1 | 12/2004 |
| WO | WO 2005/012331 A1 | 2/2005 |
| WO | WO 2005/012332 A1 | 2/2005 |
| WO | WO 2008/130464 | * 10/2008 |

OTHER PUBLICATIONS

Vippagunta et al ('Crystalline solids' Adv. Drug Delivery Rev. v48 2001 pp. 3-26).*
U.S. Appl. No. 12/631,490, Polvino, Dec. 4, 2009.
U.S. Appl. No. 12/333,026, filed Dec. 11, 2008, Fraser et al.
U.S. Appl. No. 12/263,179, filed Oct. 31, 2008, Marsault et al.
U.S. Appl. No. 12/351,395, filed Jan. 9, 2009, Marsault et al.
U.S. Appl. No. 12/197,610, filed Aug. 25, 2008, Deslongchamps et al.
Abell et al. "Treatment of gastroparesis: a multidisciplinary clinical review", *Neurogastrenterol. Motil.* 18:263-283 (2006).
Ahnfelt-Ronne et al. "Do Growth Hormone-Releasing Peptides Act as Ghrelin Secretagogues?" *Endocrine* 14(1): 133-135 (2001).
Arcadi et al. "Electrophilic Cyclization of o-Acetoxy- and o-Benzyloxyalkynylpyridines: An Easy Entry into 2, 3-Disubsituted Furopyridines" *Organic Letters* 4(14): 2409-2412 (2002).
Ariyasu et al. "Stomach is a Major Source of Circulating Ghrelin, and Feeding State Determines Plasma Ghrelin-Like Immunoreactivity Levels in Humans" *The Journal of Clinical Endocrinology & Metabolism* 86(10);: 4753-4758 (2001).
Arvat et al. "Growth Hormone-Releasing Hormone and Growth Hormone Secretagogue-Receptor Ligands" *Endocrine* 14(1): 35-43 (2001).
Arvat et al. "Ghrelin and synthetic GH secretagogues", *Best Practice and Research Clinical Endocrinology and Metabolism* 16(3):505-517 (2002). Backes et al. "Solid Support Linker Strategies" *Current Opinion in Chemical Biology* 1: 86-93 (1997).
Baig et al. "Postoperative Ileus: A Review" *Diseases of the Colon & Rectum* 47: 516-526 (2004).
Baldanzi et al. "Ghrelin and des-acyl Ghrelin Inhibit Cell Death in Cardiomyocytes and Endothelial Cells through ERK1/2 and Pl 3-kinase/AKT" *The Journal of Cell Biology* 159(6): 1029-1037 (2002).
Baldwin et al. "Symbiotic Approach to Drug Design: Antihypertensive β-Adrenergic Blocking Agents" *Journal of Medicinal Chemistry* 22(11): 1284-1290 (1979).
Banks et al. "Extent and Direction of Ghrelin Transport Across the Blood-Brain Barrier Is Determined by its Unique Primary Structure" *The Journal of Pharmacology and Experimental Therapeutics* 302: 822-827 (2002).
Bar-Natan et al. "Delayed gastric emptying after gastric surgery", *Am. J. Surq.* 172:24-28 (1996).

(Continued)

*Primary Examiner* — Cecilia J Tsang
*Assistant Examiner* — Ronald Niebauer
(74) *Attorney, Agent, or Firm* — Myers Bigel Sibley & Sajovec, PA

(57) ABSTRACT

The present invention provides novel conformationally-defined macrocyclic compounds that have been demonstrated to be selective agonists of the ghrelin receptor (growth hormone secretagogue receptor, GHS-R1a and subtypes, isoforms and variants thereof). Such compounds are useful as medicaments for treatment and prevention of a range of medical conditions characterized by disturbed gastrointestinal motility including, but not limited to, post-surgical gastroparesis and post-operative ileus in combination with opioid-induced bowel dysfunction. These agents are effective for multiple disorders at dose levels equivalent to those required to treat a single disorder.

16 Claims, 9 Drawing Sheets

OTHER PUBLICATIONS

Barreiro et al. "Developmental, Stage-Specific, and Hormonally Regulated Expression of Growth Hormone Secretagogue Receptor Messenger RNA in Rat Testis" *Biology of Reproduction* 68: 1631-1640 (2003).

Barth et al. "Tailoring Ultraresins Based on the Cross-Linking of Polyethylene Imines. Comparative Investigation of the Chemical Composition, the Swelling, the Mobility, the Chemical Accessibility, and the Performance in Solid-Phase Synthesis of Very High Loaded Resins" *Journal of Combinatorial Chemistry* 6: 340-349 (2004).

Bassil et al. "Prokineticin-2, motilin, ghrelin and metoclopramide: prokinetic utility in mouse stomach and colon", *Eur. J. Pharmacol.* 524:138-144 (2005).

Bedendi et al. "Cardiac Effects of Ghrelin and its Endogenous derivatives des-octanoyl Ghrelin and des-Gln$^{14}$-ghrelin" *European Journal of Pharmacology* 476: 87-95 (2003).

Bednarek et al. "Structure-Function Studies on the New Growth Hormone-Releasing Peptide, Ghrelin: Minimal Sequence of Ghrelin Necessary for Activation of Growth Hormone Secretagogue Receptor 1 a" *Journal of Medicinal Chemistry* 43: 4370-4376 (2000).

Binn et al. "Ghrelin gastrokinetic action in patients with neurogenic gastroparesis", *Peptides* 27:1603-1606 (2006).

Birr et al. "Der •,•-Dimethyl-3.5-dimethoxybenzyloxycarbonyl (Ddz)-Rest, eine photo- und säurelabile Stickstoff-Schutzgruppe für die Peptidehemie" *Liebigs Ann Chem* 763: 162-172 (1972).

Boger et al. "Total Synthesis of HUN-7293", *J. Am. Chem. Soc.* 121:6197-6205 (1999).

Bossharth et al. "Palladium-Mediated Three-Component Sythesis of Furo[2,3-*b*]pyridones by One= Pot Coupling of 3-lodopyridones, Alkynes, and Organic Halides" *Organic Letters* 5(14): 2441-2444 (2003).

Bowers "Growth Hormone Releasing Peptides: Physiology and Clinical Applications" *Current Opinion in Endocrinology & Diabetes* 7: 168-174 (2000).

Bowers et al. "Structure-Activity Relationships of a Synthetic Pentapeptide that Specifically Releases Growth Hormone in Vitro" *Endocrinology* 106(3): 663-667 (1980).

Broglio et al. "Endocrine and Non-Edocrine Actions of Ghrelin" *Hormone Research* 59: 109-117 (2003).

Burgess "Solid-Phase Syntheses of β-Turn Analogues to Mimic or Disrupt Protein-Protein Interactions", *Acc. Chem. Res.* 34:826-835 (2001).

Camanni et al. "Growth Hormone-Releasing Peptides and Their Analogs" *Frontiers in Neuroendocrinology* 19: 47-72 (1998).

Camilleri "Advances in Diabetic Gastroparesis" *Reviews in Gastroenterological Disorders* 2(2): 47-56 (2002).

Camilleri "Diabetic gastroparesis", *New Eng. J. Med.* 356:820-829 (2007).

Cao et al. "Effects of ghrelin and synthetic GH secretagogues on the cardiovascular system", *Trends in Endocrinology and Metabolism* 17(1):14-18 (2006).

Carlini et al. "Ghrelin Increases Anxiety-Like Behavior and Memory Retention in Rats" *Biochemical and Biophysical Research Communications* 299: 739-743 (2002).

Carpino et al. "Recent Developments in Ghrelin Receptor (GHS-R1a) Agonists and Antagonists" *Expert Opinion in Ther. Patents* 12(11): 1599-1618 (2002).

Carreira et al. "Agonist-Specific Coupling of Growth Hormone Secretagogue Receptor Type 1a to Different Intracellular Signaling Systems" *Neuroendocrinology* 79: 13-25 (2004).

Casanueva et al. "Ghrelin: The Link Connecting Growth with Metabolism and Energy Homeostatis" *Reviews in Endocrine & Metabolic Disorders* 3: 325-338 (2002).

Cassoni et al. "Expression of Ghrelin and Biological Activity of Specific Receptors for Ghrelin and des-acyl Ghrelin in Human Prostate Neoplasms and Related Cell Lines" *European Journal of Endocrinology* 150: 173-184 (2004).

Chan et al. "Identification and Functional Characterization of Two Alternatively Spliced Growth Hormone Secretagogue Receptor Transcripts from the Pituitary of Black Seabream *Acanthopagrus schlegeli*" *Molecular and Cellular Endocrinology* 241: 81-95 (2004).

Chang et al. "A Highly Efficient and practical Synthesis of Chromene Derivatives Using Ring-Closing Olefin Metathesis" *Journal of Organic Chemistry* 63: 864-866 (1998).

Chang et al. "Activity of a Novel Nonpeptidyl Growth Hormone Secretagogue, L-700, 653, in Swine" *Endocrinology* 136(3): 1065-1071 (1995).

Chen et al. "Des-acyl ghrelin acts by CRF type 2 receptors to disrupt fasted stomach motility in conscious rats", *Gastroenterology* 129: 8-25 (2005).

Chen et al. "Intracisternal des-acyl ghrelin inhibits food intake and non-nutrient gastric emptying In conscious rats", *Int. J. Mol. Med.* 16:695-699 (2005).

Cheng et al. "The Synergistic Effects of His-D-Trp-Ala-Trp-D-Phe-Lys-NH$_2$ on Growth Hormone (GH)-Releasing Factor-Stimulated GH Release and Intracellular Adenosine 3', 5'-Monophosphate Accumulation in Rat Primary Pituitary Cell Culture" *Endocrinology* 124(6): 2791-2798 (1989).

Cohen et al. "Delayed gastric emptying following gastrectomy", *Ann. Surg.* 184:689-696 (1976).

Comins et al. "*N*- vs. *O*- Alkylation in the Mitsunobu Reaction of 2-Pyridone" *Tetrahedron Letters* 35(18): 2819-2822 (1994).

Crowley et al. "Obesity therapy: altering the energy intake-and-expenditure balance sheet. Nat. Rev. Drug Disc", 1:276-286 (2002).

Cummings et al. "Plasma Ghrelin Levels After Diet-Induced Weight Loss or Gastric Bypass Surgery" *New England Journal of Medicine* 346(21): 1623-1630 (2002).

Cunha et al. "Ghrelin and Growth Hormone (GH) Secretagogues Potentiate GH-Releasing Hormone (GHRH)-Induced Cyclic Adenosine 3', 3'-Monophosphate Production in Cells Expressing Transfected GHRH and GH Secretagogue Receptors" *Endocrinology* 143(12): 4570-4582 (2002).

Davenport et al. "International Union of Pharmacology. LVI. Ghrelin Receptor Nomenclature, Distribution, and Function", *Pharmacol. Rev.*, 57:541-546 (2005).

Davies "The Cyclization of Peptides and Depsipeptides", *J. Peptide Sci.* 9:471-501 (2003).

Deghenghi et al. "GH-Releasing Activity of Hexarelin, A New Growth Hormone Releasing Peptide, in Infant and Adult Rats" *Life Sciences* 54(18): 1324-1328 (1994).

Deghenghi et al. "Somatostatin Octapeptides (Lanreotide, Octreotide, Vapreotide, and their Analogs) Share the Growth Hormone-Releasing Peptide Receptor in the Human Pituitary Gland" *Endocrine* 14(1): 29-33 (2001).

Deghenghi et al. "Targeting the Ghrelin Receptor" *Endocrine* 22(1): 13-18 (2003).

Depoortere et al. "Interaction of the Growth Hormone-Releasing Peptides Ghrelin and Growth Hormone-Releasing Peptide-6 with the Motilin Receptor in the Rabbit Gastric Antrum" *The Journal of Pharmacology and Experimental Therapeutics* 305: 660-667 (2003).

Depoortere et al. "Comparison of the gastroprokinetic effects of ghrelin, GHRP-6 and motilin in rats in vivo and in vitro", *Eur. J. Pharmacol.*, 515:160-168 (2005).

Devi "Heterodimerization of G-Protein-Coupled Receptors: Pharmacology, Signaling and Trafficking" *Trends in Pharmacological Sciences* 22(10): 532-537 (2001).

DeWinter et al. "Effect of ghrelin and growth hormone-releasing peptide 6 on septic ileus in mice", *Neurogastroenterol. Motil.* 16:439-446 (2004).

Diano et al. "Ghrelin controls hippocampal spine synapse density and memory performance", *Nat. Neuroscience*, 9:381-388 (2006).

Doberneck et al. "Delayed gastric emptying after palliative gastrojejunostomy for carcinoma of the pancreas", *Arch. Surg.*, 122:827-829 (1987).

Eckhauser et al. "Safety and Long-Term Durability of Completion Gastrectomy in 81 Patients with Postsurgical Gastroparesis Syndrome", *Am. Surg.* 1998, 64(8):711-717 (1998).

Edholm et al. "Ghrelin Stimulates Motility in the Small Intestine of Rats Through Intrinsic Cholinergic Neurons" *Regulatory Peptides* 121: 25-30 (2004).

Eggenweiler "Linkers for Solid-Phase Synthesis of Small Molecules: Coupling and Cleavage Techniques" *Drug Disc. Today* 3(12): 552-560 (1998).

Eguchi et al. "Design, Synthesis, and Application of Peptide Secondary Structure Mimetics", *Mini Reviews in Medicinal Chem.* 2:447-462 (2002).

Elias et al. "In Vitro Characterization of Four Novel Classes of Growth Hormone-Releasing Peptide" *Endocrinology* 136(12): 5694-5699 (1995).

European Search Report corresponding to European Application No. 04761605 dated Jul. 7, 2006.

Examination Report corresponding to European Application No. 04761605.7-1216 mailed Mar. 12, 2008.

Fehrentz et al. "Growth Hormone Secretagogues: Past, Present and Future" *IDrugs* 5(8): 804-814 (2002).

Feighner et al. "Receptor for Motilin Identified in the Human Gastrointestinal System" *Science* 284: 2184-2188 (1999).

Fraser et al. "Effect of the ghrelin receptor agonist TZP-101 on colonic transit in a rat model of postoperative ileus", *Eur. J. Pharmacol.* 604:132-137 (2009).

Fraser et al. "Pharmacological Demarcation of the Growth Hormone, Gut Motility and Feeding Effects of Ghrelin Using a Novel Ghrelin Receptor Agonist", *Endocrinology* 149:6280-6288 (2008).

Frechet et al. "Use of Polymers as Protecting Groups in Organic Synthesis. II. Protection of Primary Alcohol Functional Groups" *Tetrahedron Letters* 35: 3055-3056 (1975).

Fujino et al. "Ghrelin Induces Fasted Motor Activity of the Gastrointestinal Tract in Conscious Fed Rats" *Journal of Physiology* 550(1): 227-240 (2003).

Fukuda et al. "Ghrelin enhances gastric motility through direct stimulation of intrinsic neural pathways and capsaicin-sensitive afferent •eurons in rats", *Scand. J. Gastroenterol.*, 39:1209-1214 (2004).

Ghigo et al. "Orally Active Growth Hormone Secretagogues: State of the Art and Clinical Perspectives" *Ann. Med.* 30:159-168 (1998).

Glenn et al. "Mimetics of Peptide β-Strand", *Mini Reviews in Medicinal Chem.* 2:433-445 (2002).

Granado et al. "Anti-inflammatory effect of the ghrelin agonist growth hormone-releasing peptide-2 (GHRP-2) in arthritic rats", *Am. J. Physiol. Endocrinol. Metab.*, 288:E486-E492 (2005).

Gross "A Concise Stereospecific Synthesis of Repinotan (BAYx3702)" *Tetrahedron Letters* 44: 8563-8565 (2003).

Halem et al. "Novel Analogs of Ghrelin: Physiological and Clinical Implications" *European Journal of Endocrinology* 151: S71-S75 (2004).

Halem et al. "A novel growth hormone secretagogue-1a receptor antagonist that blocks ghrelin-induced growth hormone secretion but induces increased body weight gain", *Neuroendocrinol.*, 81:339-349 (2005).

Hansen et al. "Functional consequences of 7TM receptor dimerization", *Eur. J. Pharm. Sci.*, 23:301-317 (2004).

Hansen, Jr. et al. "Chemoselective N-Ethylation of Boc Amino Acids without Racemization" *Journal of Organic Chemistry* 50: 945-950 (1985).

Haramura et al. "Design and Synthesis of N-terminal Cyclic Motilin Partial Peptides: A Novel Pure Motilin Antagonist", *Chem. Pharm. Bull.* 49(1):40-43 (2001).

Haramura et al. "Design and Synthesis of Motilin Antagonists Derived from the [1-4] Fragment of Porcine Motilin", *J. Med. Chem.* 45:670-675 (2002).

Harrity et al. "Chromenes through Metal-Catalyzed Reactions of Styrenyl Ethers. Mechanism and Utility in Synthesis" *Journal of the American Chemical Society* 120: 2343-2351 (1998).

Heidenreich et al. "Gastroparesis After Retroperitoneal Surgery Successfully Treated With Erythromycin" *J. Urology* 163:545 (2000).

Hickey et al. "Efficacy and Specificity of L-692, 429, A Novel Nonpeptidyl Growth Hormone Secretagogue, in Beagles" *Endocrinology* 134(2): 695-701 (1994).

Hickey et al. "Repeat Administration of the GH Secretagogue MK-0677 Increases and Maintains Elevated IGF-I Levels in Beagles" *Journal of Endocrinology* 152: 182-192 (1997).

Hirano et al. "Chronic Intestinal Pseudo-Obstruction" *Digestive Diseases* 18: 83-92 (2000).

Hofslokken et al. "Convenient Method for the *ortho*-Formylation of Phenols" *Acta Chemica Scandinavica* 53: 258-262 (1999).

Hojo et al. "Polypeptide Synthesis Using the S-Alkyl Thioester of a Partially Protected Peptide Segment. Synthesis of the DNA-Binding Domain of *c*-Myb Protein (142-193)-NH$_2$" *Bulletin of the Chemical Society of Japan* 64: 111-117 (1991).

Holst et al. "Ghrelin receptor mutations—too little height and too much hunger", *J. Clin. Invest.*, 116:637-641 (2006).

Holst et al. "Constitutive ghrelin receptor activity as a signaling set-point in appetite regulation", *Trends Pharmacol. Sci.*, 25:113-117 (2004).

Holst et al. "Common structural basis for constitutive activity of the ghrelin receptor family", *J. Biol. Chem.*, 279:53806-53817 (2004).

Holst et al. "High constitutive signaling of the ghrelin receptor—identification of a potent inverse agonist", *Mol. Endocrinol.*, 17:2201-221 (2003).

Horton et al. "Exploring privileged structures: The combinatorial synthesis of cyclic peptides", *Molecular Diversity* 5:289-304 (2002).

Horvath et al. "Ghrelin as a potential anti-obesity target", *Curr. Pharm. Design*, 9:1383-1395 (2003).

Horvath et al. "Minireview: Ghrelin and the regulation of Energy Balance—A Hypothalamic Perspective" *Endocrinology* 142(10): 4163-4169 (2001).

Hosoda et al. "Purification and Characterization of Rat des-Gln$^{14}$-Ghrelin, a Second Endogenous Ligand for the Growth Hormone Secretagogue Receptor" *The Journal of Biological Chemistry* 275(29): 21995-22000 (2000).

Hosoda et al. "Structural Divergence of Human Ghrelin" *The Journal of Biological Chemistry* 278(1): 64-70 (2003).

Hosoda et al. "Biological, physiological, and pharmacological aspects of ghrelin", *J. Pharmacol. Sci.*, 100:398-410 (2006).

Howard et al. "A Receptor in Pituitary and Hypothalamus that Functions in Growth Hormone Relase" *Science* 273: 974-977 (1996).

International Search Report and the Written Opinion of the International Searching Authority for International application PCT/US2005/020654 mailed on Dec. 16, 2005.

International Search Report and the Written Opinion of the International Searching Authority for International application PCT/US2005/020857 mailed on Dec. 15, 2005.

Inui et al. "Ghrelin, appetite, and gastric motility: the emerging role of the stomach as an endocrine organ", *FASEB J.*, 18:439-456 (2004).

Iseri et al. "Ghrelin against alendronate-induced gastric damage in rats", *J. Endocrinol.*, 187:399-406 (2005).

Isgaard et al. "Ghrelin and GHS on cardiovascular applications/functions", *J. Endocrinol. Invest.*, 28:838-842 (2005).

Isidro et al. "Growth hormone secretagogues", *Comb. Chem. High Throughput Screen.*, 9:175-180 (2006).

Isobe et al. "Delayed gastric emptying in patients with liver cirrhosis", *Dig. Dis. Sci.*, 39:983-987 (1994).

Iwaki et al. "Novel Synthetic Strategy of Carbolines Via Palladium-Catalyzed Amination and Arylation Reaction" *J Chem Soc, Perkin Trans 1*: 1505-1510 (1999).

Jacks et al. "Effects of Acute and Repeated Intravenous Administration of L-692,585, A Novel Non-Peptidyl Growth Hormone Secretagogue, on Plasma Growth Hormone, IGF-1, ACTH, Cortisol, Prolactin, Insulin, and Thyroxine Levels in Beagles" *Journal of Endocrinology* 143: 399-406 (1994).

James "Linkers for Solid Phase Organic Synthesis" *Tetrahedron* 55: 4855-4946 (1999).

Kalff et al. "Surgical Manipulation of the Gut Elicits and Intestinal Muscularis Inflammatory Response Resulting in Postsurgical Ileus" *Annals of Surgery* 228(5): 652-663 (1998).

Khiat et al. "Identification of the motilide pharmacophores using quantitative structure activity relationships", *J. of Peptide Research* 52(4):321-328 (1998).

Kim et al. "A Merger of Rational Drug Design and Combinatorial Chemistry: Development and Application of Peptide Secondary Structure Mimetics", *Combinatorial Chem. & High Throughput Screening* 3:167-183 (2000).

Kitazawa et al. "Gastric motor effects of peptide and non-peptide ghrelin agonists in mice in vivo and in vitro", *Gut*, 54:1078-1084 (2005).

Knapp et al. "Synthesis of Hypusine and Other Polyamines Using Dibenzyltriazones for Amino Protection", *J. Org. Chem.* 57:6239-6256 (1992).

Koga et al. "Macrolide-Type Motilin Receptor Agonists: Assessment of the Biological Value of the 2'—and 4"—Hydroxyl Groups of Acid-Stable 8,9-Anhydroerythromycin A 6,9-Hemiacetals", *Bioorganic & Medicinal Chem. Letters* 4(13):1649-1654 (1994).

Kogan et al. "A Regio—and Stereocontrolled Total Synthesis of (-)-Indolactam-V", *Tetrahedron* 46(19):6623-6632 (1990).

Kojima et al. "Ghrelin is a Growth-Hormone-Releasing Acylated Peptide from Stomach" *Nature* 402: 656-660 (1999).

Kojima et al. "Ghrelin, an Orexigenic Signaling Molecule from the Gastrointestinal Tract" *Curent Opinion in Pharmacology* 2: 665-668 (2002).

Kojima et al. "Purification and Distribution of Ghrelin: The Natural Endogenous Ligand for the Growth Hormone Secretagogue Receptor" *Hormone Research* 56(supp 1): 93-97 (2001).

Krsek et al. "Plasma Ghrelin Levels in Patients with Short Bowel Syndrome" *Endocrine Research* 28(1&2): 27-33 (2002).

Kurz et al. "Opioid-Induced Bowel Dysfunction: Pathophysiology and Potential new Therapies" *Drugs* 63(7): 649-671 (2003).

Lambert et al. "The synthesis of cyclic peptides", *J. Chem. Soc., Perkin Trans.* 1 471-484 (2001).

Lasseter et al. "Ghrelin Agonist (TZP-101): Safety, Pharmacokinetics and Pharmacodynamic Evaluation in Healthy Volunteers: A Phase I, First-in-Human Study", *J. Clin. Pharmacol.* 48:193-202 (2008).

LePoul et al. "Adaptation of Aequorin Functional Assay to High Throughput Screening" *Journal of Biomolecular Screening* 7(1): 57-65 (2002).

Levin et al. "Effect of peripherally administered ghrelin on gastric emptying and acid secretion in the rat", *Regul. Pept.*, 131:59-65 (2005).

Li et al. "Current Synthetic Approaches to Peptide and Peptidomimetic Cyclization", *Current Organic Chem.* 6:411-440 (2002).

Lindstrom et al. "Sythesis of Two Conformationally Constrained Analogues of the Minor Tobacco Alkaloid Anabasine" *Organic Letters* 2(15): 2291-2293 (2000).

Liu et al. "Selective *N*-Functionalization of 6-Substituted-2-Pyridones" *Tetrahedron Letters* 36(49): 8917-8920 (1995).

Locatelli et al. "Growth Hormone Secretagogues: Focus on the Growth Hormone-Releasing Peptides" *Pharmacological Research* 36(6): 415-423 (1997).

Locatelli et al. "Ghrelin in gastroenteric pathophysiology", *J. Endocrinol. Invest.*, 28: 843-848(2005).

Luckey et al. "Mechanisms and Treatment of Postoperative Ileus" *Archives of Surgery* 1 38: 206-214 (2003).

Maarseveen et al. "Solid Phase Synthesis of Heterocycles by Cyclization/Cleavage Methodologies" *Combinatorial Chemistry & High Throughput Screening* 1: 185-214 (1998).

MacDonald et al. "Approaches to Cyclic Peptide β-Turn Mimics", *Current Organic Chem.* 5:417-438 (2001).

Malagon et al. "Intracellular Signaling Mechanism Mediating Ghrelin-Stimulated Growth Hormone Release in Somatotropes" *Endocrinology* 144(12): 5372-5380 (2003).

Manhas et al. "Steroids. Part X. A Convenient Synthesis of Alkyl Aryl Ethers" *Journal of the Chemical Society Perkin I* 461-463 (1975).

Marguet et al. "New Synthesis of *sn*-1, 2- and *sn*-2,3-*O*-Diacylglycerols—Application to the Synthesis of Enantiopure Phosphonates Analogous to Triglycerides: A New Class of Inhibitors of Lipases" *European Journal of Organic Chemistry* pp. 1671-1678 (1999).

Meldal et al. "PEGA: A Flow Stable Polyethylene Glycol Dimethyl Acrylamide Copolymer for Solid Phase Synthesis" *Tetrahedron Letters* 33(21): 3077-3080 (1992).

Moreaux et al. "Activation of the GHS-Receptor Accelerates Gastric Emptying in Dogs" *Digestive Disease Week* 1 page poster presentation (2004).

Mori et al. "Synthesis of Monocerin, an Antifungal, Insecticidal and Phytotoxic Heptaketide Metabolite of Exerohilum Monoceras", *Tetrahedron* 45(6):1639-1646 (1989).

Murray et al. "Ghrelin for the Gastroenterologist: History and Potential" *Gastroenterology* 125: 1492-1502 (2003).

Murray et al. "Ghrelin enhances gastric emptying in diabetic gastroparesis: a double-blind, placebo-controlled, cross-over study", *Gut*, 54:1693-1698 (2005).

Nagaya et al. "Ghrelin Improves Left Ventricular Dysfunction and Cardiac Cachexia in Heart Failure" *Current Opinion in Pharmacology* 3: 146-151 (2003).

Nagaya et al. "Ghrelin, a Novel Growth Hormone-Releasing Peptide, in the Treatment of Chronic Heart Failure" *Regulatory Peptides* 114: 71-77 (2003).

Nakano et al. "An Efficient Synthesis of (S)-(-)-Befunolol Hydrochloride, Involving the Regioselective Condensation of (R)-Glycidol and 2-Acetyl-7-Hydroxybenzofuran" *Heterocycles* 20(10): 1975-1978 (1983).

Nakazato et al. "A Role for Ghrelin in the Central Regulation of Feeding" *Nature* 409: 194-198 (2001).

Nargund et al. "Peptidomimetic Growth Hormone Secretagogues. Design Considerations and Therapeutic Potential" *Journal of Medicinal Chemistry* 41(17): 3103-3127 (1998).

Ong et al. "Identification of a Pituitary Growth Hormone-Releasing Peptide (GHRP) Receptor subtype by Photoaffinity Labeling" *Endocrinology* 139(1): 432-435 (1998).

Palucki et al. "Spiro(indoline-3,4'-piperidine) Growth Hormone Secretagogues as Ghrelin Mimetics" *Bioorganic & Medicinal Chemistry Letters* 11: 1955-1957 (2001).

Pantel et al. "Loss of constitutive activity of the growth hormone secretagogue receptor in familial short stature", *J. Clin. Invest.*, 116:760-768 (2006).

Park et al. "Oligomerization of G Protein-Coupled Receptors: Past, Present, and Future" *Biochemistry* 43(50): 15643-15656 (2004).

Peeters "Central and Peripheral Mechanisms by which Ghrelin Regulates Gut Motility" *Journal of Physiology and Pharmacology* 54(suppl 4): 95-103 (2003).

Peeters et al. "Ghrelin: a new player in the control of gastrointestinal functions", *Gut*, 54:1638-1649 (2005).

Peeters, T.L. "Potential of ghrelin as a therapeutic approach for gastrointestinal motility disorders" *Curr. Opin. Pharmacol.* 6:553-558 (2006).

Persico et al. "Use of Hydrogen Bonds to Control Molecular Aggregation. Behavior of a Self-Complementary Dipyridone Designed to Self-Replicate" *Journal of Organic Chemistry* 58: 95-99 (1993).

Peschke et al. "New Growth Hormone Secretagogues: *C*-Terminal Modified Sulfonamide-Analogues of NN703" *Bioorganic & Medicinal Chemistry Letters* 9: 1295-1298 (1999).

Poitras et al. "Gastrokinetic effect of ghrelin analog RC-1139 in the rat. Effect on post-operative and on morphine induced ileus", *Peptides*, 26:1598-1601 (2005).

Prinster et al. "Heterodimerization of G protein-coupled receptors: specificity and functional significance", *Pharmacol. Rev.*, 57:289-298 (2005).

Qui et al. "Gastric motor effects of ghrelin and growth hormone releasing peptide 6 in diabetic mice with gastroparesis", *World Journal of Gastroenterology* 14(9):1419-1424 (2008).

Rapp et al. "Continuous Flow Peptide Synthesis on Pspoe-Graft-Copolymers" in *Innovation and perspectives in solid-phase synthesis* (Epton, R., ed.) pp. 205-210, SPCC, Birmingham. (1990).

Rios et al. "G-Protein-Coupled Receptor Dimerization: Modulation of Receptor Function" *Pharmacology & Therapeutics* 92: 71-87 (2001).

Romanovskis et al. "Preparation of head-to-tail cyclic peptides via side-chain attachment: Implications for library synthesis", *J. Peptide Res.* 52:356-374 (1998).

Roussel Jr., et al. "Risk Factors Associated with Development of Postoperative Ileus in Horses" *JAVMA* 219(1): 72-78 (2001).

Rudd et al. "Anti-emetic activity of ghrelin in ferrets exposed to the cytotoxic anti-cancer agent cisplatin", *Neurosci. Lett.*, 392:79-83 (2006).

Rudikoff et al. "Single amino acid substitution altering antigen-binding specificity", *Proc. Natl. Acad. Sci.* 79:1979-1983 (1982).

J. Rudinger "Characteristics of the amino acids as components of a peptide hormone sequence", *Peptide Hormones* pp. 1-7 (1976).

Samson et al. "Motilin: A Novel Growth Hormone Releasing Agent" *Brain Research Bulletin* 12: 57-62 (1984).

Sato et al. "Medium-sized Cyclophanes. Part XV. 10,15-Dihydro-5*H*-tribenzo-[a,d,g]cyclononene and Analogues", *J. Chem. Soc., Perkin 1* pp. 895-900 (1973).

Sato et al. "CsF in Organic Synthesis. Tuning of *N*- or *O*- Alkylation of 2-Pyridone" *Synlett* pp. 845-846 (Aug. 1995).
Semple et al. "3-Aryl Pyridone Derivatives. Potent and Selective Kappa Opioid Receptor Agonists" *Bioorganic & Medicinal Chemistry Letters* 12: 197-200 (2002).
Shiao et al. "A Facile Synthesis of Bromo-2-Alkoxypyridines" *Heterocycles* 31(5): 819-824 (1990).
Siani et al. "Development and screening of a polyketide virtual library for drug leads against a motilide pharmacophore", *J. Molecular Graphics and Modelling* 18:497-511 (2000).
Sibiliia et al. "Evidence for a role of the GHS-$R_{1a}$ receptors in ghrelin •nhibition of gastric acid secretion in the rat", *J. Neuroendocrinol.*, 18:122-128 (2006).
Sibiliia et al. "Ghrelin Protects Against Ethanol-Induced Gastric Ulcers in Rats: Studies on the Mechanisms of Action" *Endocrinology* 144(1): 353-359 (2003).
Smilek et al. "A single amino acid change in a myelin basic protein peptide confers the capacity to prevent rather than induce experimental autoimmune encephalomyelitis", *Proc. Natl. Acad. Sci.* 88:9633-9637 (1991).
Smith et al. "Current Concepts in Diabetic Gastroparesis" *Drugs* 63(13): 1339-1358 (2003).
Smith et al. "Growth Hormone Secretagogues: Prospects and Potential Pitfalls" *Best Practice & Research Clinical Endocrinology & Metabolism* 18(3):333-347 (2004).
Smith et al. "Peptidomimetic Regulation of Growth Hormone Secretion" *Endocrine Reviews* 18(5): 621-645 (1997).
Solomon et al. "Chemical Synthesis and Characterization of Duplex DNA Containing a New Base Pair: A Nondisruptive, Benzofused Pyrimiine Analog" *Journal of Organic Chemistry* 58: 2232-2243 (1993).
Souers et al. "β-Turn mimetic library synthesis: scaffolds and applications", *Tetrahedron* 57:7431-7448 (2001).
Spanswick et al. "Emerging antiobesity drugs", *Exp. Opin. Emerging Drugs* 8:217-237 (2003).
Suat Kee et al. "Design of β-turn Based Therapeutic Agents", *Current Pharmaceutical Design* 9:1209-1224 (2003).
Svensson et al. "Growth Hormone Secretagogues" *Expert Opinion on Therapeutic Patents* 10(7): 1071-1080 (2000).
Tack et al. "Influence of Ghrelin on Gastric Emptying and Meal-Related Symptoms in Idiopathic Gastroparesis" *Aliment Pharmacol Ther* 22: 847-853 (2005).
Tack et al. "Influence of Ghrelin on Interdigestive Gastrointestinal motility in Humans" *Gut* 55:327-333 (2006).
Takanashi et al. "GM-109: A Novel, Selective Motilin Receptor Antagonist in the Smooth Muscle of the Rabbit Small Intestine", *J. Pharm. & Experimental Therapeutics* 273(2):624-628 (1995).
Takeda et al. "Delayed gastric emptying after Billroth I pylorus preserving pancreatoduodenectomy. Effect of postoperative time and cisapride", *Ann. Surg.*, 229:223-229 (1999).
Tannenbaum et al. "Interrelationship Between the Novel Peptide Ghrelin and Somatostatin/Growth Hormone-Releasing Hormone in Regulation of Pulsatile Growth Hormone Secretion" *Endocrinology* 144(3): 967-974 (2003).
Tebbe et al. "Ghrelin-induced stimulation of colonic propulsion is dependent on hypothalamic neuropeptide Y1—and •orticotrophin-releasing factor 1 receptor activation", *J. Neuroendocrinol.* 17:570-576 (2005).

Tee et al. "Kinetics and Mechanism of Bromination of 2-Pyridone and Related Derivatives in Aqueous Solution" *Journal of the American Chemical Society* 104: 4142-4146 (1982).
Theodoridis "Nitrogen Protecting Gropus: Recent Developments and New Applications" *Tetrahedron Letters* 56: 2339-2358 (2000).
Thomber "Isoterism and Molecular Modification in Drug Design", *Chem. Soc. Rev.* 8(4):563-580 (1979).
Thompson et al. "Ghrelin and Des-Octanoyl Ghrelin Promote Adipogenesis Directly in Vivo by a Mechanism Independent of the Type 1a Growth Hormone Secretagogue Receptor" *Endocrinology* 145(1): 234-242 (2004).
Tomasetto et al. "Identification and Characterization of a Novel Gastric Peptide Hormone: The Motilin-Related Peptide" *Gastroenterology* 119: 395-405 (2000).
Torsello et al. "Differential Orexigenic Effects of Hexarelin and Its Analogs in the Rat Hypothalamus: Indication for Multiple Growth Hormone Secretagogue Receptor Subtypes" *Neuroendocrinology* 72: 327-332 (2000).
Trudel et al. "Ghrelin/Motilin-Related Peptide is a Potent Prokinetic to Reverse Gastric Postoperative Ileus in Rat" *American Journal of Gastrointestinal and Liver Physiology* 282: G948-G952 (2002).
Trudel et al. "Two New Peptides to Improve Post-Operative Gastric Ileus in Dog" *Peptides* 24: 531-534 (2003).
Tyndall et al. "Macrocycles Mimic the Extended Peptide Conformation Recognized by Aspartic, Serine, Cysteine and Metallo Proteases", *Current Medicinal Chem.* 8:893-907 (2001).
Van Hoogmoed et al. "Survey of Prokinetic use in Horses with Gastrointestinal Injury" *Veterinary Surgery* 33: 279-285 (2004).
Veber et al. "Molecular Properties that Influence the Oral Bioavailability of Drug Candidates", *J. Med. Chem.* 45:26156-2623 (2002).
Vedejs et al. "Heteroarene-2-sulfonyl Chlorides (BtsCl; ThsCl): Reagents for Nitrogen Protection and >99% Racemization-Free Phenylglycine Activation with $SoCl_2$," *Journal of the American Chemical Society* 118: 9796-9797 (1996).
Venkova et al. "Prokinetic Effects of a New Ghrelin Receptor Agonist TZP-101 in a Rat Model of Postoperative Ileus", *Dig. Dis. Sci.* 52:2241-2248 (2007).
Voet et al. *Biochemistry 2nd Ed.* pp. 235-241 (1995).
W.S. Messer, "Vasopressin and Oxytocin", web document updated Apr. 3, 2000; http://www.neurosci.pharm.utoledo.edu/MBC3320/vasopressin.htm 5 pages.
Wenlock et al. "A Comparison of Physiochemical Property Profiles of Development and Marketed Oral Drugs", *J. Med. Chem.* 46:1250-1256 (2003).
Zdravkovic et al. "A Clinical Study Investigating the Pharmacokinetic Interaction Between NN703 (tabimorelin), a Potential Inhibitor of CYP3A4 Activity, and Midazolam, a CYP3A4 Substrate" *European Journal of Pharmacology* 58: 683-688 (2003).
Zhang et al. "Lactone and Lactam Library Synthesis by Silver Ion-Assisted Orthogonal Cyclization of Unprotected Peptides" *Journal of the American Chemical Society* 121: 3311-3320 (1999).
"IUPAC-IUB Commission on Biochemical Nomenclature Symbols for Amino-Acid Derivatives and Peptides Recommendations", *J. Biol. Chem.* 247(4):977-983 (1972).

\* cited by examiner

Compound 25          Compound 298

A

B

Statistical analysis: * p<0.05 compared to vehicle,  p<0.01 compared to vehicle, * p<0.001 compared to vehicle, # p<0.05 compared to naïve (One-way ANOVA, Dunnet's post-hoc test).

The values shown are mean ± SEM; N values are as shown.
*$p<0.05$ or **$p<0.01$ in comparison to vehicle (One-way ANOVA, Dunnet's post-hoc test).

The values shown are mean ± SEM; N values are shown above individual bars.
*$p<0.05$ or **$p<0.01$ in comparison to vehicle (One-way ANOVA, Dunnet's post-hoc test).

A

B

Statistical Analysis: ** $p<0.01$ compared to vehicle, +$p<0.05$, ++$p<0.01$, +++$p<0.001$ compared to naïve
(One-way ANOVA with Bonferroni's MCT)

METHODS OF USING MACROCYCLIC AGONISTS OF THE GHRELIN RECEPTOR FOR TREATMENT OF GASTROINTESTINAL MOTILITY DISORDERS

RELATED APPLICATION INFORMATION

This application claims the benefit under 35 U.S.C. §119 (e) of U.S. Provisional Patent Application Ser. No. 60/818,915, filed Jul. 6, 2006, the disclosure of which is incorporated by reference herein in its entirety.

FIELD OF THE INVENTION

The present invention relates to novel conformationally-defined macrocyclic compounds that bind to and/or are functional modulators of the ghrelin (growth hormone secretagogue) receptor including GHS-R1a and subtypes, isoforms and/or variants thereof. These novel macrocyclic compounds are useful as therapeutics for a range of disease indications. In particular, these compounds are useful for treatment and prevention of multiple gastrointestinal disorders, whether occurring simultaneously or sequentially, including, but not limited to, post-operative ileus, gastroparesis, including idiopathic, diabetic and post-surgical gastroparesis, opioid bowel dysfunction, chronic intestinal pseudo-obstruction, short bowel syndrome and functional gastrointestinal disorders.

BACKGROUND OF THE INVENTION

The improved understanding of various physiological regulatory pathways enabled through the research efforts in genomics and proteomics has begun to impact the discovery of novel pharmaceutical agents. In particular, the identification of key receptors and their endogenous ligands has created new opportunities for exploitation of these receptor/ligand pairs as therapeutic targets. For example, ghrelin is a recently characterized 28-amino acid peptide hormone isolated originally from the stomach of rats with the orthologue subsequently identified in humans. (Kojima, M.; Hosoda, H. et al. Nature 1999, 402, 656-660.) The existence of this peptide in a range of other species suggests a conserved and important role in normal physiological function. This peptide has been demonstrated to be the endogenous ligand for a previously orphan G protein-coupled receptor (GPCR), type 1 growth hormone secretatogue receptor (hGHS-R1a) (Howard, A. D.; Feighner, S. D.; et al. A receptor in pituitary and hypothalamus that functions in growth hormone release. Science 1996, 273, 974-977.) found predominantly in the brain (arcuate nucleus and ventromedial nucleus in the hypothalamus, hippocampus and substantia nigra) and pituitary. (U.S. Pat. No. 6,242,199; Intl. Pat. Appl. Nos. WO 97/21730 and WO 97/22004) hGHS-R1a has recently been reclassified as the ghrelin receptor (GHRN) in recognition of its endogenous ligand (Davenport, A. P.; et al. International Union of Pharmacology. LVI. Ghrelin Receptor Nomenclature, Distribution, and Function. Pharmacol. Rev. 2005, 57, 541-546). The receptor has also been detected in other areas of the central nervous system (CNS) and in peripheral tissues, for instance adrenal and thyroid glands, heart, lung, kidney, and skeletal muscles. This receptor was identified and cloned prior to the isolation and characterization of the endogenous peptide ligand and is distinct from other receptors involved in the regulation of growth hormone (GH) secretion, in particular, the growth hormone-releasing hormone (GHRH) receptor.

A unique characteristic of both the rat and human peptides is the presence of the n-octanoyl (Oct) moiety on $Ser^3$. However, the des-acyl form predominates in circulation, with approximately 90% of the hormone in this form. This group is derived from a post-translational modification and appears relevant for bioactivity and possibly also for transport into the CNS. (Banks, W. A.; Tschöp, M.; Robinson, S. M.; Heiman, M. L. Extent and direction of ghrelin transport across the blood-brain barrier is determined by its unique primary structure. J. Pharmacol. Exp. Ther. 2002, 302, 822-827.) In a GH-releasing assay, the des-octanoyl form of the hormone was at least 100-fold less potent than the parent peptide, although it has been suggested that the des-acyl species may be responsible for some of the other biological effects associated with ghrelin. This des-acyl form has also been postulated to be primarily responsible for the cardiovascular and cell proliferation effects attributed to ghrelin, while the acylated form participates in maintenance of energy balance and growth hormone release. (Baldanzi, G.; Filighenddu, N.; Cutrupi, S.; et al. Ghrelin and des-acyl ghrelin inhibit cell death in cardiomyocytes and endothelial cells through ERK1/2 and PI-3 kinase/AKT. J. Cell Biol. 2002, 159, 1029-1037.) Similarly, des-$Gln^{14}$-ghrelin and its octanoylated derivative have been isolated as endogenous forms of the hormone arising from alternative splicing of the ghrelin gene, but both are found to be inactive in stimulating GH release in vivo. (Hosoda, H.; Kojima, M.; Matsuo, H.; Kangawa, K. Purification and characterization of rat des-$Gln^{14}$-ghrelin, a second endogenous ligand for the growth hormone secretagogue receptor. J. Biol. Chem. 2000, 275, 21995-22000.). Other minor forms of ghrelin produced by post-translational processing have been observed in plasma, although no specific activity has been attributed to them. (Hosoda, H.; Kojima, M.; et al. Structural divergence of human ghrelin. Identification of multiple ghrelin-derived molecules produced by post-translational processing. J. Biol. Chem. 2003, 278, 64-70.)

Even prior to the isolation of this receptor and its endogenous peptide ligand, a significant amount of research was devoted to finding agents that can stimulate GH secretion. The proper regulation of human GH has significance not only for proper body growth, but also a range of other critical physiological effects. GH and other GH-stimulating peptides, such as GHRH and growth hormone releasing factor (GRF), as well as their derivatives and analogues, are administered via injection. Therefore, to better take advantage of these positive effects, attention was focused on the development of orally active therapeutic agents that would increase GH secretion, termed GH secretagogues (GHS). Additionally, use of these agents was expected to be able to more closely mimic the pulsatile physiological release of GH.

Beginning with the identification of the growth hormone-releasing peptides (GHRP) in the late 1970's, (Bowers, C. Y. Growth hormone-releasing peptides: physiology and clinical applications. Curr. Opin. Endocrinol. Diabetes 2000, 7, 168-174; Camanni, F.; Ghigo, E.; Arvat, E. Growth hormone-releasing peptides and their analogs. Front. Neurosci. 1998, 19, 47-72; Locatelli, V.; Torsello, A. Growth hormone secretagogues: focus on the growth hormone-releasing peptides. Pharmacol. Res. 1997, 36, 415-423.) a host of agents have been studied for their potential to act as GHS. In addition to their stimulation of GH release and concomitant positive effects in that regard, GHS were projected to have utility in the treatment of a variety of other disorders, including wasting conditions (cachexia) as seen in HIV patients and cancer-induced anorexia, musculoskeletal frailty in the elderly, and growth hormone deficient diseases. Many efforts over the past 25 years have yielded a number of potent, orally available GHS. (Isidro, M. L.; Cordido, F. Growth hormone secretagogues. Comb. Chem. High Throughput Screen. 2006, 9, 178-180; Smith, R. G.; Sun, Y. X.; Beatancourt, L.; Asnicar, M. Growth hormone secretagogues: prospects and pitfalls. Best Pract. Res. Clin. Endocrinol. Metab. 2004, 18, 333-347; Fehrentz, J.-A.; Martinez, J.; Boeglin, D.; Guerlavais, V.; Deghenghi, R. Growth hormone secretagogues: Past, present and future. IDrugs 2002, 5, 804-814; Svensson, J. Exp. Opin. Ther. Patents 2000, 10, 1071-1080; Nargund, R. P.; Patchett, A. A.; et al. Peptidomimetic growth hormone secretagogues. Design considerations and therapeutic potential. J. Med. Chem. 1998, 41, 3103-3127; Ghigo, E; Arvat, E.; Camanni, F. Orally active growth hormone secretagogues: state of the art and clinical perspective. Ann. Med. 1998, 30, 159-168; Smith, R. G.; Van der Ploeg, L. H. T.; Howard, A. D.; Feigbner, S. D.; et al. Peptidomimetic regulation of growth hormone secretion. Endocr. Rev. 1997, 18, 621-645.). These include small peptides, such as hexarelin (Zentaris) and ipamorelin (Novo Nordisk), and adenosine analogues, as well as small molecules such as capromorelin (Pfizer), L-252,564 (Merck), MK-0677 (Merck), NN703 (tabimorelin, Novo Nordisk), G-7203 (Genentech), S-37435 (Kaken) and SM-130868 (Sumitomo), designed to be orally active for the stimulation of growth hormone. However, clinical testing with such agents have rendered disappointing results due to, among other things, lack of efficacy over prolonged treatment or undesired side effects, including irreversible inhibition of cytochrome P450 enzymes. (Zdravkovic M.; Olse, A. K.; Christiansen, T.; et al. Eur. J. Clin. Pharmacol. 2003, 58, 683-688.) Therefore, there remains a need for pharmacological agents that could effectively target the ghrelin receptor for therapeutic action.

Despite its involvement in GH modulation, ghrelin is primarily synthesized in the oxyntic gland of the stomach, although it is also produced in lesser amounts in other organs, including the kidney, pancreas and hypothalamus. (Kojima, M.; Hsoda, H.; Kangawa, K. Purification and distribution of ghrelin: the natural endogenous ligand for the growth hormone secretagogue receptor. Horm. Res. 2001, 56 (Suppl. 1), 93-97; Ariyasu, H.; Takaya, K.; Tagami, T.; et al. Stomach is a major source of circulating ghrelin, and feeding state determines plasma ghrelin-like immunoreactivity levels in humans. J. Clin. Endocrinol. Metab. 2001, 86, 4753-4758.) In addition to its role in stimulating GH release, the hormone has a variety of other endocrine and non-endocrine functions (Broglio, F.; Gottero, C.; Arvat, E.; Ghigo, E. Endocrine and non-endocrine actions of ghrelin. Horm. Res. 2003, 59, 109-117; Hosoda, H.; Kojima, M.; Kangawa, K. Biological, physiological, and pharmacological aspects of ghrelin. J. Pharmacol. Sci. 2006, 100, 398-410.) and has been shown to interact with a number of other systems in playing a role in maintaining proper energy balance. (Horvath, T. L.; Diano, S.; Sotonyi, P.; Heiman, M.; Tschop, M. Ghrelin and the regulation of energy balance—a hypothalamic perspective. Endocrinology 2001, 142, 4163-4169; Casanueva, F. F.; Dieguez, C. Ghrelin: the link connecting growth with metabolism and energy homeostasis. Rev. Endocrinol. Metab. Disord. 2002, 3, 325-338.) In particular, ghrelin plays a role as an orexigenic signal in the control of feeding, in which it acts to counteract the effects of leptin. Indeed, it was the first gut peptide proven to have such orexigenic properties. (Kojima, M.; Kangawa, K. Ghrelin, an orexigenic signaling molecule from the gastrointestinal tract. Curr. Opin. Pharmacology 2002, 2, 665-668.) The hormone also is implicated in the hypothalamic regulation of the synthesis and secretion of a number of other neuropeptides involved in appetite and feeding behavior. Levels of ghrelin are elevated in response to fasting or extended food restriction. (Nakazato, M.; Murakami, N.; Date, Y.; Kojima, M.; et al. A role for ghrelin in the central regulation of feeding. Nature 2001, 409, 194-198.) For example, subjects suffering with anorexia or bulimia exhibit elevated ghrelin levels. Circulating levels of the hormone have been found to rise before meals and fall after meals. In addition, diet-induced weight loss leads to increased ghrelin levels, although obese subjects who have gastric bypass surgery do not likewise experience such an increase. (Cummings, D. E.; Weigle, D. S.; Frayo, R. S.; et al. Plasma ghrelin levels after diet-induced weight loss or gastric bypass surgery. N. Engl. J. Med. 2002, 346, 1623-1630.)

This intimate involvement of ghrelin in control of food intake and appetite has made it an attractive target for obesity research. (Spanswick, D.; Lee, K. Emerging antiobesity drugs. Exp. Opin. Emerging Drugs 2003, 8, 217-237; Horvath, T. L.; Castaiieda, T.; Tang-Christensen, M.; Pagotto, U.; Tschöp, M. H. Ghrelin as a potential anti-obesity target. Curr. Pharm. Design 2003, 9, 1383-1395; Crowley, V. E. F.; Yeo, G. S. H.; O-Rahilly, S. Obesity therapy: altering the energy intake-and-expenditure balance sheet. Nat. Rev. Drug Disc. 2002, 1, 276-286.) Indeed, few other natural substances have been demonstrated to be involved in the modulation of both GH secretion and food intake.

An additional effect of ghrelin that has not to date been exploited for therapeutic purposes is in modulating gastric motility and gastric acid secretion. The prokinetic activity appears to be independent of the GH-secretory action and is likely mediated by the vagal-cholinergic muscarinic pathway. The dose levels required are equivalent to those necessary for the hormone's GH and appetite stimulation actions. It is noteworthy that, in contrast to its inactivity for ghrelin's other actions, the des-acyl and des-Gln$^{14}$ peptides demonstrated promotion of GI motility as well. (Chen, C.-Y.; Inui, A.; Asakawa, A.; Fujino, K.; Kato, I.; Chen, C.-C.; Ueno, N.; Fujimiya, M. Des-acyl ghrelin acts by CRF type 2 receptors to disrupt fasted stomach motility in conscious rats. Gastroenterology 2005, 129, 8-25; Chen, C.-Y.; Chao, Y.; Chang, F.-Y.; Chien, E. J.; Lee, S.-D.; Doong, M.-L. Intracisternal des-acyl ghrelin inhibits food intake and non-nutrient gastric emptying in conscious rats. Int. J. Mol. Med. 2005, 16, 695-699; Trudel, L.; Bouin, M.; Tomasetto, C.; Eberling, P.; St-Pierre, S.; Bannon, P.; L'Heureux, M. C.; Poitras, P. Two new peptides to improve post-operative gastric ileus in dog. Peptides 2003, 24, 531-534; Trudel, L.; Tomasetto, C.; Rio, M. C.; Bouin, M.; Plourde, V.; Eberling, P.; Poitras, P. Ghrelin/motilin-related peptide is a potent prokinetic to reverse gastric postoperative ileus in rats. Am. J. Physiol. 2002, 282, G948-G952; Peeters, T. L. Central and peripheral mechanisms by which ghrelin regulates gut motility. J. Physiol. Pharmacol. 2003, 54(Supp. 4), 95-103.)

Ghrelin also has been implicated in various aspects of reproduction and neonatal development. (Arvat, E.; Gianotti, L.; Giordano, R.; et al. Growth hormone-releasing hormone and growth hormone secretagogue-receptor ligands. Focus on reproductive system. Endocrine 2001, 14, 35-43.) Also of significance are the cardiovascular effects of ghrelin, since the peptide is a powerful vasodilator. As such, ghrelin agonists have potential for the treatment of chronic heart failure. (Nagaya, N.; Kangawa, K. Ghrelin, a novel growth hormone-releasing peptide, in the treatment of chronic heart failure. Regul. Pept. 2003, 114, 71-77; Nagaya, N.; Kangawa, K. Ghrelin improves left ventricular dysfunction and cardiac cachexia in heart failure. Curr. Opin. Pharmacol. 2003, 3, 146-151; Bedendi, I.; Alloatti, G.; Marcantoni, A.; Malan, D.; Catapano, F.; Ghé, C.; et al. Cardiac effects of ghrelin and its endogenous derivatives des-octanoyl ghrelin and des-Gln$^{14}$-ghrelin. Eur. J. Pharmacol. 2003, 476, 87-95; Isgaard, J.;

Johansson, I. Ghrelin and GHS on cardiovascular applications/functions. J. Endocrinol. Invest. 2005, 28, 838-842.) Intl. Pat. Appl. Publ. WO 2004/014412 describes the use of ghrelin agonists for the protection of cell death in myocardial cells and as a cardioprotectant treatment for conditions leading to heart failure.

WO 2005/097174 and WO 2006/045314 discuss the use of GHS, ghrelin and other peptides or combinations thereof for the treatment of cachexia and chronic obstructive pulmonary disease, respectively. WO 2005/09726 reports on GHS for treatment of diseases caused by C-reactive protein. WO 2006/045319 describes the use of GHS in the treatment of renal and/or liver failure and complications thereof. More generally, WO 2005/097173 suggests the use of GHS for the treatment of ghrelin deficiency, including a wide array of therapeutic indications. Lastly, evidence has been obtained that ghrelin may have implications in anxiety and other CNS disorders as well as the improvement of memory. (Carlini, V. P., Monzon, M. E., Varas, M. M., Cragnolini, A. B., Schioth, H. B., Scimonelli, T. N., de Barioglio, S. R. Ghrelin increases anxiety-like behavior and memory retention in rats. Biochem. Biophys. Res. Commun. 2002, 299, 739-743; Diano, S. Farr, S. A.; Benoit, S. C.; et al. Ghrelin controls hippocampal spine synapse density and memory performance. Nat. Neuroscience 2006, 9, 381-388.)

The myriad effects of ghrelin in humans have suggested the existence of subtypes for its receptor, although none have as yet been identified. (Torsello, A.; Locatelli, Y.; Melis, M. R.; Succu, S.; Spano, M. S.; Deghenghi, R.; Muller, E. E.; Argiolas, A.; Torsello, A.; Locatelli, V.; et al. Differential orexigenic effects of hexarelin and its analogs in the rat hypothalamus: indication for multiple growth hormone secretagogue receptor subtypes. Neuroendocrinology 2000, 72, 327-332.) However, a truncated, inactive form of GHS-R1a, termed GHS-R1b, was isolated and identified during the original characterization studies. Evidence is mounting that additional receptor subtypes could be present in different tissues to explain the diverse effects displayed by the endogenous peptides and synthetic GHS. For instance, high affinity binding sites for ghrelin and des-acyl ghrelin have also been found in breast cancer cell lines, cardiomyocytes, and guinea pig heart that are involved in mediating the antiproliferative, cardioprotective and negative cardiac inotropic effects of these peptides. Similarly, specific GHS binding sites besides GHS-R1a and GHS-R1b have been found in prostate cancer cells. Further, ghrelin and des-acyl ghrelin exert different effects on cell proliferation in prostate carcinoma cell lines. (Cassoni, P.; Ghé, C.; Marrocco, T.; et al. Expression of ghrelin and biological activity of specific receptors for ghrelin and des-acyl ghrelin in human prostate neoplasms and related cell lines. Eur. J. Endocrinol. 2004, 150, 173-184.) These various receptor subtypes may then be implicated independently in the wide array of biological activities displayed by the endogenous peptides and synthetic GHS. Indeed, recently, the existence of receptor subtypes was offered as an explanation for the promotion of fat accumulation by ghrelin, despite its potent stimulation of the lipolytic hormone, growth hormone. (Thompson, N. M.; Gill, D. A. S.; Davies, R.; Loveridge, N.; Houston, P. A.; Robinson, I. C. A. F.; Wells, T. Ghrelin and des-octanoyl ghrelin promote adipogenesis directly in vivo by a mechanism independent of the type 1a growth hormone secretagogue receptor. Endocrinology 2004, 145, 234-242.) Further, this work suggested that the ratio of ghrelin and des-acyl ghrelin production could help regulate the balance between adipogenesis and lipolysis in response to nutritional status.

The successful creation of peptidic ghrelin analogues that separate the GH-modulating effects of ghrelin from the effects on weight gain and appetite also provides strong evidence for the existence and physiological relevance of other receptor subtypes. (Halem, H. A.; Taylor, J. E.; Dong, J. Z.; Shen, Y.; Datta, R.; Abizaid, A; Diano, S.; Horvath, T. L.; Culler, M. D. A novel growth hormone secretagogue-1a receptor antagonist that blocks ghrelin-induced growth hormone secretion but induces increased body weight gain. Neuroendocrinol. 2005, 81, 339-349; Halem, H. A.; Taylor, J. E.; Dong, J. Z.; Shen, Y.; Datta, R.; Abizaid, A.; Diano, S.; Horvath, T.; Zizzari, P.; Bluet-Pajot, M.-T.; Epelbaum, J.; Culler, M. D. Novel analogs of ghrelin: physiological and clinical implications. Eur. J. Endocrinol. 2004, 151, S71-S75.) BIM-28163 functions as an antagonist at the GHS-R1a receptor and inhibits receptor activation by native ghrelin. However, this same molecule is a full agonist with respect to stimulating weight gain and food intake. Additionally, the existence of a still uncharacterized receptor subtype has been proposed based on binding studies in various tissues that showed differences between peptidic and non-peptidic GHS. (Ong, H.; Menicoll, N.; Escher, F.; Collu, R.; Deghenghi, R.; Locatelli, V.; Ghigo, E.; Muccioli, G.; Boghen, M.; Nilsson, M. Endocrinology 1998, 139, 432-435.) Differences between overall GHS-R expression and that of the GHS-R1a subtype in rat testis have been reported. (Barreiro, M. L.; Suominen, J. S.; Gaytan, F.; Pinilla, L.; Chopin, L. K.; Casanueva, F. F.; Dieguez, C.; Aguilar, E.; Toppari, J.; Tena-Sempere, M. Developmental, stage-specific, and hormonally regulated expression of growth hormone secretagogue receptor messenger RNA in rat testis. Biol. Reproduction 2003, 68, 1631-1640.) A GHS-R subtype on cholinergic nerves is postulated as an explanation for the differential actions of ghrelin and a peptidic GHS on neural contractile response observed during binding studies at the motilin receptor. (Depoortere, I.; Thijs, T.; Thielemans, L.; Robberecht, P.; Peeters, T. L. Interaction of the growth hormone-releasing peptides ghrelin and growth hormone-releasing peptide-6 with the motilin receptor in the rabbit gastric antrum. J. Pharmacol. Exp. Ther. 2003, 305, 660-667.) Finally, the macrocyclic ghrelin agonists described in WO 2006/009645 and WO 2006/009674 report the separation of the G1 effects from the GH-release effects in animal models, also suggesting that different subtypes are involved in these physiological effects.

The variety of activities associated with the ghrelin receptor could also be due to different agonists activating different signaling pathways as has been shown for ghrelin and adenosine, both of which interact as agonists at GHS-R1a (Carreira, M. C.; Camina, J. P.; Smith, R. G.; Casanueva, F. F. Agonist-specific coupling of growth hormone secretagogue receptor type 1a to different intracellular signaling systems. Role of adenosine. Neuroendocrinology 2004, 79, 13-25.)

The functional activity of a GPCR has been shown to often require the formation of dimers or other multimeric complexes with itself or other proteins. (Prinster, S. C.; Hague, C.; Hall, R. A. Heterodimerization of G protein-coupled receptors: specificity and functional significance. Pharmacol. Rev. 2005, 57, 289-298; Hansen, J. L.; Sheikh, S. P. Functional consequences of 7TM receptor dimerization. Eur. J. Pharm. Sci. 2004, 23, 301-317; Park, P. S.; Filipek, S.; Wells, J. W.; Palczewski, K. Oligomerization of G protein-coupled receptors: past, present, and future. Biochemistry 2004, 43, 15643-15656; Rios, C. D.; Jordan, B. A.; Gomes, I.; Devi, L. A. G-protein-coupled receptor dimerization: modulation of receptor function. Pharmacol. Ther. 2001, 92, 71-87; Devi, L. A. Heterodimerization of G-protein-coupled receptors: pharmacology, signaling and trafficking. Trends Pharmacol. Sci.

2001, 22, 532-537.) Likewise, the activity of the ghrelin receptor might also be at least partially governed by such complexes. For example, certain reports indicate that interaction of GHS-R1a with GHRH (Cunha, S. R.; Mayo, K. E. Ghrelin and growth hormone (GH) secreatagogues potentiate GH-releasing hormone (GHRH)-induced cyclic adenosine 3',5'-monophosphate production in cells expressing transfected GHRH and GH secretagogue receptors. Endocrinology 2002, 143, 4570-4582; Malagón, M. M.; Luque, R. M.; Ruiz-Guerrero, E.; Rodríguez-Pacheco, F.; Garcia-Navarro, S.; Casanueva, F. F.; Gracia-Navarro, F.; Castaño, J. P. Intracellular signaling mechanisms mediating ghrelin-stimulated growth hormone release in somatotropes Endocrinology 2003, 144, 5372-5380.) or between receptor subtypes (Chan, C. B.; Cheng, C. H. K. Identification and functional characterization of two alternatively spliced growth hormone secretagogue receptor transcripts from the pituitary of black seabream Acanthopagrus schlegeli. Mol. Cell. Endocrinol. 2004, 214, 81-95.) may be involved in modulating the function of the receptor.

Further, the appetite regulating effects of ghrelin have been attributed to the constitutive activity of the receptor. (Holst, B. Schwartz, T. Ghrelin receptor mutations—too little height and too much hunger. J. Clin. Invest. 2006, 116, 637-641; Holst, B.; Schwartz, T. W. Constitutive ghrelin receptor activity as a signaling set-point in appetite regulation. Trends Pharmacol. Sci. 2004, 25, 113-117; Holst, B.; Holliday, N. D.; Bach, A.; Elling, C. E.; Cox, H. M.; Schwartz, T. W. Common structural basis for constitutive activity of the ghrelin receptor family. J. Biol. Chem. 2004, 279, 53806-53817; Holst, B.; Cygankiewicz, A.; Jensen, T. H.; Ankersen, M.; Schwartz, T. W. High constitutive signaling of the ghrelin receptor—identification of a potent inverse agonist. Mol. Endocrinol. 2003, 17, 2201-221.) The recent observation that humans possessing a mutation in the glrelin receptor that impairs constitutive activity are of short stature suggests the importance of the constitutive activity to the normal in vivo function of this receptor. (Pantel, J.; Legendre, M. Cabrol, S.; et al. Loss of constitutive activity of the growth hormone secretagogue receptor in familial short stature. J. Clin. Invest. 2006, 116, 760-768.)

The vast majority of reported approaches to exploiting the ghrelin receptor for therapeutic purposes have focused on modulating metabolic functions. Similarly, the vast majority of literature on GHS focuses on conditions that can be treated via its GH promoting actions. Some embodiments of the invention described herein, in particular, take advantage of selective activation of the ghrelin receptor to provide an avenue for the treatment of diseases characterized by GI dysmotility. The improved GI motility observed with ghrelin demonstrates that ghrelin agonists may be useful in correcting conditions associated with reduced or restricted motility (Murray, C. D. R.; Kamm, M. A.; Bloom, S. R.; Emmanuel, A. V. Ghrelin for the gastroenterologist: history and potential. Gastroenterology 2003, 125, 1492-1502; Fujino, K.; Inui, A.; Asakawa, A.; Kihara, N.; Fujimura, M.; Fujimiya, M. Ghrelin induces fasting motor activity of the gastrointestinal tract in conscious fed rats. J. Physiol. 2003, 550, 227-240; Edholm, T.; Levin, F.; Hellstrom, P. M.; Schmidt, P. T. Ghrelin stimulates motility in the small intestine of rats through intrinsic cholinergic neurons. Regul. Pept. 2004, 121, 25-30; Locatelli, V.; Bresciani, E.; Bulgarelli, I.; Rapetti, D.; Torsello, A.; Rindi, G.; Sibilia, V. Netti, C. Ghrelin in gastroenteric pathophysiology. J. Endocrinol. Invest. 2005, 28, 843-848; Peeters, T. L. Ghrelin: a new player in the control of gastrointestinal functions. Gut 2005, 54, 1638-1649.)

Included among these conditions is postoperative ileus (POI, Luckey, A.; Livingston, E.; Taché, Y. Mechanisms and treatment of postoperative ileus. Arch. Surg. 2003, 138, 206-214; Baig, M. K.; Wexner, S. D. Postoperative ileus: a review. Dis. Colon Rectum 2004, 47, 516-526). POI is defined as the impairment of GI motility that routinely occurs following abdominal, intestinal, gynecological and pelvic surgeries. In the U.S. alone, 2.1 million surgeries annually can induce POI, accounting for an economic impact of over $1 billion. POI is considered a deleterious response to surgical manipulation with a variable duration that generally persists for at least 72 hours. It is characterized by pain, abdominal distention or bloating, nausea and vomiting, accumulation of gas and fluids in the bowel, and delayed passage of stool. Patients are neither able to tolerate oral feeding nor to have bowel movements until gut function returns. POI leads to numerous undesirable consequences, including increased patient morbidity, the costly prolongation of hospital stays and, further, is a major cause of hospital readmission. In addition, opiate drugs given as analgesics after surgery exacerbate this condition due to their well-recognized side effect of inhibiting bowel function.

Surgical manipulation of the stomach or intestine causes a disorganization of the gut-brain signaling pathways, impairing GI activity and triggering POI. Ghrelin acts locally in the stomach to stimulate and coordinate the firing of vagal afferent neurons and thereby modulate gut motility. Thus, ghrelin accelerates gastric emptying in humans (Petters, T. L. Potential of ghrelin as a therapeutic approach for gastrointestinal motility disorders. Curr. Opin. Pharmacol. 2006, 6, 553-558; Tack, J.; Depoortere, I.; Bisschops, R.; Delporte, C.; Coulie, B.; Meulemans, A.; Janssens, J.; Peeters, T. Influence of ghrelin on interdigestive gastrointestinal motility in humans. Gut 2006, 55, 327-333; Inui, A.; Asakawa, A.; Bowers, C. Y.; Mantovani, G.; Laviano, A.; Meguid, M. M.; Fujimiya, M. Ghrelin, appetite, and gastric motility: the emerging role of the stomach as an endocrine organ. FASEB J. 2004, 18, 439-456; Peeters, T. L. Central and peripheral mechanisms by which ghrelin regulates gut motility. J. Physiol. Pharmacol. 2003, 54(Supp. 4), 95-103.) and is a potent agent proven to treat ileus in animal models (Trudel, L.; Tomasetto, C.; Rio, M. C.; Bouln, M.; Plourde, V.; Eberling, P.; Poitras, P. Ghrelin/motilin-related peptide is a potent prokinetic to reverse gastric postoperative ileus in rats. Am. J. Physiol. 2002, 282, G948-G952; Tridel, L.; Bouin, M.; Tomasetto, C.; Eberling, P.; St-Pierre, S.; Bannon, P.; L'Heureux, M. C.; Poitras, P. Two new peptides to improve post-operative gastric ileus in dog. Peptides 2003, 24, 531-534; De Winter, B. Y.; De Man, J. G.; Seerden, T. C.; Depoortere, I.; Herman, A. G.; Peeters, T. L.; Pelckmans, P. A. Effect of ghrelin and growth hormone-releasing peptide 6 on septic ileus in mice. Neurogastroenterol. Motil. 2004, 16, 439-446.). Ghrelin agonists can duplicate the GI stimulating effects of ghrelin, thus targeting directly the underlying cause of POI to accelerate normalization of gut function and enable more rapid discharge from the hospital. (Kitazawa, T.; De Smet, B.; Verbeke, K.; Depoortere, I.; Peeters, T. L. Gastric motor effects of peptide and non-peptide ghrelin agonists in mice in vivo and in vitro. Gut 2005, 54, 1078-1084; Poitras, P.; Polyino, W. J.; Rocheleau, B. Gastrokinetic effect of ghrelin analog RC-1139 in the rat. Effect on post-operative and on morphine induced ileus. Peptides 2005, 26, 1598-1601.) The reported anti-inflammatory actions of ghrelin may also play a role in ameliorating this condition. (Granado, M.; Priego, T.; Martin, A. I.; Villanua, M. A.; Lopez-Calderon, A. Anti-inflammatory effect of the ghrelin agonist growth hormone-releasing peptide-2 (GHRP-2) in arthritic rats. Am. J. Physiol. Endocrinol. Metab. 2005, 288, E486-E492; Iseri, S. O.; Sener, G.; Yuksel, M.; Contuk, G.; Cetinel, S.; Gedik, N.; Yegen, B. C. Ghrelin against alendronate-induced gastric damage in rats. J. Endocrinol. 2005, 187, 399-406.)

Intravenous administration is often the preferred route of treatment for POI due to the impaired GI motility in these patients that impedes oral therapy. No agent is currently approved by the U.S. FDA specifically for the treatment of POI.

Another major motility disorder is gastroparesis, a particular problem for both type I and type II diabetics. (Camilleri, M. Advances in diabetic gastroparesis. Rev. Gastroenterol. Disord. 2002, 2, 47-56; Abell, T. L.; Bernstein, R. K.; Cutts, T.; Treatment of gastroparesis: a multidisciplinary clinical review. Neurogastrenterol. Motil. 2006, 18, 263-283; Camilleri, M. Diabetic gastroparesis. New Eng. J. Med. 2007, 356, 820-829.) Gastroparesis ("stomach paralysis") is a syndrome characterized by delayed gastric emptying in the absence of any mechanical obstruction. It is variably characterized by abdominal pain, nausea, vomiting, weight loss, anorexia, early satiety, malnutrition, dehydration, gastroesophageal reflux, cramping and bloating. This chronic condition can lead to frequent hospitalization, increased disability and decreased quality of life. Severe, symptomatic gastroparesis is common in individuals suffering from diabetes, affecting from 5-10% of diabetics for a total patient population of 1 million in the U.S. alone. Neuropathy is a frequent, debilitating complication of diabetes. Visceral neuropathy results in GI dysfunction, especially involving the stomach, leading to impaired gastric motility. Ghrelin promotes gastric emptying both by stimulating the vagus nerve and via direct prokinetic action at the gastric mucosa. Moreover, recent clinical studies indicate that intravenous administration of the natural ghrelin peptide is an effective acute therapy in gastroparesis patients. (Binn, M.; Albert, C.; Gougeon, A.; Maerki, H.; Coulie, B.; Lemoyne, M.; Rabasa Lhoret, R.; Tomasetto, C.; Poitras, P. Ghrelin gastrokinetic action in patients with neurogenic gastroparesis. Peptides 2006, 27, 1603-1606; Murray, C. D. R.; Martin, N. M.; Patterson, M.; Taylor, S.; Ghatei, M. A.; Kamm, M. A.; Johnston, C.; Bloom, S. R.; Emmanuel, A. V. Ghrelin enhances gastric emptying in diabetic gastroparesis: a double-blind, placebo-controlled, cross-over study. Gut 2005, 54, 1693-1698; Tack, J.; Depoortere, I.; Bisschops, R.; Verbeke, K.; Janssens, J.; Peeters, T. Influence of ghrelin on gastric emptying and meal-related symptoms in idiopathic gastroparesis. Aliment. Pharmacol. Ther. 2005, 22, 847-853.)

A ghrelin agonist would therefore be highly effective in overcoming the fundamental motility barrier faced by gastroparesis patients and correcting this condition. As with POI, no accepted or efficacious therapy for diabetic gastroparesis is available and most current therapies aim to provide only symptomatic relief. Further, many of the therapeutics in development have a mechanism of action similar to earlier products that have failed in this indication. Surgical procedures may ameliorate the disease process, but offer no possibility of cure.

Post-surgical gastroparesis syndrome is a complication resulting from surgery characterized by delayed gastric emptying, postprandial nausea and vomiting, and abdominal pain. (Eckhauser, F. E., et al. Am. Surg. 1998, 64, 711-717; Tanaka, M. Surg. Today 2005, 35, 345-350.) These surgeries include gastrectomy, pancreatoduodenectomy, gastrojejunostomy in patients with pancreatic cancer and gastric surgery, as well as in patients with liver cirrhosis. (Doberneck, R. C.; Berndt, G. A. Delayed gastric emptying after palliative gastrojejunostomy for carcinoma of the pancreas. Arch. Surg. 1987, 122, 827-829; Bar-Natan, M.; Larson, G. M.; Stephens, G.; Massey, T. Delayed gastric emptying after gastric surgery. Am. J. Surg. 1996, 172, 24-28; Cohen, A. M.; Ottinger, L. W. Delayed gastric emptying following gastrectomy. Ann. Surg. 1976, 184, 689-696; Isobe, H.; Sakai, H.; Satoh, M.; Sakamoto, S.; Nawata, H. Delayed gastric emptying in patients with liver cirrhosis. Dig. Dis. Sci. 1994, 39, 983-987.) The only reported pharmaceutical agents shown to be useful for this syndrome are cisapride and erythromycin. (Takeda, T.; Yoshida, J.; Tanaka, M.; Matsunaga, H.; Yamaguchi, K.; Chijiiwa, K. Delayed gastric emptying after Billroth I pylorus preserving pancreatoduodenectomy. Effect of postoperative time and cisapride. Ann. Surg. 1999, 229, 223-229; Heidenreich, A.; Wille, S.; Hofinann, R. J. Urology 2000, 163, 545.) However, cisapride was removed from the market due, at least in part, to the appearance of life-threatening cardiac arrhythmia side effects. Further, erythromycin is not a desirable treatment due to the antibiotic activity potentially giving rise to resistance should it be used for non-infective purposes.

Opioid-induced bowel dysfunction (OBD, Kurz, A.; Sessler, D. J. Opioid-Induced Bowel Dysfunction. Drugs 2003, 63, 649-671.) is the term applied to the confluence of symptoms involving the reduced GI motility that results from treatment with opioid analgesics. Approximately 40-50% of patients taking opioids for pain control experience OBD. It is characterized by hard, dry stools, straining, incomplete evacuation, bloating, abdominal distension and increased gastric reflux. In addition to the obvious short-term distress, this condition leads to physical and psychological deterioration in patients undergoing long term opioid treatment. Further, the dysfunction can be so severe as to become a dose-limiting adverse effect that actually prevents adequate pain control. As with POI, a ghrelin agonist can be expected to counteract the dysmotility resulting from opioid use.

Two less common conditions may also be helped through the GI motility stimulation effects of ghrelin and ghrelin agonists. Short bowel syndrome is a condition that occurs after resection of a substantial portion of small intestine and is characterized by malnutrition. Patients are observed to have decreased ghrelin levels resulting from loss of the ghrelin-producing neuroendocrine cells of the intestine. It is possible the short bowel feeds back on the release of the hormone. (Krsek, M.; Rosicka, M.; Haluzik, M.; et al. Plasma ghrelin levels in patients with short bowel syndrome. Endocr. Res. 2002, 28, 27-33.) Chronic intestinal pseudo-obstruction is a syndrome defined by the presence of chronic intestinal dilation and dysmotility in the absence of mechanical obstruction or inflammation. Both genetic and acquired causes are known to result in this disorder, which affects high numbers of individuals worldwide annually. (Hirano, I.; Pandolfino, J. Chronic intestinal pseudo-obstruction. Dig. Dis. 2000, 18, 83-92.)

Other conditions and disorders that could be addressed through stimulation of the ghrelin receptor are: constipation such as associated with the hypomotility phase of irritable bowel syndrome (IBS), delayed gastric emptying associated with wasting conditions, gastroesophageal reflux disease (GERD), gastric ulcers (Sibilia, V.; Muccioli, G.; Deghenghi, R.; Pagani, F.; DeLuca, V.; Rapetti, D.; Locatelli, V.; Netti, C. Evidence for a role of the GHS-R1a receptor in ghrelin inhibition of gastric acid secretion in the rat. J. Neuroendocrinol. 2006, 18, 122-128; Sibilia, V.; Rindi, G.; Pagani, F.; Rapetti, D.; Locatelli, V.; Torsello, A.; Campanini, N.; Degenghi, R.; Netti, C. Ghrelin protects against ethanol-induced gastric ulcers in rats: studies on the mechanism of action. Endocrinology 2003, 144, 353-359.) and Crohn's disease. Ghrelin and ghrelin agonists also have been described as treatments for nausea, emesis or symptoms thereof. (U.S. Pat. Appl. Pub.

No. 2005/277677; Rudd, J. A.; Ngan, M. P.; Wai, M. K.; King, A. G.; Witherington, J.; Andrews, P. L. R.; Sanger, G. J. Anti-emetic activity of ghrelin in ferrets exposed to the cytotoxic anti-cancer agent cisplatin. Neurosci. Lett. 2006, 392, 79-83.)

Additionally, GI dysmotility is a significant problem in other mammals as well. For example, the motility dysfunction termed ileus or colic is the number one cause of mortality among horses. Further, ileus is one of the most common complications of equine intestinal surgery, in other words, post-operative ileus. This condition may also have a non-surgical etiology. Some horses may be predisposed to ileus based upon the anatomy and functioning of their digestive tract. Virtually any horse is susceptible to colic with only minor differences based upon age, sex and breed. Additionally, ileus may affect other animals, for example canines. (Roussel, A. J., Jr.; Cohen, N. D.; Hooper, R. N.; Rakestraw, P. C. Risk factors associated with development of postoperative ileus in horses. J. Am. Vet. Med. Assoc. 2001, 219, 72-78; Van Hoogmoed, L. M.; Nieto, J. E.; Snyder, J. R.; Harmon, F. A. Survey of prokinetic use in horses with gastrointestinal injury. Vet. Surg. 2004, 33, 279-285.)

Further, many GI disorders are experienced simultaneously. In particular when opioids are used for pain management during surgery, OBD can exacerbate POI, which often results from surgery.

Importantly, for most of the above conditions, no specific, approved therapeutics exist and most therapies simply address symptomatic relief. However, specific modulation of the ghrelin receptor provides an opportunity to directly target the site of pathophysiological disturbance to better treat the underlying condition and improve clinical outcome. Further, unlike other agents that interact at the ghrelin receptor, the macrocyclic compounds of the invention are believed not to stimulate concurrent GH secretion as demonstrated in animal models. This separation of the gastrointestinal and GH effects has not previously been reported for any modulators of this receptor. However, as already mentioned, the existence of analogues that separate the appetite control and GH modulatory effects associated with ghrelin has been recently reported.

WO 01/00830 reports on short gastrointestinal peptides (SGIP) that secrete growth hormone and also promote GI motility, but these were not shown to be due to action at the ghrelin receptor. Similarly, WO 2007/041278 describes peptide analogues of ghrelin that stimulate GI motility. U.S. Pat. Nos. 6,548,501 and 6,852,722 discuss specific non-peptidic GHS compounds useful for stimulation of GI motility. Similarly, WO 2006/010629, WO 2006/020930 and WO 2006/023608 describe ghrelin agonists (growth hormone secretagogues) for use in GI disorders. Moreover, other endogenous factors are known to stimulate secretion of GH, but do not promote GI motility. Indeed, many actually inhibit this physiological function. Specific receptor agonists such as the compounds of the present invention have much better potential to be selective and effective therapeutic agents.

However, these ghrelin agonists are typically used in higher dose levels in order to effectively treat combination GI disorders. For example, RC-1139 required a higher dose level (10 mg/kg) to restore gastric emptying to normal values in rats with concurrent conditions of PO and OBD than with POT alone (2.5 mg/kg). However, this compound failed to accelerate gastric emptying in a rat model of PO in combination with a higher dose of morphine (12 mg/kg) even at levels up to 10 mg/kg. (WO 2006/020930).

Intl. Pat. Appl. WO 2006/009645 and WO 2006/009674 describe the use of macrocyclic compounds as ghrelin modulators for use in the treatment of GI disorders. Unexpectedly, and in contrast to other agents that effect GI motility, these macrocyclic compounds have been found to typically require the same dose level or essentially the same dose level to treat the combination condition as was effective for either PO or OBD individually.

These macrocyclic compounds are structurally distinct from other compounds that have been found to interact at the ghrelin receptor as agonists. For example, significant work was devoted to the development of potent and selective GHS with a number of small molecule derivatives now being known as has been recently summarized. (Carpino, P. Exp. Opin. Ther. Patents 2002, 12, 1599-1618.) Specific GHS are described in the following: Intl. Pat. Appl. Publs. WO 89/07110; WO 89/07111; WO 92/07578; WO 93/04081; WO 94/11012; WO 94/13696; WO 94/19367; WO 95/11029; WO 95/13069; WO 95/14666; WO 95/17422; WO 95/17423; WO 95/34311; WO 96/02530; WO 96/15148; WO 96/22996; WO 96/22997; WO 96/24580; WO 96/24587; WO 96/32943; WO 96/33189; WO 96/35713; WO 96/38471; WO 97/00894; WO 97/06803; WO 97/07117; WO 97/09060; WO 97/11697; WO 97/15191; WO 97/15573; WO 97/21730; WO 97/22004; WO 97/22367; WO 97/22620; WO 97/23508; WO 97/24369; WO 97/34604; WO 97/36873; WO 97/38709; WO 97/40023; WO 97/40071; WO 97/41878; WO 97/41879; WO 97/43278; WO 97/44042; WO 97/46252; WO 98/03473; WO 98/10653; WO 98/18815; WO 98/22124; WO 98/46569; WO 98/51687; WO 98/58947; WO 98/58948; WO 98/58949; WO 98/58950; WO 99/08697; WO 99/08699; WO 99/09991; WO 99/36431; WO 99/39730; WO 99/45029; WO 99/58501; WO 99/64456; WO 99/65486, WO 99/65488; WO 00/01726; WO 00/10975; WO 00/48623; WO 00/54729; WO 01/47558; WO 01/92292; WO 01/96300; WO 01/97831; WO 2004/021984; WO 2005/039625; WO 2005/046682; WO 2005/070884; WO 2006/044359; U.S. Pat. No. 3,239,345; U.S. Pat. No. 4,036,979; U.S. Pat. No. 4,411,890; U.S. Pat. No. 5,492,916; U.S. Pat. No. 5,494,919; U.S. Pat. No. 5,559,128; U.S. Pat. No. 5,663,171; U.S. Pat. No. 5,721,250; U.S. Pat. No. 5,721,251; U.S. Pat. No. 5,723,616; U.S. Pat. No. 5,726,319; U.S. Pat. No. 5,767,124; U.S. Pat. No. 5,798,337; U.S. Pat. No. 5,830,433; U.S. Pat. No. 5,919,777; U.S. Pat. No. 6,034,216; U.S. Pat. No. 6,548,501; U.S. Pat. No. 6,559,150; U.S. Pat. No. 6,576,686; U.S. Pat. No. 6,639,076; U.S. Pat. No. 6,686,359; U.S. Pat. No. 6,828,331; U.S. Pat. No. 6,861,409; U.S. Pat. No. 6,919,315; U.S. Pat. No. 7,034,050 and U.S. Pat. Appl. Nos. 2002/0168343; 2003/100494; 2003/130284; 2003/186844; 2005/187237; 2005/233981.

Despite this immense body of work, cyclic compounds have rarely been found to act at the ghrelin receptor. When they have, antagonist activity has been more prevalent. For example, the 14-amino acid compound, vapreotide, an SRIH-14 agonist and somatostatin mimetic, was demonstrated to be a ghrelin antagonist. (Deghenghi R, Papotti M, Ghigo E, et al. Somatostatin octapeptides (lanreotide, octreotide, vapreotide, and their analogs) share the growth hormone-releasing peptide receptor in the human pituitary gland. Endocrine 2001, 14, 29-33.) The binding and antagonist activities of analogues of cortistatin, a cyclic neuropeptide known to bind nonselectively to somatostatin receptors, to the growth hormone secretagogue receptor have been reported. (Intl. Pat. Appl. WO 03/004518; Deghenghi R, Broglio F, Papotti M, et al. Targeting the ghrelin receptor—Orally active GHS and cortistatin analogs. Endocrine 2003, 22, 13-18; Sibilia, V.; Muccioli, G.; Deghenghi, R.; Pagani, F.; DeLuca, V.; Rapetti, D.; Locatelli, V.; Netti, C. Evidence for a role of the GHS-R1a receptor in ghrelin inhibition of gastric acid secretion in the rat. J. Neuroendocrinol. 2006, 18, 122-128.) In particular, one of these analogues, EP-01492 (cortistatin-8) has been advanced into preclinical studies for the treatment of obesity as a ghrelin antagonist. These compounds exhibit an $IC_{50}$ of 24-33 nM. In addition, these cyclic compounds and their derivatives, plus their use with metal binding agents have been described for their ability to be useful for radiodiagnostic or radiotherapeutic use in the treatment of tumors and acromegaly.

Cyclic and linear analogues of growth hormone 177-191 have been studied as treatments for obesity (WO 99/12969), with one particular compound, AOD9604, having entered the clinic for this indication. A compound already studied that is most similar to the molecules of the present invention is the GHS, G-7203 ($EC_{50}$=0.43 nM), the cyclic peptide analogue of the growth hormone releasing peptide, GHRP-2. (Elias, K. A.; Ingle, G. S.; Burnier, J. P.; Hammonds, G.; McDowell, R. S.; Rawson, T. E.; Somers, T. C.; Stanley, M. S.; Cronin, M. J. In vitro characterization of four novel classes of growth hormone-releasing peptide. Endocrinol. 1995, 136, 5694-5699.) However, simplification of this cyclic derivative led to still potent, linear compounds, whereas, for compounds of the invention, linear analogues have been found to be devoid of ghrelin receptor activity.

The macrocyclic compounds of the invention have been shown to possess ghrelin modulating activity, and in particular embodiments, as agonists. However, unlike other agonists of this receptor, the compounds of the invention unexpectedly can stimulate GI motility resulting from multiple GI disorders at the same dose level, or essentially the same dose level, as is efficacious for a single disorder.

SUMMARY OF THE INVENTION

The present invention provides novel conformationally-defined macrocyclic compounds. These compounds can function as modulators, in particular, agonists of the ghrelin (growth hormone secretagogue) receptor (GHS-R1a).

According to aspects of the present invention, the present invention relates to compounds according to formula I, II, III and/or IV:

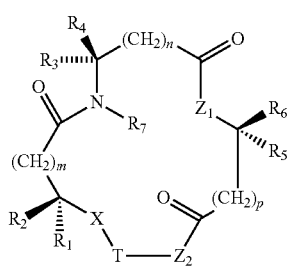

(I)

or a pharmaceutically acceptable salt, hydrate, solvate, optical isomer, enantiomer, diastereomer, racemate or stereochemical mixture thereof,
wherein:
$R_1$ is hydrogen or the side chain of an amino acid, or alternatively $R_1$ and $R_2$ together form a 4-, 5-, 6-, 7- or 8-membered ring, optionally comprising an O, S or N atom in the ring, wherein the ring is optionally substituted with $R_8$ as defined below; or alternatively $R_1$ and $R_9$ together form a 3-, 4-, 5-, 6- or 7-membered ring, optionally comprising an O, S or additional N atom in the ring, wherein the ring is optionally substituted with $R_8$ as defined below;

$R_2$ is hydrogen or the side chain of an amino acid, or alternatively $R_1$ and $R_2$ together form a 4-, 5-, 6-, 7- or 8-membered ring, optionally comprising an O, S or N atom in the ring, wherein the ring is optionally substituted with $R_8$ as defined below; or alternatively $R_2$ and $R_9$ together form a 3-, 4-, 5-, 6- or 7-membered ring, optionally comprising an O, S or additional N atom in the ring, wherein the ring is optionally substituted with $R_8$ as defined below;

$R_3$ is hydrogen or the side chain of an amino acid, or alternatively $R_3$ and $R_4$ together form a 3-, 4-, 5-, 6- or 7-membered ring, optionally comprising an O or S atom in the ring, wherein the ring is optionally substituted with $R_8$ as defined below, or alternatively, $R_3$ and $R_7$ or $R_3$ and $R_{11}$ together form a 4-, 5-, 6-, 7- or 8-membered heterocyclic ring, optionally comprising an O, S or additional N atom in the ring, wherein the ring is optionally substituted with $R_8$ as defined below;

$R_4$ is hydrogen or the side chain of an amino acid, or alternatively $R_4$ and $R_3$ together form a 3-, 4-, 5-, 6- or 7-membered ring, optionally comprising an O or S atom in the ring, wherein the ring is optionally substituted with $R_8$ as defined below, or alternatively $R_4$ and $R_7$ or $R_4$ and $R_{11}$ together form a 4-, 5-, 6-, 7- or 8-membered heterocyclic ring, optionally comprising an O, S or additional N atom in the ring, wherein the ring is optionally substituted with $R_8$ as defined below;

$R_5$ and $R_6$ are each independently hydrogen or the side chain of an amino acid or alternatively $R_5$ and $R_6$ together form a 3-, 4-, 5-, 6- or 7-membered ring, optionally comprising an O, S or N atom in the ring, wherein the ring is optionally substituted with $R_8$ as defined below;

$R_7$ is hydrogen, lower alkyl, substituted lower alkyl, cycloalkyl, substituted cycloalkyl, a heterocyclic group, or a substituted heterocyclic group, or alternatively $R_3$ and $R_7$ or $R_4$ and $R_7$ together form a 4-, 5-, 6-, 7- or 8-membered heterocyclic ring optionally comprising an O, S or additional N atom in the ring, wherein the ring is optionally substituted with $R_8$ as described below;

$R_8$ is substituted for one or more hydrogen atoms on the 3-, 4-, 5-, 6-, 7- or 8-membered ring structure and is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfinyl, sulfonyl and sulfonamido, or, alternatively, $R_8$ is a fused cycloalkyl, a substituted fused cycloalkyl, a fused heterocyclic, a substituted fused heterocyclic, a fused aryl, a substituted fused aryl, a fused heteroaryl or a substituted fused heteroaryl ring when substituted for hydrogen atoms on two adjacent atoms;

X is O, $NR_9$ or $N(R_{10})_2^+$;
  wherein $R_9$ is hydrogen, lower alkyl, substituted lower alkyl, sulfonyl, sulfonamido or amidino and $R_{10}$ is hydrogen, lower alkyl, or substituted lower alkyl, or alternatively $R_9$ and $R_1$ together form a 3-, 4-, 5-, 6- or 7-membered ring, optionally comprising an O, S or additional N atom in the ring, wherein the ring is optionally substituted with $R_8$ as defined above;

$Z_1$ is O or $NR_{11}$,
  wherein $R_{11}$ is hydrogen, lower alkyl, or substituted lower alkyl, or alternatively $R_3$ and $R_{11}$ or $R_4$ and $R_{11}$ together form a 4-, 5-, 6-, 7- or 8-membered heterocyclic ring, optionally comprising an O, S or additional N atom in the ring, wherein the ring is optionally substituted with $R_8$ as defined above;

$Z_2$ is O or $NR_{12}$, wherein $R_{12}$ is hydrogen, lower alkyl, or substituted lower alkyl;

m, n and p are each independently 0, 1 or 2;

T is a bivalent radical of formula V:

$$-U-(CH_2)_d-W-Y-Z-(CH_2)_e-\qquad(V)$$

wherein d and e are each independently 0, 1, 2, 3, 4 or 5; Y and Z are each optionally present; U is —CR$_{21}$R$_{22}$— or —C(=O)— and is bonded to X of formula I; W, Y and Z are each independently selected from the group consisting of —O—, —NR$_{23}$—, —S—, —SO—, —SO$_2$—, —C(=O)—O—, —O—C(=O)—, —C(=O)—NH—, —NH—C(=O)—, —SO$_2$—NH—, —NH—SO$_2$—, —CR$_{24}$R$_{25}$—, —CH=CH— with the configuration Z or E, —C≡C— and the ring structures below:

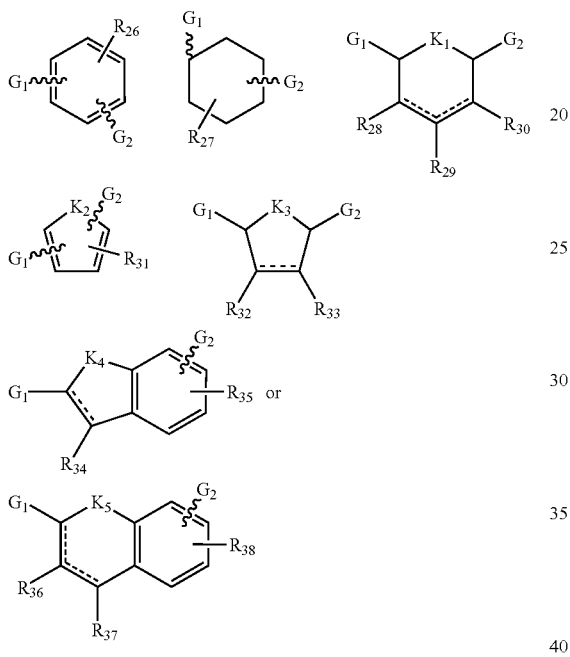

wherein G$_1$ and G$_2$ are each independently a covalent bond or a bivalent radical selected from the group consisting of —O—, —NR$_{39}$—, —S—, —SO—, —SO$_2$—, —C(=O)—, —C(=O)—O—, —O—C(=O)—, —C(=O)NH—, —NH—C(=O)—, —SO$_2$—NH—, —NH—SO$_2$—, —CR$_{40}$R$_{41}$—, —CH=CH— with the configuration Z or E, and —C≡C—; with G$_1$ being bonded closest to the group U; wherein any carbon atom in the rings not otherwise defined, is optionally replaced by N, with the proviso that the ring cannot contain more than four N atoms; K$_1$, K$_2$, K$_3$, K$_4$ and K$_5$ are each independently O, NR$_{42}$ or S, wherein R$_{42}$ is as defined below;

R$_{21}$ and R$_{22}$ are each independently hydrogen, lower alkyl, or substituted lower alkyl, or alternatively R$_{21}$ and R$_{22}$ together form a 3- to 12-membered cyclic ring optionally comprising one or more heteroatoms selected from the group consisting of O, S and N, wherein the ring is optionally substituted with R$_8$ as defined above;

R$_{23}$, R$_{39}$ and R$_{42}$ are each independently hydrogen, alkyl, substituted alkyl, cycloalkyl, substituted cycloalkyl, heterocyclic, substituted heterocyclic, aryl, substituted aryl, heteroaryl, substituted heteroaryl, formyl, acyl, carboxyalkyl, carboxyaryl, amido, amidino, sulfonyl or sulfonamido;

R$_{24}$ and R$_{25}$ are each independently hydrogen, lower alkyl, substituted lower alkyl, R$_{AA}$, wherein R$_{AA}$ is a side chain of an amino acid such as a standard or unusual amino acid, or alternatively R$_{24}$ and R$_{25}$ together form a 3- to 12-membered cyclic ring optionally comprising one or more heteroatoms selected from the group consisting of O, S and N; or alternatively one of R$_{24}$ or R$_{25}$ is hydroxy, alkoxy, aryloxy, amino, mercapto, carbamoyl, amidino, ureido or guanidino while the other is hydrogen, lower alkyl or substituted lower alkyl, except when the carbon to which R$_{24}$ and R$_{25}$ are bonded is also bonded to another heteroatom;

R$_{26}$, R$_{31}$, R$_{35}$ and R$_{38}$ are each optionally present and, when present, are substituted for one or more hydrogen atoms on the indicated ring and each is independently selected from the group consisting of halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro, mercapto, sulfinyl, sulfonyl and sulfonamido;

R$_{27}$ is optionally present and is substituted for one or more hydrogen atoms on the indicated ring and each is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl and sulfonamido;

R$_{28}$, R$_{29}$, R$_{30}$, R$_{32}$, R$_{33}$, R$_{34}$, R$_{36}$ and R$_{37}$ are each optionally present and, when no double bond is present to the carbon atom to which it is bonded in the ring, two groups are optionally present, and when present, is substituted for one hydrogen present in the ring, or when no double bond is present to the carbon atom to which it is bonded in the ring, is substituted for one or both of the two hydrogen atoms present on the ring and each is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl, sulfonamido and, only if a double bond is present to the carbon atom to which it is bonded, halogen; and R$_{40}$ and R$_{41}$ are each independently hydrogen, lower alkyl, substituted lower alkyl, R$_{AA}$ as defined above, or alternatively R$_{40}$ and R$_{41}$ together form a 3- to 12-membered cyclic ring optionally comprising one or more heteroatoms selected from the group consisting of O, S and N wherein the ring is optionally substituted with R$_8$ as defined above, or alternatively one of R$_{40}$ and R$_{41}$ is hydroxy, alkoxy, aryloxy, amino, mercapto, carbamoyl, amidino, ureido or guanidino, while the other is hydrogen, lower alkyl or substituted lower alkyl, except when the carbon to which R$_{40}$ and R$_{41}$ are bonded is also bonded to another heteroatom;

with the proviso that T is not an amino acid residue, dipeptide fragment, tripeptide fragment or higher order peptide fragment comprising standard amino acids;

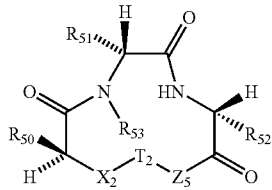

(II)

or a pharmaceutically acceptable salt, hydrate, solvate, optical isomer, enantiomer, diastereomer, racemate or stereochemical mixture thereof,
wherein:
$R_{50}$ is —$(CH_2)_{ss}CH_3$, —$CH(CH_3)(CH_2)_{tt}CH_3$, —$(CH_2)_{uu}CH(CH_3)_2$, —$C(CH_3)_3$, —$(CHR_{55})_{vv}$—$R_{56}$, or —$CH(OR_{57})CH_3$, wherein ss is 1, 2 or 3; tt is 1 or 2; uu is 0, 1 or 2; and vv is 0, 1, 2, 3 or 4; $R_{55}$ is hydrogen or $C_1$-$C_4$ alkyl; $R_{56}$ is amino, hydroxy, alkoxy, cycloalkyl or substituted cycloalkyl; and $R_{57}$ is hydrogen, alkyl, acyl, amino acyl, sulfonyl, carboxyalkyl or carboxyaryl;
$R_{51}$ is hydrogen, $C_1$-$C_4$ alkyl or $C_1$-$C_4$ alkyl substituted with hydroxy or alkoxy;
$R_{52}$ is —$(CHR_{58})_{ww}R_{59}$, wherein ww is 0, 1, 2 or 3; $R_{58}$ is hydrogen, $C_1$-$C_4$ alkyl, amino, hydroxy or alkoxy; $R_{59}$ is aryl, substituted aryl, heteroaryl, substituted heteroaryl, cycloalkyl or substituted cycloalkyl;
$R_{53}$ is hydrogen or $C_1$-$C_4$ alkyl;
$X_2$ is O, $NR_9$ or $N(R_{10})_2^+$;
wherein $R_9$ is hydrogen, lower alkyl, substituted lower alkyl, sulfonyl, sulfonamido or amidino and $R_{10}$ is hydrogen, lower alkyl, or substituted lower alkyl;
$Z_5$ is O or $NR_{12}$, wherein $R_{12}$ is hydrogen, lower alkyl, or substituted lower alkyl; and
$T_2$ is a bivalent radical of formula VI:

—$U_a$—$(CH_2)_d$—$W_a$—$Y_a$—$Z_a$—$(CH_2)_e$— (VI)

wherein d and e are independently 0, 1, 2, 3, 4 or 5; $Y_a$ and $Z_a$ are each optionally present; $U_a$ is —$CR_{60}R_{61}$— or —$C(=O)$— and is bonded to $X_2$ of formula II, wherein $R_{60}$ and $R_{61}$ are each independently hydrogen, lower alkyl, or substituted lower alkyl, or alternatively $R_{21}$ and $R_{22}$ together form a 3- to 12-membered cyclic ring optionally comprising one or more heteroatoms selected from the group consisting of O, S and N, wherein the ring is optionally substituted with $R_8$ as defined above; $W_a$, $Y_a$ and $Z_a$ are each independently selected from the group consisting of: —O—, —$NR_{62}$—, —S—, —SO—, —$SO_2$—, —C(=O)—O—, —O—C(=O)—, —C(=O)—NH—, —NH—C(=O)—, —$SO_2$—NH—, —NH—$SO_2$—, —$CR_{63}R_{64}$—, —CH=CH— with the configuration Z or E, —C≡C—, and the ring structures depicted below:

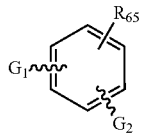 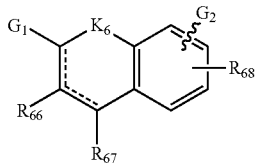

-continued

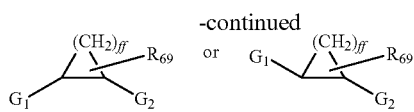

wherein $G_1$ and $G_2$ are as defined above, and wherein any carbon atom in the ring is optionally replaced by N, with the proviso that the aromatic ring cannot contain more than four N atoms and the cycloalkyl ring cannot contain more than two N atoms;
$R_{62}$ is hydrogen, alkyl, substituted alkyl, cycloalkyl, substituted cycloalkyl, a heterocyclic group, a substituted heterocyclic group, aryl, substituted aryl, heteroaryl, substituted heteroaryl, formyl, acyl, carboxyalkyl, carboxyaryl, amido, amidino, sulfonyl or sulfonamido;
$R_{63}$ and $R_{64}$ are each independently hydrogen, lower alkyl, substituted lower alkyl or $R_{AA}$; or alternatively $R_{63}$ and $R_{64}$ together form a 3- to 12-membered cyclic ring optionally comprising one or more heteroatoms selected from the group consisting of O, S and N; or alternatively one of $R_{63}$ and $R_{64}$ is hydroxy, alkoxy, aryloxy, amino, mercapto, carbamoyl, amidino, ureido or guanidino, while the other is hydrogen, lower alkyl or substituted lower alkyl, except when the carbon to which $R_{63}$ and $R_{64}$ are bonded is also bonded to another heteroatom; and $R_{AA}$ indicates the side chain of an amino acid such as a standard or unusual amino acid;
$R_{65}$ and $R_{68}$ are each optionally present, and, when present are substituted for one or more hydrogen atoms on the ring and each is independently halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro, mercapto, sulfinyl, sulfonyl or sulfonamido;
$R_{66}$ and $R_{67}$ are each optionally present, and when no double bond is present to the carbon atom to which it is bonded in the ring, two groups are optionally present, and, when present, each is substituted for one hydrogen present in the ring, or when no double bond is present to the carbon atom to which it is bonded in the ring, is substituted for one or both of the two hydrogen atoms present on the ring and each is independently alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl, sulfonamido and, only if a double bond is present to the carbon atom to which it is bonded, halogen;
$R_{69}$ is optionally present, and when present is substituted for one or more hydrogen atoms on the ring and each is independently alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl or sulfonamido;

$K_6$ is O or S; and ff is 1, 2, 3, 4 or 5;

with the proviso that $T_2$ is not an amino acid residue, dipeptide fragment, tripeptide fragment or higher order peptide fragment comprising standard amino acids;

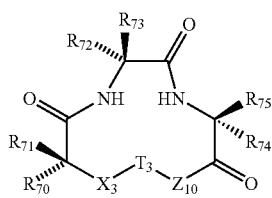

(III)

or a pharmaceutically acceptable salt, hydrate, solvate, optical isomer, enantiomer, diastereomer, racemate or stereochemical mixture thereof, wherein:

$R_{70}$ is hydrogen, $C_1$-$C_4$ alkyl or alternatively $R_{70}$ and $R_{71}$ together form a 4-, 5-, 6-, 7- or 8-membered ring, optionally comprising an O, N or S atom in the ring, wherein the ring is optionally substituted with $R_{8a}$ as defined below;

$R_{71}$ is hydrogen, $-(CH_2)_{aa}CH_3$, $-CH(CH_3)(CH_2)_{bb}CH_3$, $-(CH_2)_{cc}CH(CH_3)_2$, $-(CH_2)_{dd}-R_{76}$ or $-CH(OR_{77})CH_3$ or, alternatively $R_{71}$ and $R_{70}$ together form a 4-, 5-, 6-, 7- or 8-membered ring, optionally comprising an O, N or S atom in the ring, wherein the ring is optionally substituted with $R_{8a}$ as defined below; wherein aa is 0, 1, 2, 3, 4 or 5; bb is 1, 2 or 3; cc is 0, 1, 2 or 3; and dd is 0, 1, 2, 3 or 4; $R_{76}$ is aryl, substituted aryl, heteroaryl, substituted heteroaryl, cycloalkyl or substituted cycloalkyl; $R_{77}$ is hydrogen, alkyl, acyl, amino acyl, sulfonyl, carboxyalkyl or carboxyaryl;

$R_{72}$ is $C_1$-$C_4$ alkyl; or alternatively $R_{72}$ and $R_{73}$ together form a 3-, 4-, 5-, 6- or 7-membered ring, optionally comprising an O or S atom in the ring, wherein the ring is optionally substituted with $R_{8b}$ as defined below;

$R_{73}$ is hydrogen, or alternatively $R_{73}$ and $R_{72}$ together form a 3-, 4-, 5-, 6- or 7-membered ring, optionally comprising an O, S or N atom in the ring, wherein the ring is optionally substituted with $R_{8b}$ as defined below;

$R_{74}$ is hydrogen or $C_1$-$C_4$ alkyl or alternatively $R_{74}$ and $R_{75}$ together form a 3-, 4-, 5-, 6- or 7-membered ring, optionally comprising an O, N or S atom in the ring, wherein the ring is optionally substituted with $R_{8c}$ as defined below;

$R_{75}$ is $-(CHR_{78})R_{79}$ or alternatively $R_{75}$ and $R_{74}$ together form a 3-, 4-, 5-, 6- or 7-membered ring, optionally comprising an O, N or S atom in the ring, wherein the ring is optionally substituted with $R_{8c}$ as defined below; wherein $R_{78}$ is hydrogen, $C_1$-$C_4$ alkyl, amino, hydroxy or alkoxy, and $R_{79}$ is selected from the group consisting of the following structures:

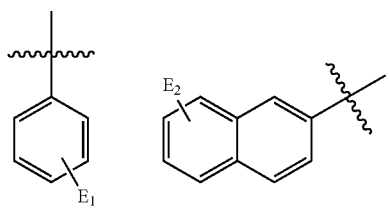

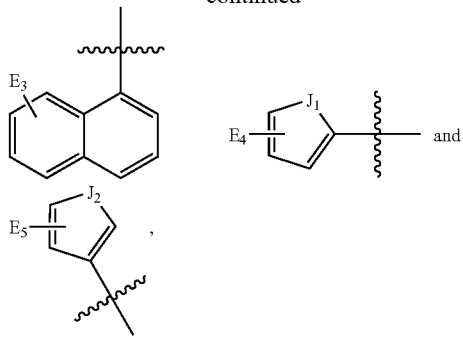

wherein $E_1$, $E_2$, $E_3$, $E_4$ and $E_5$ are each optionally present and when present are each independently selected from the group consisting of halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, cyano, sulfinyl, sulfonyl and sulfonamido, and represent substitution at one or more available positions on the monocyclic or bicyclic aromatic ring, wherein said substitution is made with the same or different selected group member, and $J_1$ and $J_2$ are each independently O or S;

$R_{8a}$, $R_{8b}$ and $R_{8c}$ are each independently substituted for one or more hydrogen atoms on the 3-, 4-, 5-, 6-, 7- or 8-membered ring structure and are independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfinyl, sulfonyl and sulfonamido, or, alternatively, $R_{8a}$, $R_{8b}$ and $R_{8c}$ are each independently a fused cycloalkyl, a substituted fused cycloalkyl, a fused heterocyclic, a substituted fused heterocyclic, a fused aryl, a substituted fused aryl, a fused heteroaryl or a substituted fused heteroaryl ring when substituted for hydrogen atoms on two adjacent atoms;

$X_3$ is O, $NR_9$ or $N(R_{10})_2^+$;

wherein $R_9$ is hydrogen, lower alkyl, substituted lower alkyl, sulfonyl, sulfonamido or amidino and $R_{10}$ is hydrogen, lower alkyl, or substituted lower alkyl;

$Z_{10}$ is O or $NR_{12}$, wherein $R_{12}$ is hydrogen, lower alkyl, or substituted lower alkyl; and $T_3$ is the same as defined for $T_2$ with the exception that $U_a$ is bonded to $X_3$ of formula III; or

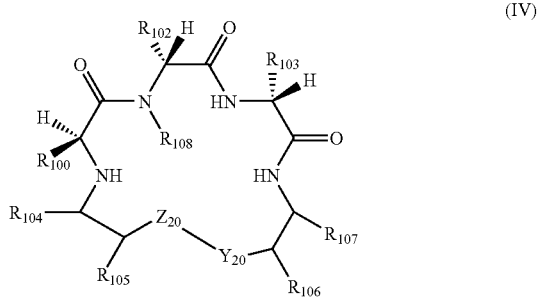

(IV)

or a pharmaceutically acceptable salt, hydrate, solvate, optical isomer, enantiomer, diastereomer, racemate or stereochemical mixture thereof, wherein:
R$_{100}$ is cycloalkyl;
R$_{102}$ is selected from the group consisting of lower alkyl and substituted lower alkyl;
R$_{103}$ is selected from the group consisting of alkyl and alkyl substituted with aryl;
R$_{104}$, R$_{105}$, R$_{106}$, and R$_{107}$ are independently selected from the group consisting of hydrogen, lower alkyl and substituted lower alkyl;
R$_{108}$ is selected from the group consisting of hydrogen and lower alkyl;
Y$_{20}$ is selected from the group consisting of O and CR$_{9a}$R$_{9b}$; wherein R$_{9a}$ and R$_{9b}$ are independently selected from the group consisting of hydrogen and lower alkyl;
Z$_{20}$ is selected from the group consisting of:

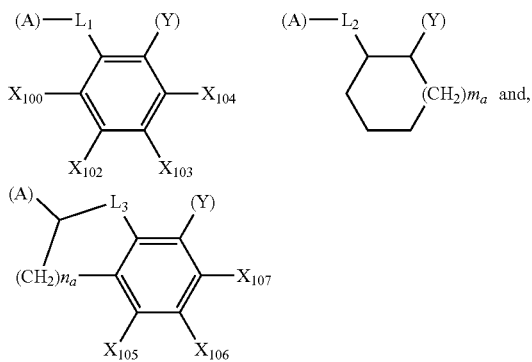

wherein (A) and (Y) indicate the bonds of Z$_{20}$ to CHR$_{105}$ and Y$_{20}$ of formula IV, respectively;
L$_1$, L$_2$ and L$_3$ are independently selected from the group consisting of O, and CR$_{10a}$R$_{10b}$; wherein R$_{10a}$ and R$_{10b}$ are independently selected from the group consisting of hydrogen and lower alkyl;
X$_{100}$, X$_{102}$, X$_{103}$, X$_{104}$, X$_{105}$, X$_{106}$ and X$_{107}$ are independently selected from the group consisting of hydrogen, halogen, trifluoromethyl and lower alkyl; and
m$_a$ is 0 or 1; and n$_a$ is 1 or 2.

Aspects of the present invention further provide methods of stimulating gastrointestinal motility and/or treating a gastrointestinal disorder comprising administering to a subject in need thereof an effective amount of an agonist for a mammalian ghrelin receptor. In still other embodiments, the agonist is a compound of formula I, II, III and/or IV.

Aspects of the present invention further relate to methods of preventing and/or treating disorders described herein, in particular, gastrointestinal disorders, including post-operative ileus, gastroparesis, such as idiopathic, diabetic and post-surgical gastroparesis, opioid-induced bowel dysfunction, chronic intestinal pseudo-obstruction, short bowel syndrome, emesis such as caused by cancer chemotherapy, constipation such as associated with the hypomotility phase of irritable bowel syndrome (IBS), delayed gastric emptying associated with wasting conditions, gastroesophageal reflux disease (GERD), gastric ulcers, Crohn's disease, gastrointestinal disorders characterized by dysmotility and other diseases and disorders of the gastrointestinal tract.

A further aspect of the invention relates to methods for the simultaneous treatment of multiple gastrointestinal disorders such as those listed above, in particular postoperative ileus and opioid-induced bowel dysfunction as well as post-surgical gastropareis and opioid-induced bowel dysfunction.

Another aspect of the invention relates to methods for the simultaneous treatment of multiple gastrointestinal disorders such as those listed above that occur concurrently.

Another aspect of the invention relates to methods for the simultaneous treatment of multiple gastrointestinal disorders such as those listed above that occur sequentially.

The present invention also relates to compounds of formula I, II, III and/or IV used for the preparation of a medicament for prevention and/or treatment of the disorders described herein. Additionally, the present invention provides co-administration with, administration prior to (including prior to initial therapy), and administration after administration of an opioid or opioid-like compound to stimulate gastrointestinal motility as well as for the prevention and treatment of opioid-induced bowel dysfunction.

The foregoing and other aspects of the present invention are explained in greater detail in the specification set forth below.

DETAILED DESCRIPTION

Figure 1:
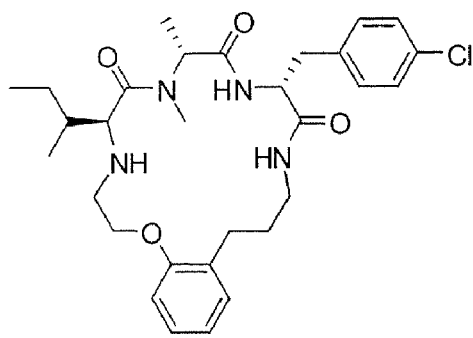
FIG. 1 shows the chemical structures for two exemplary compounds of the present invention.
Figure 1:
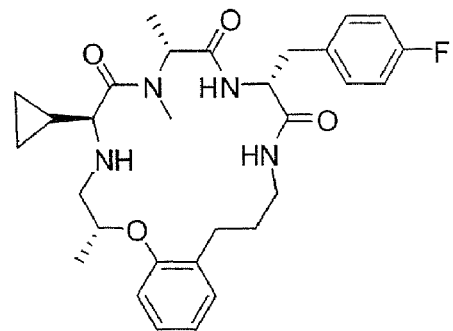

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Additionally, as used herein, the term "and/or" includes any and all combinations of one or more of the associated listed items and may be abbreviated as "/".

Unless otherwise defined, all technical and scientific terms used herein have the same meaning as commonly understood by one of ordinary skill in the art to which this invention belongs.

All publications, U.S. patent applications, U.S. patents and other references cited herein are incorporated by reference in their entireties.

The term "alkyl" refers to straight or branched chain saturated or partially unsaturated hydrocarbon groups having from 1 to 20 carbon atoms, in some instances 1 to 8 carbon atoms. The term "lower alkyl" refers to alkyl groups containing 1 to 6 carbon atoms. Examples of alkyl groups include, but are not limited to, methyl, ethyl, isopropyl, tert-butyl, 3-hexenyl, and 2-butynyl. By "unsaturated" is meant the presence of 1, 2 or 3 double or triple bonds, or a combination of the two. Such alkyl groups may also be optionally substituted as described below.

When a subscript is used with reference to an alkyl or other hydrocarbon group defined herein, the subscript refers to the number of carbon atoms that the group may contain. For example, $C_2$-$C_4$ alkyl indicates an alkyl group with 2, 3 or 4 carbon atoms.

The term "cycloalkyl" refers to saturated or partially unsaturated cyclic hydrocarbon groups having from 3 to 15 carbon atoms in the ring, in some instances 3 to 7, and to alkyl groups containing said cyclic hydrocarbon groups. Examples of cycloalkyl groups include, but are not limited to, cyclopropyl, cyclopropylmethyl, cyclopentyl, 2-(cyclohexyl)ethyl, cycloheptyl, and cyclohexenyl. Cycloalkyl as defined herein also includes groups with multiple carbon rings, each of which may be saturated or partially unsaturated, for example decalinyl, [2.2.1]-bicycloheptanyl or adamantanyl. All such cycloalkyl groups may also be optionally substituted as described below.

The term "aromatic" refers to an unsaturated cyclic hydrocarbon group having a conjugated pi electron system that contains 4n+2 electrons where n is an integer greater than or equal to 1. Aromatic molecules are typically stable and are depicted as a planar ring of atoms with resonance structures that consist of alternating double and single bonds, for example benzene or naphthalene.

The term "aryl" refers to an aromatic group in a single or fused carbocyclic ring system having from 6 to 15 ring atoms, in some instances 6 to 10, and to alkyl groups containing said aromatic groups. Examples of aryl groups include, but are not limited to, phenyl, 1-naphthyl, 2-naphthyl and benzyl. Aryl as defined herein also includes groups with multiple aryl rings which may be fused, as in naphthyl and anthracenyl, or unfused, as in biphenyl and terphenyl. Aryl also refers to bicyclic or tricyclic carbon rings, where one of the rings is aromatic and the others of which may be saturated, partially unsaturated or aromatic, for example, indanyl or tetrahydronaphthyl(tetralinyl). All such aryl groups may also be optionally substituted as described below.

The term "heterocycle" or "heterocyclic" refers to saturated or partially unsaturated monocyclic, bicyclic or tricyclic groups having from 3 to 15 atoms, in some instances 3 to 7, with at least one heteroatom in at least one of the rings, said heteroatom being selected from O, S or N. Each ring of the heterocyclic group can contain one or two O atoms, one or two S atoms, one to four N atoms, provided that the total number of heteroatoms in each ring is four or less and each ring contains at least one carbon atom. The fused rings completing the bicyclic or tricyclic heterocyclic groups may contain only carbon atoms and may be saturated or partially unsaturated. The N and S atoms may optionally be oxidized and the N atoms may optionally be quaternized. Heterocyclic also refers to alkyl groups containing said monocyclic, bicyclic or tricyclic heterocyclic groups. Examples of heterocyclic rings include, but are not limited to, 2- or 3-piperidinyl, 2- or 3-piperazinyl, 2- or 3-morpholinyl. All such heterocyclic groups may also be optionally substituted as described below The term "heteroaryl" refers to an aromatic group in a single or fused ring system having from 5 to 15 ring atoms, in some instances 5 to 10, which have at least one heteroatom in at least one of the rings, said heteroatom being selected from O, S or N. Each ring of the heteroaryl group can contain one or two O atoms, one or two S atoms, one to four N atoms, provided that the total number of heteroatoms in each ring is four or less and each ring contains at least one carbon atom. The fused rings completing the bicyclic or tricyclic groups may contain only carbon atoms and may be saturated, partially unsaturated or aromatic. In structures where the lone pair of electrons of a nitrogen atom is not involved in completing the aromatic pi electron system, the N atoms may optionally be quaternized or oxidized to the N-oxide. Heteroaryl also refers to alkyl groups containing said cyclic groups. Examples of monocyclic heteroaryl groups include, but are not limited to pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, benzopyranyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to carbazolyl, benzindolyl, phenanthrollinyl, acridinyl, phenanthridinyl, and xanthenyl. All such heteroaryl groups may also be optionally substituted as described below.

The term "hydroxy" refers to the group —OH.

The term "alkoxy" refers to the group —OR$_a$, wherein R$_a$ is alkyl, cycloalkyl or heterocyclic. Examples include, but are not limited to methoxy, ethoxy, tert-butoxy, cyclohexyloxy and tetrahydropyranyloxy.

The term "aryloxy" refers to the group —OR$_b$ wherein R$_b$ is aryl or heteroaryl. Examples include, but are not limited to phenoxy, benzyloxy and 2-naphthyloxy.

The term "acyl" refers to the group —C(=O)—R$_c$ wherein R$_c$ is alkyl, cycloalkyl, heterocyclic, aryl or heteroaryl. Examples include, but are not limited to, acetyl, benzoyl and furoyl.

The term "amino acyl" indicates an acyl group that is derived from an amino acid.

The term "amino" refers to an —NR$_d$R$_e$ group wherein R$_d$ and R$_e$ are independently selected from the group consisting of hydrogen, alkyl, cycloalkyl, heterocyclic, aryl and heteroaryl. Alternatively, R$_d$ and R$_e$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amido" refers to the group —C(=O)—NR$_f$R$_g$ wherein R$_f$ and R$_g$ are independently selected from the group consisting of hydrogen, alkyl, cycloalkyl, heterocyclic, aryl and heteroaryl. Alternatively, $R_f$ and $R_g$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "amidino" refers to the group —C(=NR$_h$)NR$_i$R$_j$ wherein R$_h$ is selected from the group consisting of hydrogen, alkyl, cycloalkyl, heterocyclic, aryl and heteroaryl; and R$_i$ and R$_j$ are independently selected from the group consisting of hydrogen, alkyl, cycloalkyl, heterocyclic, aryl and heteroaryl. Alternatively, R$_i$ and R$_j$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carboxy" refers to the group —CO$_2$H.

The term "carboxyalkyl" refers to the group —CO$_2$R$_k$, wherein R$_k$ is alkyl, cycloalkyl or heterocyclic.

The term "carboxyaryl" refers to the group —CO$_2$R$_m$, wherein R$_m$ is aryl or heteroaryl.

The term "cyano" refers to the group —CN.

The term "formyl" refers to the group —C(=O)H, also denoted —CHO.

The term "halo," "halogen" or "halide" refers to fluoro, fluorine or fluoride, chloro, chlorine or chloride, bromo, bromine or bromide, and iodo, iodine or iodide, respectively.

The term "oxo" refers to the bivalent group =O, which is substituted in place of two hydrogen atoms on the same carbon to form a carbonyl group.

The term "mercapto" refers to the group —SR$_n$ wherein R$_n$ is hydrogen, alkyl, cycloalkyl, heterocyclic, aryl or heteroaryl.

The term "nitro" refers to the group —NO$_2$.

The term "trifluoromethyl" refers to the group —CF$_3$.

The term "sulfinyl" refers to the group —S(=O)R$_p$ wherein R$_p$ is alkyl, cycloalkyl, heterocyclic, aryl or heteroaryl.

The term "sulfonyl" refers to the group —S(=O)$_2$—R$_{q1}$ wherein R$_{q1}$ is alkyl, cycloalkyl, heterocyclic, aryl or heteroaryl.

The term "aminosulfonyl" refers to the group —NR$_{q2}$—S(=O)$_2$—R$_{q3}$ wherein R$_{q2}$ is hydrogen, alkyl, cycloalkyl, heterocyclic, aryl or heteroaryl; and R$_{q3}$ is alkyl, cycloalkyl, heterocyclic, aryl or heteroaryl.

The term "sulfonamido" refers to the group —S(=O)$_2$—NR$_r$R$^s$ wherein R$_r$ and R$_s$ are independently selected from the group consisting of hydrogen, alkyl, cycloalkyl, heterocyclic, aryl or heteroaryl. Alternatively, R$_r$ and R$_s$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "carbamoyl" refers to a group of the formula —N(R$_t$)—C(=O)—OR$_u$ wherein R$_t$ is selected from hydrogen, alkyl, cycloalkyl, heterocyclic, aryl or heteroaryl; and R$_u$ is selected from alkyl, cycloalkyl, heterocyclic, aryl or heteroaryl.

The term "guanidino" refers to a group of the formula —N(R$_v$)—C(=NR$_w$)—NR$_x$R$_y$ wherein R$^v$, R$_w$, R$_x$ and R$_y$ are independently selected from hydrogen, alkyl, cycloalkyl, heterocyclic, aryl or heteroaryl. Alternatively, R$_x$ and R$_y$ together form a heterocyclic ring or 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "ureido" refers to a group of the formula —N(R$_z$)—C(=O)—NR$_{aa}$R$_{bb}$ wherein R$_z$, R$_{aa}$ and R$_{bb}$ are independently selected from hydrogen, alkyl, cycloalkyl, heterocyclic, aryl or heteroaryl. Alternatively, R$_{aa}$ and R$_{bb}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

The term "substituted" when used with the terms alkyl, cycloalkyl, heterocyclic, aryl and heteroaryl refers to an alkyl, cycloalkyl, heterocyclic, aryl or heteroaryl group having one or more of the hydrogen atoms of the group replaced by substituents independently selected from unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, halo, oxo, mercapto, sulfinyl, sulfonyl, sulfonamido, amidino, carbamoyl, guanidino, ureido and groups of the formulas —NR$_{cc}$C(=O)R$_{dd}$, —NR$_{ee}$C(=NR$_{ff}$)R$_{gg}$, —OC(=O)NR$_{hh}$R$_{ii}$, —OC(=O)R$_{jj}$, —OC(=O)OR$_{kk}$, —NR$_{mm}$SO$_2$R$_{nn}$, or —NR$_{pp}$SO$_2$N$_{qq}$R$_{rr}$ wherein R$_{cc}$, R$_{dd}$, R$_{ee}$, R$_{ff}$, R$_{gg}$, R$_{hh}$, R$_{ii}$, R$_{jj}$, R$_{mm}$, R$_{pp}$, R$_{qq}$ and R$_{rr}$ are independently selected from hydrogen, unsubstituted alkyl, unsubstituted cycloalkyl, unsubstituted heterocyclic, unsubstituted aryl or unsubstituted heteroaryl; and wherein R$_{kk}$ and R$_{nn}$ are independently selected from unsubstituted alkyl, unsubstituted cycloalkyl, unsubstituted heterocyclic, unsubstituted aryl or unsubstituted heteroaryl. Alternatively, R$_{gg}$ and R$_{hh}$, R$_{jj}$ and R$_{kk}$ or R$_{pp}$ and R$_{qq}$ together form a heterocyclic ring of 3 to 8 members, optionally substituted with unsubstituted alkyl, unsubstituted cycloalkyl, unsubstituted heterocyclic, unsubstituted aryl, unsubstituted heteroaryl, hydroxy, alkoxy, aryloxy, acyl, amino, amido, carboxy, carboxyalkyl, carboxyaryl, mercapto, sulfinyl, sulfonyl, sulfonamido, amidino, carbamoyl, guanidino or ureido, and optionally containing one to three additional heteroatoms selected from O, S or N. In addition, the term "substituted" for aryl and heteroaryl groups includes as an option having one of the hydrogen atoms of the group replaced by cyano, nitro or trifluoromethyl.

A substitution is made provided that any atom's normal valency is not exceeded and that the substitution results in a stable compound. Generally, when a substituted form of a group is present, such substituted group is preferably not further substituted or, if substituted, the substituent comprises only a limited number of substituted groups, in some instances 1, 2, 3 or 4 such substituents.

When any variable occurs more than one time in any constituent or in any formula herein, its definition on each occurrence is independent of its definition at every other occurrence. Also, combinations of substituents and/or variables are permissible only if such combinations result in stable compounds.

A "stable compound" or "stable structure" refers to a compound that is sufficiently robust to survive isolation to a useful degree of purity and formulation into an efficacious therapeutic agent.

The term "amino acid" refers to the common natural (genetically encoded) or synthetic amino acids and common derivatives thereof, known to those skilled in the art. When applied to amino acids, "standard" or "proteinogenic" refers to the genetically encoded 20 amino acids in their natural configuration. Similarly, when applied to amino acids, "unnatural" or "unusual" refers to the wide selection of non-natural, rare or synthetic amino acids such as those described by Hunt, S. in Chemistry and Biochemistry of the Amino Acids, Barrett, G. C., Ed., Chapman and Hall: New York, 1985.

The term "residue" with reference to an amino acid or amino acid derivative refers to a group of the formula:

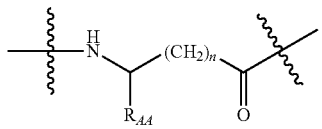

wherein $R_{AA}$ is an amino acid side chain, and n=0, 1 or 2 in this instance.

The term "fragment" with respect to a dipeptide, tripeptide or higher order peptide derivative indicates a group that contains two, three or more, respectively, amino acid residues.

The term "amino acid side chain" refers to any side chain from a standard or unnatural amino acid, and is denoted $R_{AA}$. For example, the side chain of alanine is methyl, the side chain of valine is isopropyl and the side chain of tryptophan is 3-indolylmethyl.

The term "agonist" refers to a compound that duplicates at least some of the effect of the endogenous ligand of a protein, receptor, enzyme or the like.

The term "antagonist" refers to a compound that inhibits at least some of the effect of the endogenous ligand of a protein, receptor, enzyme or the like.

The term "growth hormone secretagogue" (GHS) refers to any exogenously administered compound or agent that directly or indirectly stimulates or increases the endogenous release of growth hormone, growth hormone-releasing hormone, or somatostatin in an animal, in particular, a human. A GHS may be peptidic or non-peptidic in nature, in some instances, with an agent that can be administered orally. In some instances, the agent can induce a pulsatile response.

The term "modulator" refers to a compound that imparts an effect on a biological or chemical process or mechanism. For example, a modulator may increase, facilitate, upregulate, activate, inhibit, decrease, block, prevent, delay, desensitize, deactivate, down regulate, or the like, a biological or chemical process or mechanism. Accordingly, a modulator can be an "agonist" or an "antagonist." Exemplary biological processes or mechanisms affected by a modulator include, but are not limited to, receptor binding and hormone release or secretion. Exemplary chemical processes or mechanisms affected by a modulator include, but are not limited to, catalysis and hydrolysis.

The term "opioid" as used herein refers to compounds that exhibit opium or morphine-like properties. These compounds may interact with stereospecific and saturable binding sites in the brain and other tissues. Pharmacological properties may include drowsiness, respiratory depression, changes in mood and mental clouding without a resulting loss of consciousness. The term "opioid-like" as used herein refers to compounds that are similar in structure and/or pharmacological profile to known opioid compounds. Examples of opioid and opioid-like compounds, include but are not limited to, alfentanil, allylprodine, alphaprodine, anileridine, asimadoline, benzylmorphine, bezitramide, bremazocine, buprenorphine, butorphanol, clonitazene, codeine, cyclazocine, desomorphine, dextromoramide, dextromethorphan, dezocine, diampromide, diamorphone, dihydrocodeine, dihydromorphine, dimenoxadol, dimepheptanol, dimethylthiambutene, dioxaphetyl butyrate, diphenoxylate, dipipanone, eptazocine, ethoheptazine, ethylmethylthiambutene, ethylmorphine, etonitazene, fedotozine, fentanyl, funaltrexamine, heroin (diacetylmorphine), hydrocodone, hydromorphone, hydroxypethidine, isomethadone, ketobemidone, levallorphan, levomethadyl acetate, levorphanol, levophenacylmorphan, lofentanil, loperamide, meperidine (pethidine), meptazinol, metazocine, methadone, metopon, morphine, morphine-6-glucoronide, morphinan, myrophine, narceine, nicomorphine, norlevorphanol, normethadone, naltrindole, nalorphine, naloxone, nalbuphine, nalmefene, naltrexone, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene, remifentanyl, sufentanil, tilidine, tramadol, trimebutine, and derivatives and analogs thereof.

The term "variant" when applied to a receptor is meant to include dimers, trimers, tetramers, pentamers and other biological complexes containing multiple components. These components can be the same or different.

The term "peptide" refers to a chemical compound comprised of two or more amino acids covalently bonded together.

The term "peptidomimetic" refers to a chemical compound designed to mimic a peptide, but which contains structural differences through the addition or replacement of one of more functional groups of the peptide in order to modulate its activity or other properties, such as solubility, metabolic stability, oral bioavailability, lipophilicity, permeability, etc. This can include replacement of the peptide bond, side chain modifications, truncations, additions of functional groups, etc. When the chemical structure is not derived from the peptide, but mimics its activity, it is often referred to as a "non-peptide peptidomimetic."

The term "peptide bond" refers to the amide [—C(=O)—NH—] functionality with which individual amino acids are typically covalently bonded to each other in a peptide.

The term "protecting group" refers to any chemical compound that may be used to prevent a potentially reactive functional group, such as an amine, a hydroxyl or a carboxyl, on a molecule from undergoing a chemical reaction while chemical change occurs elsewhere in the molecule. A number of such protecting groups are known to those skilled in the art and examples can be found in "Protective Groups in Organic Synthesis," Theodora W. Greene and Peter G. Wuts, editors, John Wiley & Sons, New York, 3$^{rd}$ edition, 1999 [ISBN 0471160199]. Examples of amino protecting groups include, but are not limited to, phthalimido, trichloroacetyl, benzyloxycarbonyl, tert-butoxycarbonyl, and adamantyloxycarbonyl. In some embodiments, amino protecting groups are carbamate amino protecting groups, which are defined as an amino protecting group that when bound to an amino group forms a carbamate. In other embodiments, amino carbamate protecting groups are allyloxycarbonyl (Alloc), benzyloxycarbonyl (Cbz), 9-fluorenylmethoxycarbonyl (Fmoc), tert-butoxycarbonyl (Boc) and α,α-dimethyl-3,5-dimethoxybenzyloxycarbonyl (Ddz). For a recent discussion of newer nitrogen protecting groups: Theodoridis, G. Tetrahedron 2000, 56, 2339-2358. Examples of hydroxyl protecting groups include, but are not limited to, acetyl, tert-butyldimethylsilyl (TBDMS), trityl (Trt), tert-butyl, and tetrahydropyranyl (THP). Examples of carboxyl protecting groups include, but are not limited to methyl ester, tert-butyl ester, benzyl ester, trimethylsilylethyl ester, and 2,2,2-trichloroethyl ester.

The term "solid phase chemistry" refers to the conduct of chemical reactions where one component of the reaction is covalently bonded to a polymeric material (solid support as defined below). Reaction methods for performing chemistry on solid phase have become more widely known and established outside the traditional fields of peptide and oligonucleotide chemistry.

The term "solid support," "solid phase" or "resin" refers to a mechanically and chemically stable polymeric matrix utilized to conduct solid phase chemistry. This is denoted by "Resin," "P-" or the following symbol:

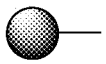

Examples of appropriate polymer materials include, but are not limited to, polystyrene, polyethylene, polyethylene glycol, polyethylene glycol grafted or covalently bonded to polystyrene (also termed PEG-polystyrene, TentaGel™, Rapp, W.; Zhang, L.; Bayer, E. In Innovations and Persepctives in Solid Phase Synthesis. Peptides, Polypeptides and Oligonucleotides; Epton, R., Ed.; SPCC Ltd.: Birmingham, UK; p 205), polyacrylate (CLEAR™), polyacrylamide, polyurethane, PEGA [polyethyleneglycol poly(N,N-dimethylacrylamide) co-polymer, Meldal, M. Tetrahedron Lett. 1992, 33, 3077-3080], cellulose, etc. These materials can optionally contain additional chemical agents to form cross-linked bonds to mechanically stabilize the structure, for example polystyrene cross-linked with divinylbenezene (DVB, usually 0.1-5%, preferably 0.5-2%). This solid support can include as non-limiting examples aminomethyl polystyrene, hydroxymethyl polystyrene, benzhydrylamine polystyrene (BHA), methylbenzhydrylamine (MBHA) polystyrene, and other polymeric backbones containing free chemical functional groups, most typically, —NH$_2$ or —OH, for further derivatization or reaction. The term is also meant to include "Ultraresins" with a high proportion ("loading") of these functional groups such as those prepared from polyethyleneimines and cross-linking molecules (Barth, M.; Rademann, J. J. Comb. Chem. 2004, 6, 340-349). At the conclusion of the synthesis, resins are typically discarded, although they have been shown to be able to be reused such as in Frechet, J. M. J.; Haque, K. E. Tetrahedron Lett. 1975, 16, 3055.

In general, the materials used as resins are insoluble polymers, but certain polymers have differential solubility depending on solvent and can also be employed for solid phase chemistry. For example, polyethylene glycol can be utilized in this manner since it is soluble in many organic solvents in which chemical reactions can be conducted, but it is insoluble in others, such as diethyl ether. Hence, reactions can be conducted homogeneously in solution, then the product on the polymer precipitated through the addition of diethyl ether and processed as a solid. This has been termed "liquid-phase" chemistry.

The term "linker" when used in reference to solid phase chemistry refers to a chemical group that is bonded covalently to a solid support and is attached between the support and the substrate typically in order to permit the release (cleavage) of the substrate from the solid support. However, it can also be used to impart stability to the bond to the solid support or merely as a spacer element. Many solid supports are available commercially with linkers already attached.

Abbreviations used for amino acids and designation of peptides follow the rules of the IUPAC-IUB Commission of Biochemical Nomenclature in J. Biol. Chem. 1972, 247, 977-983. This document has been updated: Biochem. J., 1984, 219, 345-373; Etir. J. Biochem., 1984, 138, 9-37; 1985, 152, 1; Internat. J. Pept. Prot. Res., 1984, 24, following p 84; J. Biol. Chem., 1985, 260, 14-42; Pure Appl. Chem., 1984, 56, 595-624; Amino Acids and Peptides, 1985, 16, 387-410; and in Biochemical Nomenclature and Related Documents, 2nd edition, Portland Press, 1992, pp 39-67. Extensions to the rules were published in the JCBN/NC-IUB Newsletter 1985, 1986, 1989; see Biochemical Nomenclature and Related Documents, 2nd edition, Portland Press, 1992, pp 68-69.

The term "effective amount" or "effective" is intended to designate a dose that causes a relief of symptoms of a disease or disorder as noted through clinical testing and evaluation, patient observation, and/or the like, and/or a dose that causes a detectable change in biological or chemical activity. The detectable changes may be detected and/or further quantified by one skilled in the art for the relevant mechanism or process. As is generally understood in the art, the dosage will vary depending on the administration routes, symptoms and body weight of the patient but also depending upon the compound being administered.

Administration of two or more compounds "in combination" means that the two compounds are administered closely enough in time that the presence of one alters the biological effects of the other. The two compounds can be administered simultaneously (concurrently) or sequentially. Simultaneous administration can be carried out by mixing the compounds prior to administration, or by administering the compounds at the same point in time but at different anatomic sites or using different routes of administration. The phrases "concurrent administration", "administration in combination", "simultaneous administration" or "administered simultaneously" as used herein, means that the compounds are administered at the same point in time or immediately following one another. In the latter case, the two compounds are administered at times sufficiently close that the results observed are indistinguishable from those achieved when the compounds are administered at the same point in time.

The term "pharmaceutically active metabolite" is intended to mean a pharmacologically active product produced through metabolism in the body of a specified compound.

The term "solvate" is intended to mean a pharmaceutically acceptable solvate form of a specified compound that retains the biological effectiveness of such compound. Examples of solvates, without limitation, include compounds of the invention in combination with water, isopropanol, ethanol, methanol, DMSO, ethyl acetate, acetic acid, or ethanolamine.

The term "simultaneously" or "concurrently" is intended to mean, when applied to a disease or disorder, that the diseases or disorders occur at the same point in time for at least some of the time the subject is suffering from the diseases or disorders, or at a time that is sufficiently close that the outcome is indistinguishable from that observed when the diseases or disorders occur at the same point in time. In either instance, the diseases or disorders do not necessarily occur during the entire duration of any other disease or disorder.

The term "sequentially" is intended to mean, when applied to a disease or disorder, that the diseases or disorders do not occur at the same point in time, but occur after the presence of another disease or disorder wherein the outcome is distinguishable from that observed when the diseases or disorders occur at the same point in time.

1. Compounds

Novel macrocyclic compounds of the present invention include macrocyclic compounds comprising a building block structure including a tether component that undergoes cyclization to form the macrocyclic compound. The building block structure can comprise amino acids (standard and unnatural), hydroxy acids, hydrazino acids, aza-amino acids, specialized moieties such as those that play a role in the introduction of peptide surrogates and isosteres, and a tether component as described herein. The tether component can be selected from the following:

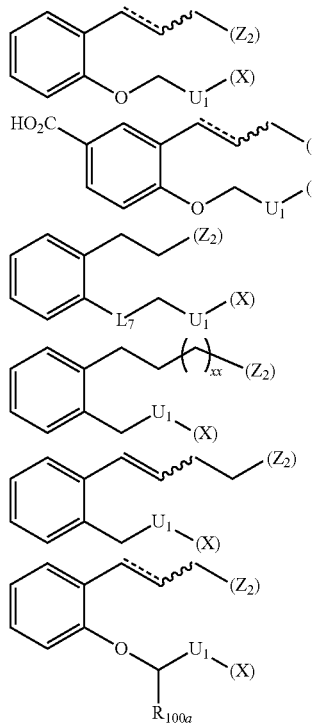

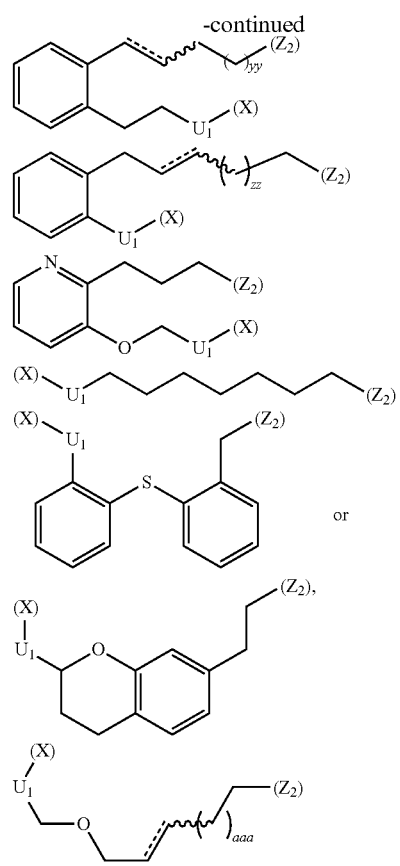

wherein ($Z_2$) is the site of a covalent bond of T to $Z_2$, and $Z_2$ is as defined below for formula I, and wherein (X) is the site of a covalent bond of T to X, and X is as defined below for formula I; $L_7$ is —$CH_2$— or —O—; $U_1$ is —$CR_{101a}R_{102a}$— or —C(=O)—; $R_{100a}$ is lower alkyl; $R_{101a}$ and $R_{102a}$ are each independently hydrogen, lower alkyl or substituted lower alkyl; xx is 2 or 3; yy is 1 or 2; zz is 1 or 2; and aaa is 0 or 1.

Macrocyclic compounds of the present invention further include those of formula I, formula II, formula III and/or formula IV:

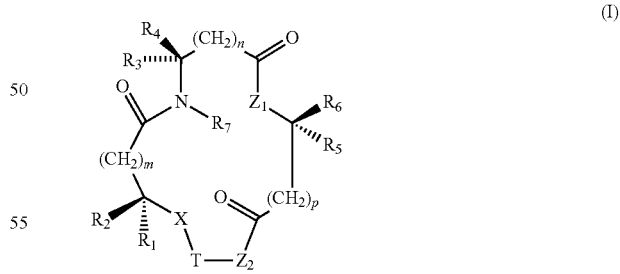

(I)

or a pharmaceutically acceptable salt, hydrate, solvate, optical isomer, enantiomer, diastereomer, racemate or stereochemical mixture thereof, wherein:

$R_1$ is hydrogen or the side chain of an amino acid, or alternatively $R_1$ and $R_2$ together form a 4-, 5-, 6-, 7- or 8-membered ring, optionally comprising an O, S or N atom in the ring, wherein the ring is optionally substituted with $R_8$ as defined below, or alternatively $R_1$ and $R_9$ together form a 3-, 4-, 5-, 6- or 7-membered ring, optionally comprising an O, S or additional N atom in the ring, wherein the ring is optionally substituted with $R_8$ as defined below;

$R_2$ is hydrogen or the side chain of an amino acid, or alternatively $R_1$ and $R_2$ together form a 4-, 5-, 6-, 7- or 8-membered ring, optionally comprising an O, S or N atom in the ring, wherein the ring is optionally substituted with $R_8$ as defined below; or alternatively $R_2$ and $R_9$ together form a 3-, 4-, 5-, 6- or 7-membered ring, optionally comprising an O, S or additional N atom in the ring, wherein the ring is optionally substituted with $R_8$ as defined below;

$R_3$ is hydrogen or the side chain of an amino acid, or alternatively $R_3$ and $R_4$ together form a 3-, 4-, 5-, 6- or 7-membered ring, optionally comprising an O or S atom in the ring, wherein the ring is optionally substituted with $R_8$ as defined below, or alternatively, $R_3$ and $R_7$ or $R_3$ and $R_{11}$ together form a 4-, 5-, 6-, 7- or 8-membered heterocyclic ring, optionally comprising an O, S or additional N atom in the ring, wherein the ring is optionally substituted with $R_8$ as defined below;

$R_4$ is hydrogen or the side chain of an amino acid, or alternatively $R_4$ and $R_3$ together form a 3-, 4-, 5-, 6- or 7-membered ring, optionally comprising an O or S atom in the ring, wherein the ring is optionally substituted with $R_8$ as defined below, or alternatively $R_4$ and $R_7$ or $R_4$ and $R_{11}$ together form a 4-, 5-, 6-, 7- or 8-membered heterocyclic ring, optionally comprising an O, S or additional N atom in the ring, wherein the ring is optionally substituted with $R_8$ as defined below;

$R_5$ and $R_6$ are each independently hydrogen or the side chain of an amino acid or alternatively $R_5$ and $R_6$ together form a 3-, 4-, 5-, 6- or 7-membered ring, optionally comprising an O, S or N atom in the ring, wherein the ring is optionally substituted with $R_8$ as defined below;

$R_7$ is hydrogen, lower alkyl, substituted lower alkyl, cycloalkyl, substituted cycloalkyl, a heterocyclic group, or a substituted heterocyclic group, or alternatively $R_3$ and $R_7$ or $R_4$ and $R_7$ together form a 4-, 5-, 6-, 7- or 8-membered heterocyclic ring optionally comprising an O, S or additional N atom in the ring, wherein the ring is optionally substituted with $R_8$ as described below;

$R_8$ is substituted for one or more hydrogen atoms on the 3-, 4-, 5-, 6-, 7- or 8-membered ring structure and is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfinyl, sulfonyl and sulfonamido, or, alternatively, $R_8$ is a fused cycloalkyl, a substituted fused cycloalkyl, a fused heterocyclic, a substituted fused heterocyclic, a fused aryl, a substituted fused aryl, a fused heteroaryl or a substituted fused heteroaryl ring when substituted for hydrogen atoms on two adjacent atoms;

X is O, $NR_9$ or $N(R_{10})_2^+$;

wherein $R_9$ is hydrogen, lower alkyl, substituted lower alkyl, sulfonyl, sulfonamido or amidino and $R_{10}$ is hydrogen, lower alkyl, or substituted lower alkyl, or alternatively $R_9$ and $R_1$ together form a 3-, 4-, 5-, 6- or 7-membered ring, optionally comprising an O, S or additional N atom in the ring, wherein the ring is optionally substituted with $R_8$ as defined above;

$Z_1$ is O or $NR_{11}$, wherein $R_{11}$ is hydrogen, lower alkyl, or substituted lower alkyl, or alternatively $R_3$ and $R_{11}$ or $R_4$ and $R_{11}$ together form a 4-, 5-, 6-, 7- or 8-membered heterocyclic ring, optionally comprising an O, S or additional N atom in the ring, wherein the ring is optionally substituted with $R_8$ as defined above;

$Z_2$ is O or $NR_{12}$, wherein $R_{12}$ is hydrogen, lower alkyl, or substituted lower alkyl;

m, n and p are each independently 0, 1 or 2;

T is a bivalent radical of formula V:

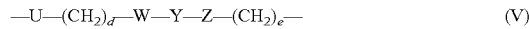

wherein d and e are each independently 0, 1, 2, 3, 4 or 5; Y and Z are each optionally present; U is —$CR_{21}Z_{22}$— or —C(=O)— and is bonded to X of formula I; W, Y and Z are each independently selected from the group consisting of —O—, —$NR_{23}$—, —S—, —SO—, —$SO_2$—, —C(=O)—O—, —O—C(=O)—, —C(=O)—NH—, —NH—C(=O)—, —$SO_2$—NH—, —NH—$SO_2$—, —$CR_{24}R_{25}$—, —CH=CH— with the configuration Z or E, —C≡C— and the ring structures below:

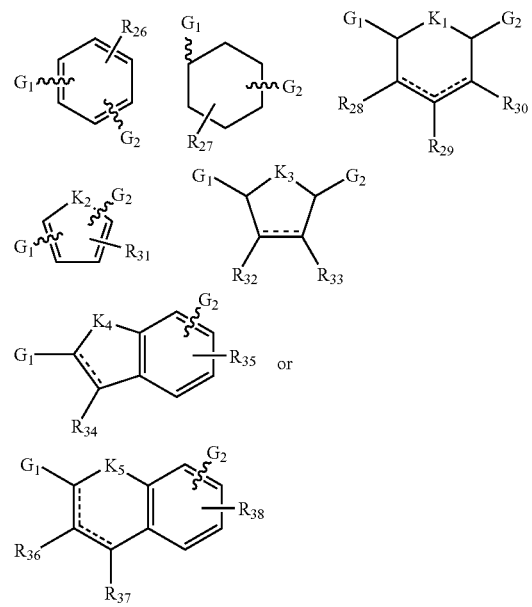

wherein $G_1$ and $G_2$ are each independently a covalent bond or a bivalent radical selected from the group consisting of —O—, —$NR_{39}$—, —S—, —SO—, —$SO_2$—, —C(=O)—, —C(=O)—O—, —O—C(=O)—, —C(=O)NH—, —NH—C(=O)—, —$SO_2$—NH—, —NH—$SO_2$—, —$CR_{40}R_{41}$—, —CH=CH— with the configuration Z or E, and —C≡C—; with $G_1$ being bonded closest to the group U; wherein any carbon atom in the rings not otherwise defined, is optionally replaced by N, with the proviso that the ring cannot contain more than four N atoms; $K_1$, $K_2$, $K_3$, $K_4$ and $K_5$ are each independently O, $NR_{42}$ or S, wherein $R_{42}$ is as defined below;

$R_{21}$ and $R_{22}$ are each independently hydrogen, lower alkyl, or substituted lower alkyl, or alternatively $R_{21}$ and $R_{22}$ together form a 3- to 12-membered cyclic ring optionally comprising one or more heteroatoms selected from the group consisting of O, S and N, wherein the ring is optionally substituted with $R_8$ as defined above;

$R_{23}$, $R_{39}$ and $R_{42}$ are each independently hydrogen, alkyl, substituted alkyl, cycloalkyl, substituted cycloalkyl, heterocyclic, substituted heterocyclic, aryl, substituted aryl, heteroaryl, substituted heteroaryl, formyl, acyl, carboxyalkyl, carboxyaryl, amido, amidino, sulfonyl or sulfonamido;

$R_{24}$ and $R_{25}$ are each independently hydrogen, lower alkyl, substituted lower alkyl, $R_{AA}$, wherein $R_{AA}$ is a side chain of an amino acid such as a standard or unusual amino acid, or alternatively $R_{24}$ and $R_{25}$ together form a 3- to 12-membered cyclic ring optionally comprising one or more heteroatoms selected from the group consisting of O, S and N; or alternatively one of $R_{24}$ or $R_{25}$ is hydroxy, alkoxy, aryloxy, amino, mercapto, carbamoyl, amidino, ureido or guanidino while the other is hydrogen, lower alkyl or substituted lower alkyl, except when the carbon to which $R_{24}$ and $R_{25}$ are bonded is also bonded to another heteroatom;

$R_{26}$, $R_{31}$, $R_{35}$ and $R_{38}$ are each optionally present and, when present, are substituted for one or more hydrogen atoms on the indicated ring and each is independently selected from the group consisting of halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro, mercapto, sulfinyl, sulfonyl and sulfonamido;

$R_{27}$ is optionally present and is substituted for one or more hydrogen atoms on the indicated ring and each is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl and sulfonamido;

$R_{28}$, $R_{29}$, $R_{30}$, $R_{32}$, $R_{33}$, $R_{34}$, $R_{36}$ and $R_{37}$ are each optionally present and, when no double bond is present to the carbon atom to which it is bonded in the ring, two groups are optionally present, and when present, is substituted for one hydrogen present in the ring, or when no double bond is present to the carbon atom to which it is bonded in the ring, is substituted for one or both of the two hydrogen atoms present on the ring and each is independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl, sulfonamido and, only if a double bond is present to the carbon atom to which it is bonded, halogen; and $R_{40}$ and $R_{41}$ are each independently hydrogen, lower alkyl, substituted lower alkyl, $R_{44}$ as defined above, or alternatively $R_{40}$ and $R_{41}$ together form a 3- to 12-membered cyclic ring optionally comprising one or more heteroatoms selected from the group consisting of O, S and N wherein the ring is optionally substituted with $R_8$ as defined above, or alternatively one of $R_{40}$ and $R_{41}$ is hydroxy, alkoxy, aryloxy, amino, mercapto, carbamoyl, amidino, ureido or guanidino, while the other is hydrogen, lower alkyl or substituted lower alkyl, except when the carbon to which $R_{40}$ and $R_{41}$ are bonded is also bonded to another heteroatom;

with the proviso that T is not an amino acid residue, dipeptide fragment, tripeptide fragment or higher order peptide fragment comprising standard amino acids;

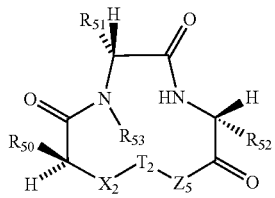

(II)

or a pharmaceutically acceptable salt, hydrate, solvate, optical isomer, enantiomer, diastereomer, racemate or stereochemical mixture thereof, wherein:

$R_{50}$ is $-(CH_2)_{ss}CH_3$, $-CH(CH_3)(CH_2)_{tt}CH_3$, $-(CH_2)_{uu}CH(CH_3)_2$, $-C(CH_3)_3$, $-(CHR_{55})_{vv}-R_{56}$, or $-CH(OR_{57})CH_3$, wherein ss is 1, 2 or 3; tt is 1 or 2; uu is 0, 1 or 2; and vv is 0, 1, 2, 3 or 4; $R_{55}$ is hydrogen or $C_1$-$C_4$ alkyl; $R_{56}$ is amino, hydroxy, alkoxy, cycloalkyl or substituted cycloalkyl; and $R_{57}$ is hydrogen, alkyl, acyl, amino acyl, sulfonyl, carboxyalkyl or carboxyaryl;

$R_{51}$ is hydrogen, $C_1$-$C_4$ alkyl or $C_1$-$C_4$ alkyl substituted with hydroxy or alkoxy;

$R_{52}$ is $-(CHR_{58})_{ww}R_{59}$, wherein ww is 0, 1, 2 or 3; $R_{58}$ is hydrogen, $C_1$-$C_4$ alkyl, amino, hydroxy or alkoxy; $R_{59}$ is aryl, substituted aryl, heteroaryl, substituted heteroaryl, cycloalkyl or substituted cycloalkyl;

$R_{53}$ is hydrogen or $C_1$-$C_4$ alkyl;

$X_2$ is O, $NR_9$ or $N(R_{10})_2^+$;

wherein $R_9$ is hydrogen, lower alkyl, substituted lower alkyl, sulfonyl, sulfonamido or amidino and $R_{10}$ is hydrogen, lower alkyl, or substituted lower alkyl;

$Z_5$ is O or $NR_{12}$, wherein $R_{12}$ is hydrogen, lower alkyl, or substituted lower alkyl; and $T_2$ is a bivalent radical of formula VI:

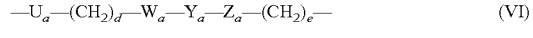

(VI)

wherein d and e are independently 0, 1, 2, 3, 4 or 5; $Y_a$ and $Z_a$ are each optionally present; $U_a$ is $-CR_{60}R_{61}-$ or $-C(=O)-$ and is bonded to $X_2$ of formula II, wherein $R_{60}$ and $R_{61}$ are each independently hydrogen, lower alkyl, or substituted lower alkyl, or alternatively $R_{21}$ and $R_{22}$ together form a 3- to 12-membered cyclic ring optionally comprising one or more heteroatoms selected from the group consisting of O, S and N, wherein the ring is optionally substituted with $R_8$ as defined above; $W_a$, $Y_a$ and $Z_a$ are each independently selected from the group consisting of: $-O-$, $-NR_{62}-$, $-S-$, $-SO-$, $-SO_2-$, $-C(=O)-O-$, $-O-C(=O)-$, $-C(=O)-NH-$, $-NH-C(=O)-$, $-SO_2-NH-$, $-NH-SO_2-$, $-CR_{63}R_{64}-$, $-CH=CH-$ with the configuration Z or E, $-C\equiv C-$, and the ring structures depicted below:

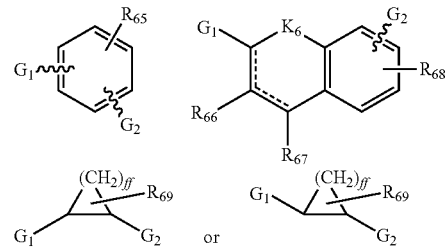

wherein $G_1$ and $G_2$ are as defined above, and wherein any carbon atom in the ring is optionally replaced by N, with the proviso that the aromatic ring cannot contain more than four N atoms and the cycloalkyl ring cannot contain more than two N atoms;

$R_{62}$ is hydrogen, alkyl, substituted alkyl, cycloalkyl, substituted cycloalkyl, a heterocyclic group, a substituted heterocyclic group, aryl, substituted aryl, heteroaryl, substituted heteroaryl, formyl, acyl, carboxyalkyl, carboxyaryl, amido, amidino, sulfonyl or sulfonamido;

$R_{63}$ and $R_{64}$ are each independently hydrogen, lower alkyl, substituted lower alkyl or $R_{44}$; or alternatively $R_{63}$ and $R_{64}$ together form a 3- to 12-membered cyclic ring optionally comprising one or more heteroatoms selected from the group consisting of O, S and N; or alternatively one of $R_{63}$ and $R_{64}$ is hydroxy, alkoxy, aryloxy, amino, mercapto, carbamoyl, amidino, ureido or guanidino, while the other is hydrogen, lower alkyl or substituted lower alkyl, except when the carbon to which $R_{63}$ and $R_{64}$ are bonded is also bonded to another heteroatom; and $R_{AA}$ indicates the side chain of a standard or unusual amino acid;

$R_{65}$ and $R_{68}$ are each optionally present, and, when present are substituted for one or more hydrogen atoms on the ring and each is independently halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro, mercapto, sulfinyl, sulfonyl or sulfonamido;

$R_{66}$ and $R_{67}$ are each optionally present, and when no double bond is present to the carbon atom to which it is bonded in the ring, two groups are optionally present, and, when present, each is substituted for one hydrogen present in the ring, or when no double bond is present to the carbon atom to which it is bonded in the ring, is substituted for one or both of the two hydrogen atoms present on the ring and each is independently alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl, sulfonamido and, only if a double bond is present to the carbon atom to which it is bonded, halogen;

$R_{69}$ is optionally present, and when present is substituted for one or more hydrogen atoms on the ring and each is independently alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, formyl, acyl, carboxy, carboxyalkyl, carboxyaryl, amido, carbamoyl, guanidino, ureido, amidino, mercapto, sulfinyl, sulfonyl or sulfonamido;

$K_6$ is O or S; and ff is 1, 2, 3, 4 or 5;

with the proviso that $T_2$ is not an amino acid residue, dipeptide fragment, tripeptide fragment or higher order peptide fragment comprising standard amino acids; or

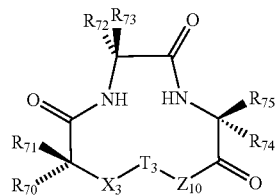

(III)

or a pharmaceutically acceptable salt, hydrate, solvate, optical isomer, enantiomer, diastereomer, racemate or stereochemical mixture thereof,
wherein:

$R_{70}$ is hydrogen, $C_1$-$C_4$ alkyl or alternatively $R_{70}$ and $R_{71}$ together form a 4-, 5-, 6-, 7- or 8-membered ring, optionally comprising an O, N or S atom in the ring, wherein the ring is optionally substituted with $R_{8a}$ as defined below;

$R_{71}$ is hydrogen, —$(CH_2)_{aa}CH_3$, —$CH(CH_3)$ $(CH_2)_{bb}CH_3$, —$(CH_2)_{cc}$—$CH(CH_3)_2$, —$(CH_2)_{dd}$—$R_{76}$ or —$CH(OR_{77})CH_3$ or, alternatively $R_{71}$ and $R_{70}$ together form a 4-, 5-, 6-, 7- or 8-membered ring, optionally comprising an O, N or S atom in the ring, wherein the ring is optionally substituted with $R_{8a}$ as defined below; wherein aa is 0, 1, 2, 3, 4 or 5; bb is 1, 2 or 3; cc is 0, 1, 2 or 3; and dd is 0, 1, 2, 3 or 4; $R_{76}$ is aryl, substituted aryl, heteroaryl, substituted heteroaryl, cycloalkyl or substituted cycloalkyl; $R_{77}$ is hydrogen, alkyl, acyl, amino acyl, sulfonyl, carboxyalkyl or carboxyaryl;

$R_{72}$ is $C_1$-$C_4$ alkyl; or alternatively $R_{72}$ and $R_{73}$ together form a 3-, 4-, 5-, 6- or 7-membered ring, optionally comprising an O or S atom in the ring, wherein the ring is optionally substituted with $R_{8b}$ as defined below;

$R_{73}$ is hydrogen, or alternatively $R_{73}$ and $R_{72}$ together form a 3-, 4-, 5-, 6- or 7-membered ring, optionally comprising an O, S or N atom in the ring, wherein the ring is optionally substituted with $R_{8b}$ as defined below;

$R_{74}$ is hydrogen or $C_1$-$C_4$ alkyl or alternatively $R_{74}$ and $R_{75}$ together form a 3-, 4-, 5-, 6- or 7-membered ring, optionally comprising an O, N or S atom in the ring, wherein the ring is optionally substituted with $R_{8c}$ as defined below;

$R_{75}$ is —$(CHR_{78})R_{79}$ or alternatively $R_{75}$ and $R_{74}$ together form a 3-, 4-, 5-, 6- or 7-membered ring, optionally comprising an O, N or S atom in the ring, wherein the ring is optionally substituted with $R_{8c}$ as defined below; wherein $R_{78}$ is hydrogen, $C_1$-$C_4$ alkyl, amino, hydroxy or alkoxy, and $R_{79}$ is selected from the group consisting of the following structures:

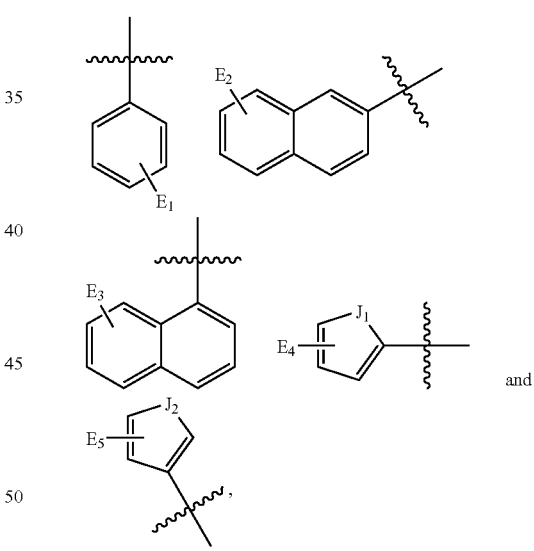

wherein $E_1$, $E_2$, $E_3$, $E_4$ and $E_5$ are each optionally present and when present are each independently selected from the group consisting of halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, cyano, sulfinyl, sulfonyl and sulfonamido, and represent substitution at one or more available positions on the monocyclic or bicyclic aromatic ring, wherein said substitution is made with the same or different selected group member, and $J_1$ and $J_2$ are each independently O or S;

$R_{8a}$, $R_{8b}$ and $R_{8c}$ are each independently substituted for one or more hydrogen atoms on the 3-, 4-, 5-, 6-, 7- or 8-membered ring structure and are independently selected from the group consisting of alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfinyl, sulfonyl and sulfonamido, or, alternatively, $R_{8a}$, $R_{8b}$ and $R_{8c}$ are each independently a fused cycloalkyl, a substituted fused cycloalkyl, a fused heterocyclic, a substituted fused heterocyclic, a fused aryl, a substituted fused aryl, a fused heteroaryl or a substituted fused heteroaryl ring when substituted for hydrogen atoms on two adjacent atoms;

$X_3$ is O, $NR_9$ or $N(R_{10})_2^+$;

wherein $R_9$ is hydrogen, lower alkyl, substituted lower alkyl, sulfonyl, sulfonamido or amidino and $R_{10}$ is hydrogen, lower alkyl, or substituted lower alkyl;

$Z_{10}$ is O or $NR_{12}$, wherein $R_{12}$ is hydrogen, lower alkyl, or substituted lower alkyl; and $T_3$ is the same as defined for $T_2$ with the exception that $U_a$ is bonded to $X_3$ of formula III; or

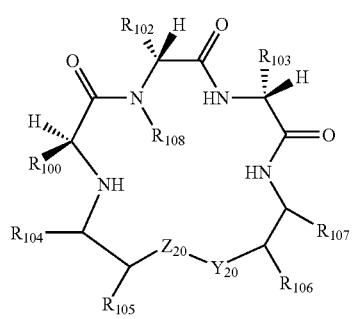

(IV)

or a pharmaceutically acceptable salt, hydrate, solvate, optical isomer, enantiomer, diastereomer, racemate or stereochemical mixture thereof
wherein:

$R_{100}$ is cycloalkyl;

$R_{102}$ is selected from the group consisting of lower alkyl and substituted lower alkyl;

$R_{103}$ is selected from the group consisting of alkyl and alkyl substituted with aryl;

$R_{104}$, $R_{105}$, $R_{106}$, and $R_{107}$ are independently selected from the group consisting of hydrogen, lower alkyl and substituted lower alkyl;

$R_{108}$ is selected from the group consisting of hydrogen and lower alkyl;

$Y_{20}$ is selected from the group consisting of O and $CR_{9a}R_{9b}$; wherein $R_{9a}$ and $R_{9b}$ are independently selected from the group consisting of hydrogen and lower alkyl;

$Z_{20}$ is selected from the group consisting of:

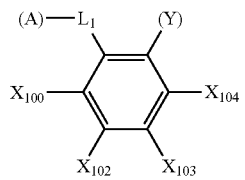

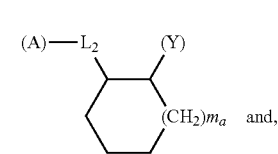

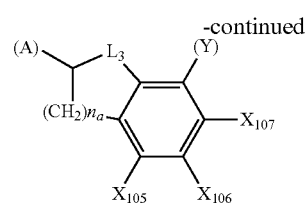

wherein (A) and (Y) indicate the bonds of $Z_{20}$ to $CHR_{105}$ and $Y_{20}$ of formula IV, respectively;

$L_1$, $L_2$ and $L_3$ are independently selected from the group consisting of O, and $CR_{10a}R_{10b}$; wherein $R_{10a}$ and $R_{10b}$ are independently selected from the group consisting of hydrogen and lower alkyl;

$X_{100}$, $X_{102}$, $X_{103}$, $X_{104}$, $X_{105}$, $X_{106}$ and $X_{107}$ are independently selected from the group consisting of hydrogen, halogen, trifluoromethyl and lower alkyl; and $m_a$ is 0 or 1; and $n_a$ is 1 or 2.

In some embodiments, when the macrocyclic compound has the structure of formula IV, $R_{100}$ is cyclopropyl or cyclohexyl. In some embodiments, $R_{102}$ and $R_{108}$ are each methyl. In other embodiments, $R_{103}$ is $-CH_2CH(CH_3)_2$ or $-CHR_{110}R_{120}$, wherein $R_{110}$ is hydrogen or methyl and $R_{120}$ is selected from the group consisting of

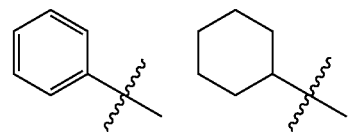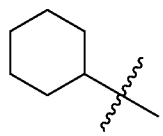

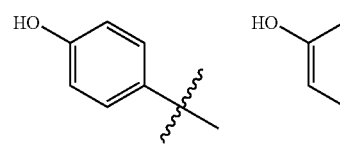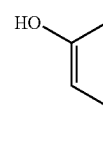

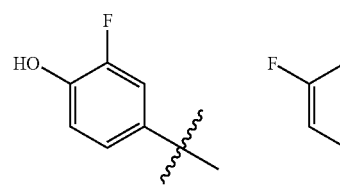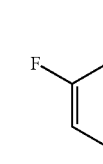

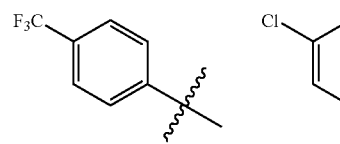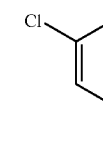

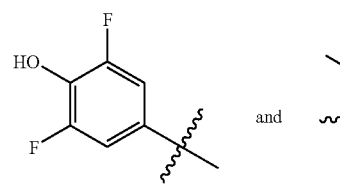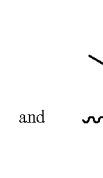

In still other embodiments, $Z_{20}$ is selected from the group consisting of:

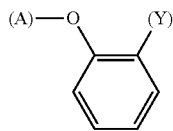 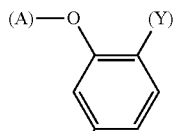

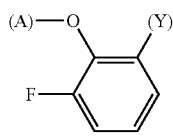 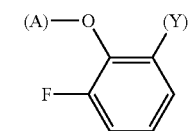

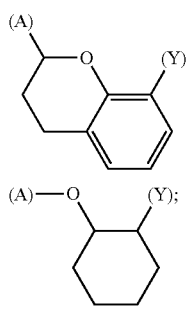 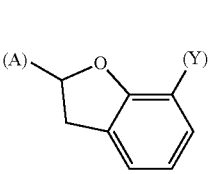 and

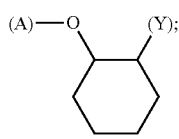

wherein (A) and (Y) indicate the bonds of $Z_{20}$ to $CHR_{105}$ and $Y_{20}$ of formula IV, respectively. According to still other embodiments, where $R_{104}$ and $R_{106}$ are hydrogen and $R_{105}$ and $R_{107}$ are methyl, Y is $CH_2$ and $Z_{20}$ is

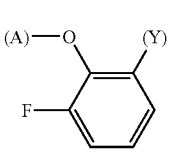

wherein (A) and (Y) indicate the bonds of $Z_{20}$ to $CHR_{105}$ and $Y_{20}$ of formula IV, respectively. In some embodiments, where $R_{104}$, $R_{105}$, $R_{106}$ and $R_{107}$ are hydrogen, $Y_{20}$ is $CH_2$ and $Z_{20}$ is

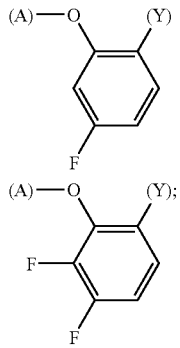 or 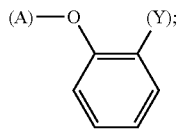

wherein (A) and (Y) indicate the bonds of $Z_{20}$ to $CHR_{105}$ and $Y_{20}$ of formula IV, respectively. In some embodiments, where $R_{104}$, $R_{105}$, $R_{106}$ and $R_{107}$ are hydrogen, $Y_{20}$ is $CH_2$ and $Z_{20}$ is

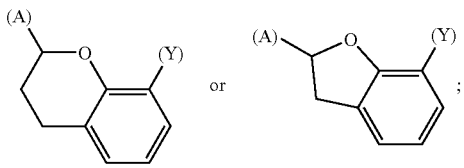

wherein (A) and (Y) indicate the bonds of $Z_{20}$ to $CHR_{105}$ and $Y_{20}$ of formula I, respectively. According to some embodiments, wherein $R_{104}$, $R_{106}$ and $R_{107}$ are hydrogen, $R_{105}$ is methyl, $Y_{20}$ is $CH_2$ and $Z_{20}$ is

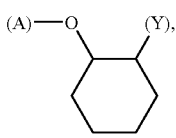

wherein (A) and (Y) indicate the bonds of $Z_{20}$ to $CHR_{105}$ and $Y_{20}$ of formula IV, respectively.

In some embodiments of the present invention, the compound can have one of the following structure:

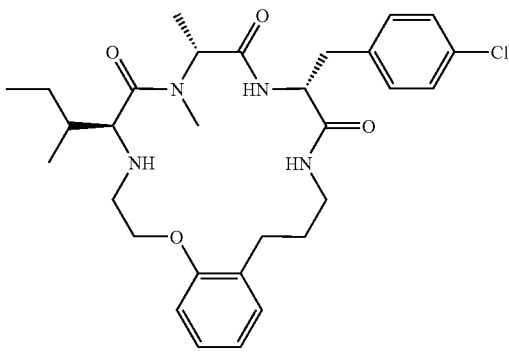

25

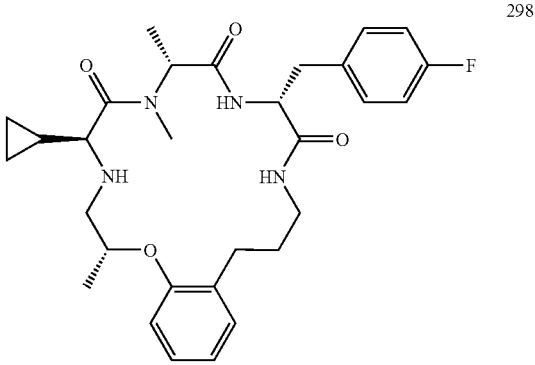

298

43
-continued
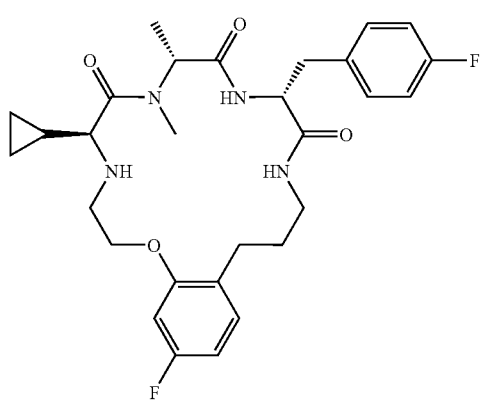
753
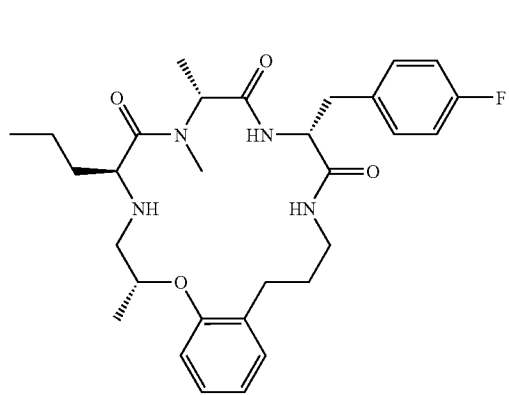
754
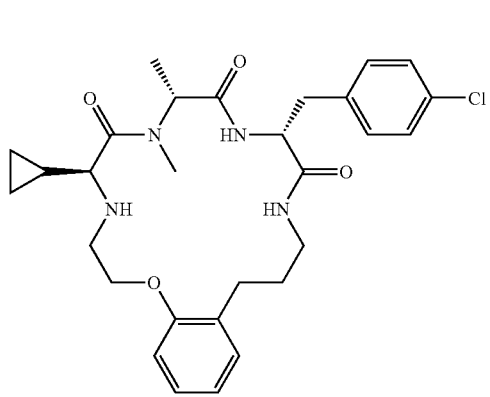
755
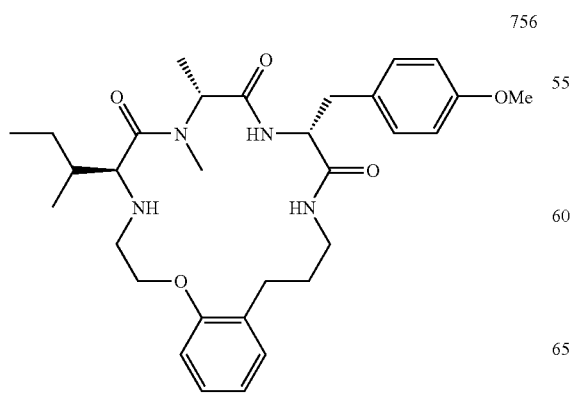
756
44
-continued
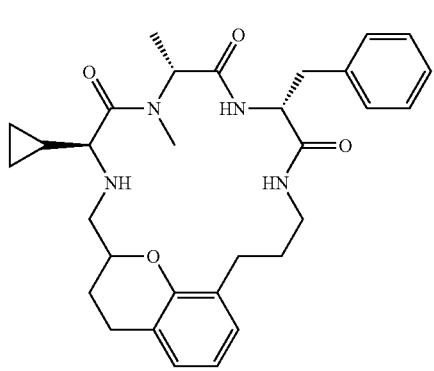
757
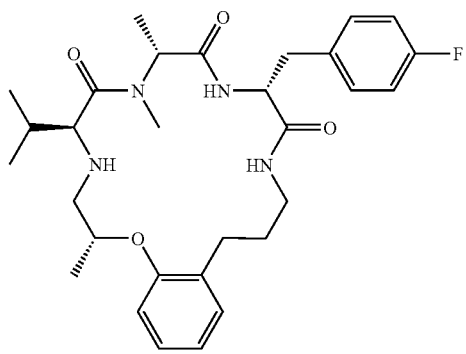
758
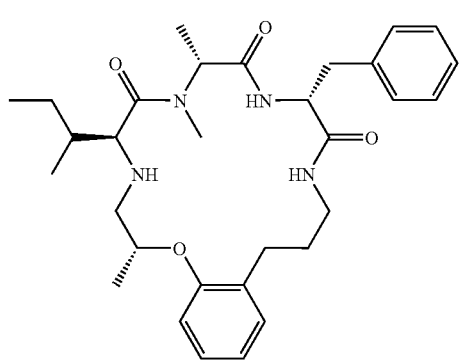
759
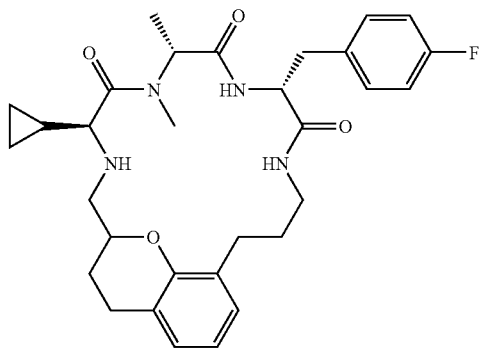
760

45
-continued

761

762

763

764

46
-continued

765

766

767

768

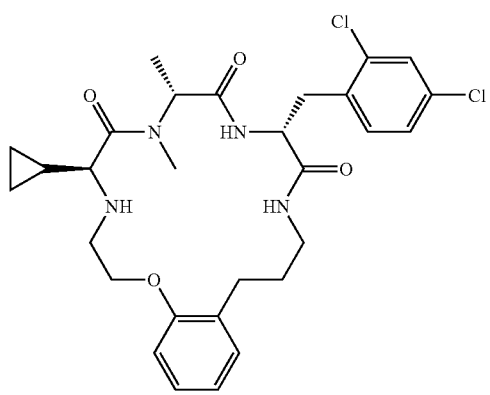
769
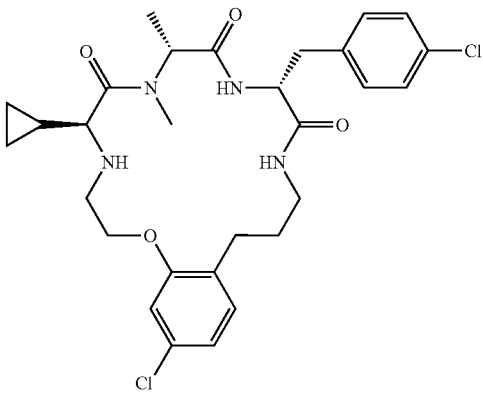
773
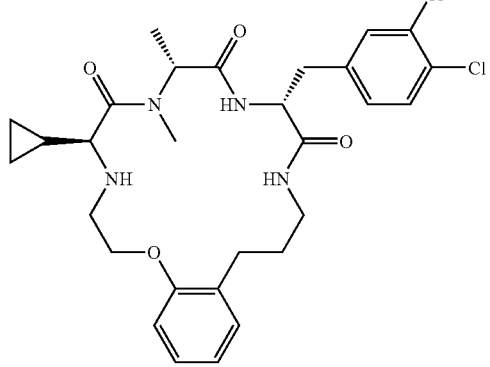
770
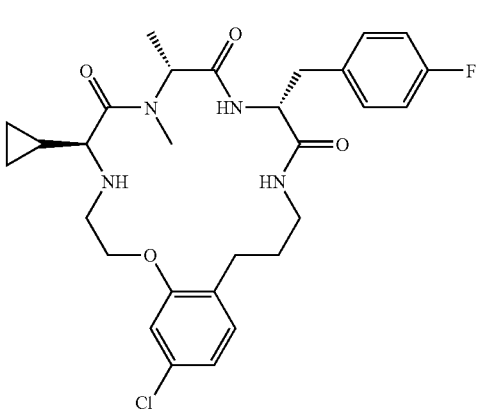
774
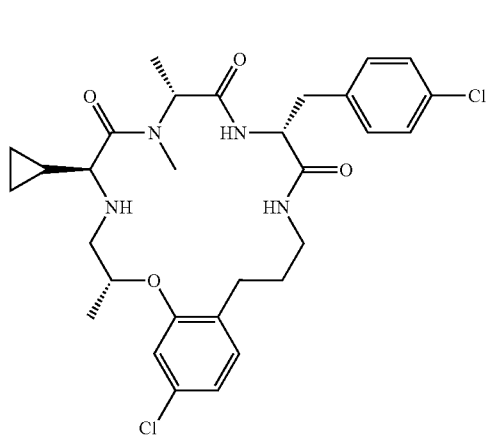
771
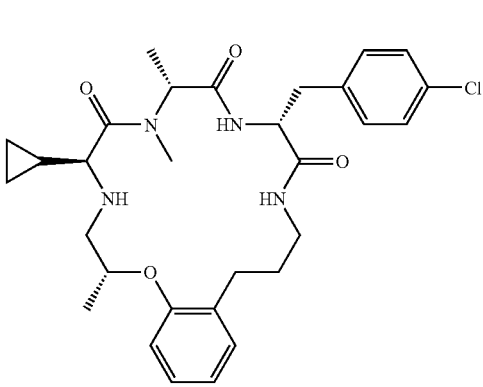
775
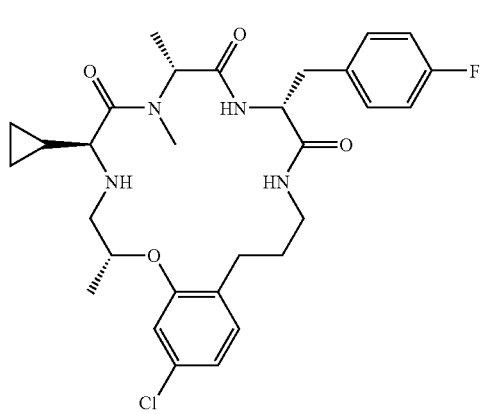
772
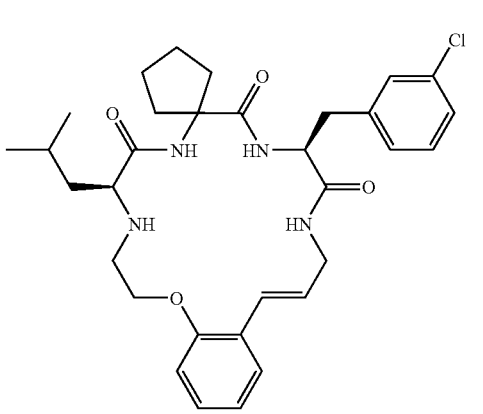
776

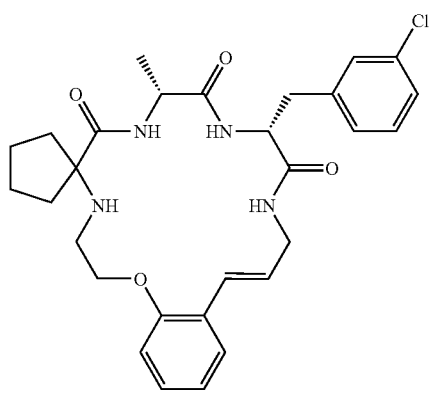
777
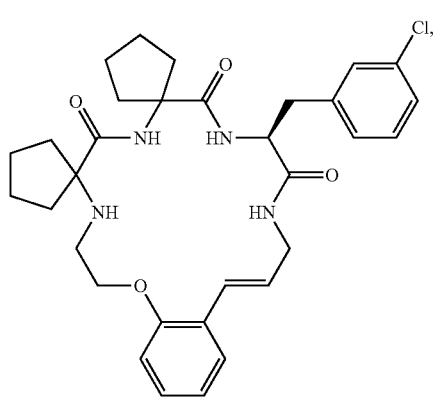
778
or a pharmaceutically acceptable salt, hydrate, solvate, optical isomer, enantiomer, diastereomer, racemate or stereochemical mixture thereof.
In other embodiments, the compound can have one of the following structures:
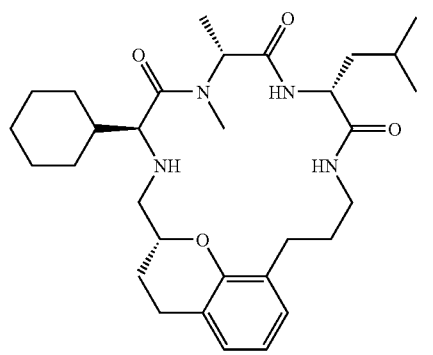
801
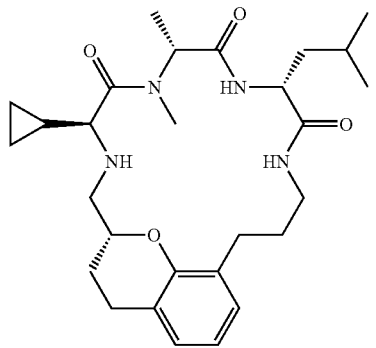
802
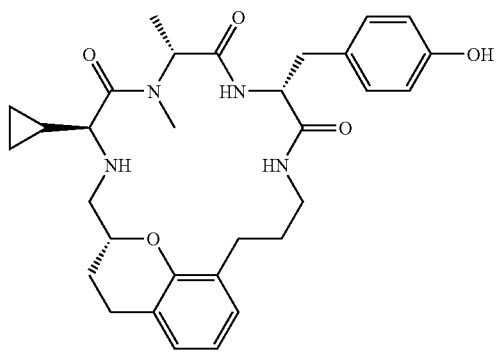
803
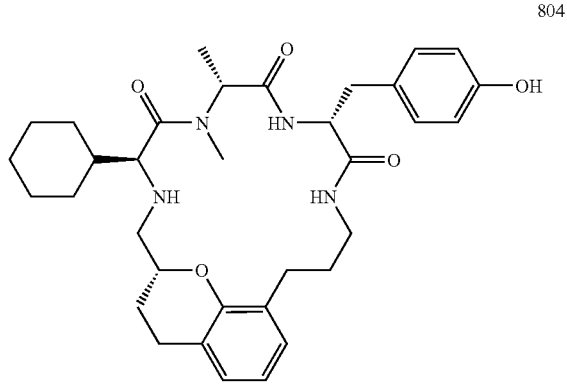
804
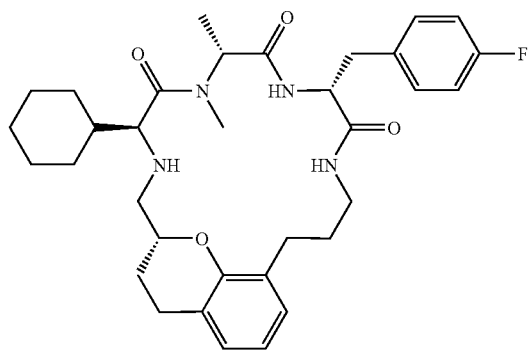
805
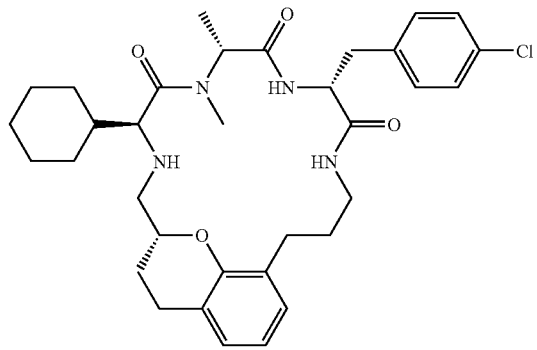
806

807
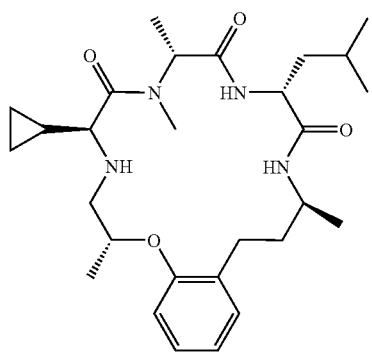
808
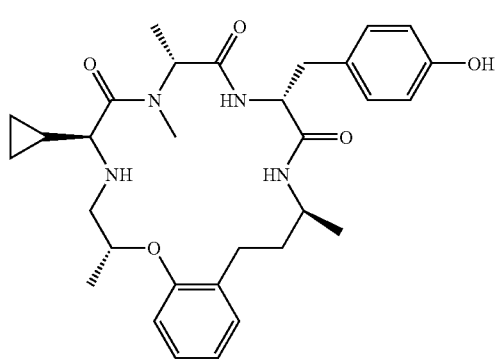
809
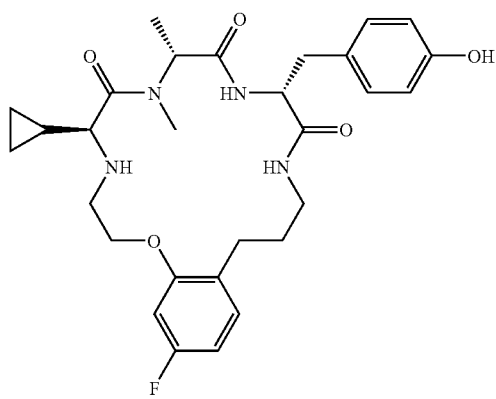
810
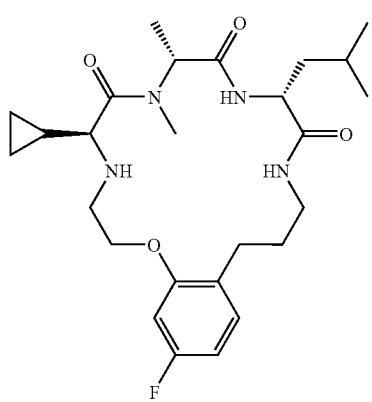
811
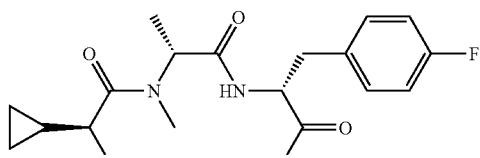
812
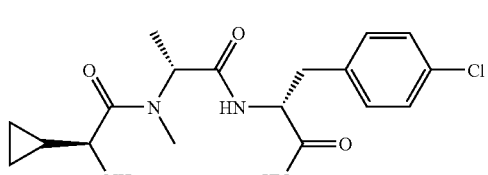
813
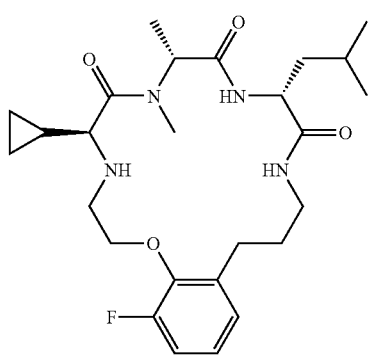
814
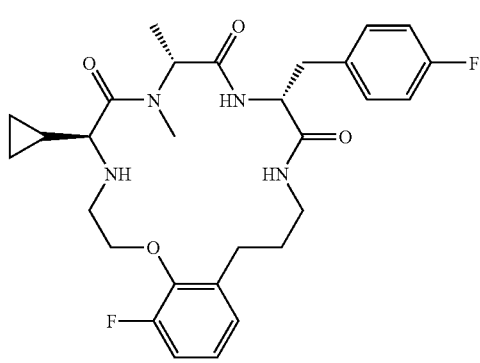

53
-continued
815
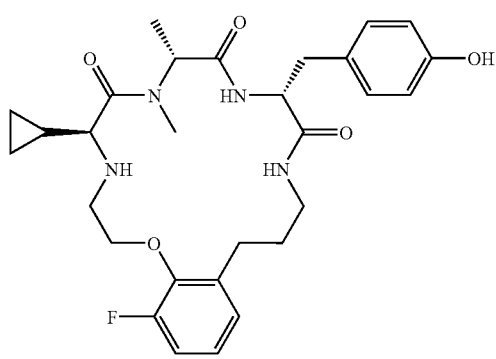
816
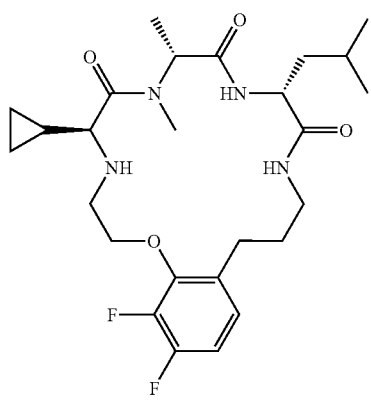
817
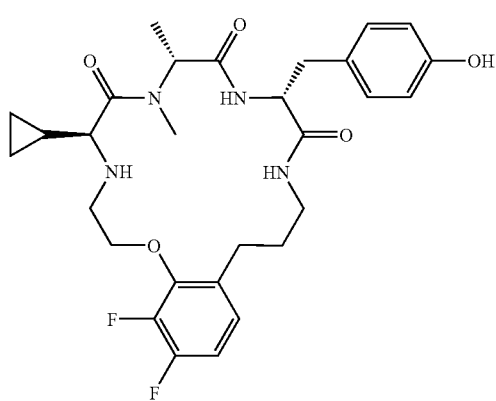
818
54
-continued
819
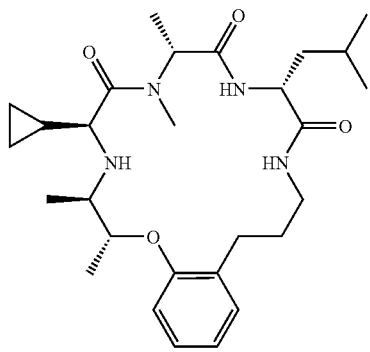
820
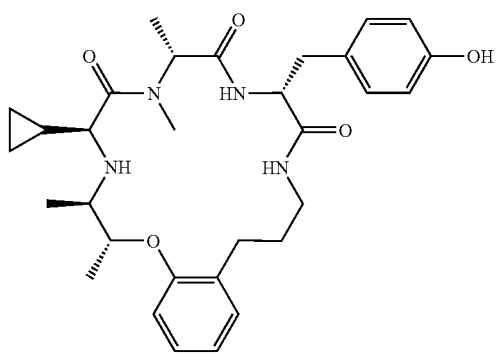
821
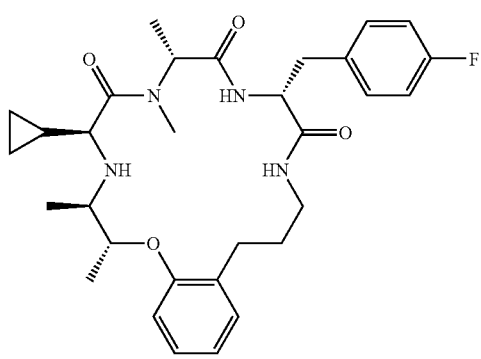
822
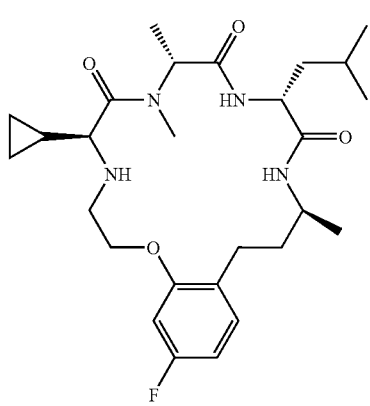

55
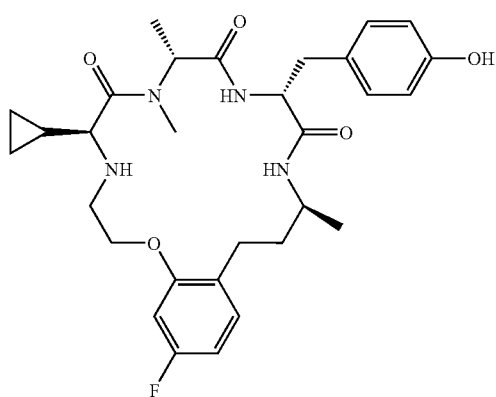
823
824
825
826
56
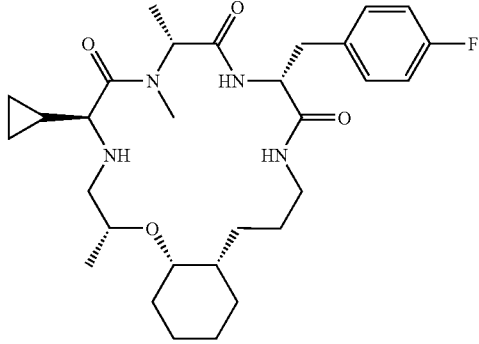
827
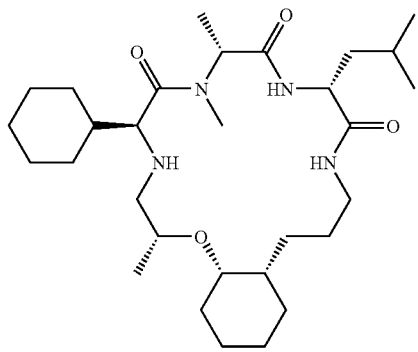
828
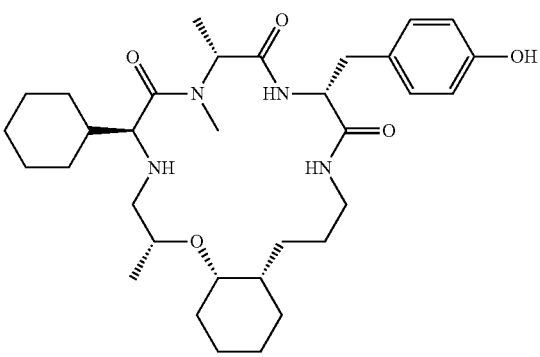
829
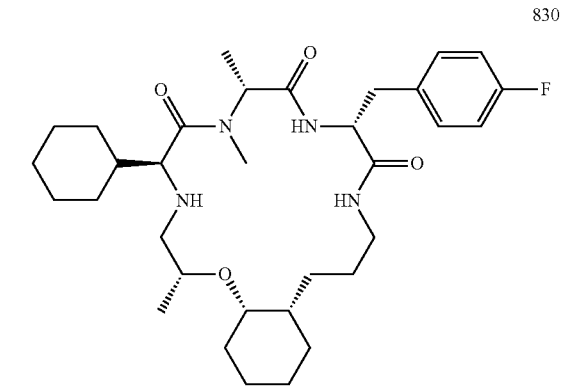
830

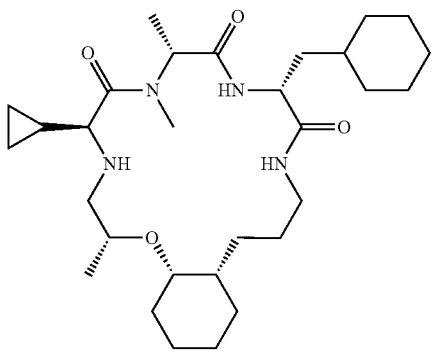

a pharmaceutically acceptable salt, hydrate, solvate, optical isomer, enantiomer, diastereomer, racemate or stereochemical mixture thereof.

The present invention includes isolated compounds. An isolated compound refers to a compound that, in some embodiments, comprises at least 10%, at least 25%, at least 50% or at least 70% of the compounds of a mixture. In some embodiments, the compound, pharmaceutically acceptable salt thereof or pharmaceutical composition containing the compound exhibits a statistically significant binding and/or antagonist activity when tested in biological assays at the human ghrelin receptor.

In the case of compounds, salts, or solvates that are solids, it is understood by those skilled in the art that the inventive compounds, salts, and solvates may exist in different crystal or polymorphic forms, all of which are intended to be within the scope of the present invention and specified formulas.

The compounds of formula I, II, III and/or IV disclosed herein have asymmetric centers. The inventive compounds may exist as single stereoisomers, racemates, and/or mixtures of enantiomers and/or diastereomers. All such single stereoisomers, racemates, and mixtures thereof are intended to be within the scope of the present invention. In particular embodiments, however, the inventive compounds are used in optically pure form. The terms "S" and "R" configuration as used herein are as defined by the IUPAC 1974 Recommendations for Section E, Fundamentals of Stereochemistry (Pure Appl. Chem. 1976, 45, 13-30.)

Unless otherwise depicted to be a specific orientation, the present invention accounts for all stereoisomeric forms. The compounds may be prepared as a single stereoisomer or a mixture of stereoisomers. The non-racemic forms may be obtained by either synthesis or resolution. The compounds may, for example, be resolved into the component enantiomers by standard techniques, for example formation of diastereomeric pairs via salt formation. The compounds also may be resolved by covalently bonding to a chiral moiety. The diastereomers can then be resolved by chromatographic separation and/or crystallographic separation. In the case of a chiral auxiliary moiety, it can then be removed. As an alternative, the compounds can be resolved through the use of chiral chromatography. Enzymatic methods of resolution could also be used in certain cases.

As generally understood by those skilled in the art, an "optically pure" compound is one that contains only a single enantiomer. As used herein, the term "optically active" is intended to mean a compound comprising at least a sufficient excess of one enantiomer over the other such that the mixture rotates plane polarized light. Optically active compounds have the ability to rotate the plane of polarized light. The excess of one enantiomer over another is typically expressed as enantiomeric excess (e.e.). In describing an optically active compound, the prefixes D and L or R and S are used to denote the absolute configuration of the molecule about its chiral center(s). The prefixes "d" and "l" or (+) and (−) are used to denote the optical rotation of the compound (i.e., the direction in which a plane of polarized light is rotated by the optically active compound). The "l" or (−) prefix indicates that the compound is levorotatory (i.e., rotates the plane of polarized light to the left or counterclockwise) while the "d" or (+) prefix means that the compound is dextrarotatory (i.e., rotates the plane of polarized light to the right or clockwise). The sign of optical rotation, (−) and (+), is not related to the absolute configuration of the molecule, R and S.

A compound of the invention having the desired pharmacological properties will be optically active and, can be comprised of at least 90% (80% e.e.), at least 95% (90% e.e.), at least 97.5% (95% e.e.) or at least 99% (98% e.e.) of a single isomer.

Likewise, many geometric isomers of double bonds and the like can also be present in the compounds disclosed herein, and all such stable isomers are included within the present invention unless otherwise specified. Also included in the invention are tautomers and rotamers of formula I, II, III and/or IV.

The use of the following symbols at the right refers to

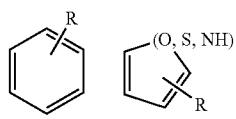

substitution of one or more hydrogen atoms of the indicated ring with the defined substituent R.

The use of the following symbol indicates a single bond or an optional double bond: ----.

2. Synthetic Methods

The compounds of formula I, II, III and/or IV can be synthesized using traditional solution synthesis techniques or solid phase chemistry methods. Synthetic methods for this general type of macrocyclic structure are described in Intl. Pat. Appls. WO 01/25257, WO 2004/111077, WO 2005/012331, WO 2005/012332, WO 2006/009645 and WO 2006/009674 including purification procedures described in WO 2004/111077 and WO 2005/012331. The syntheses of exemplary compound 25 and exemplary compound 298 are provided in WO 2006/009645 and WO 2006/009674. The structures of these compounds are shown in FIG. 1.

3. Biological Methods

The compounds of the present invention were evaluated for their ability to interact at the human ghrelin receptor utilizing a competitive radioligand binding assay, fluorescence assay or Aequorin functional assay as described below. Such methods can be conducted in a high throughput manner to permit the simultaneous evaluation of many compounds.

Specific assay methods for the human (GHS-R1a), swine and rat GHS-receptors (U.S. Pat. No. 6,242,199, Intl. Pat. Appl. Nos. WO 97/21730 and 97/22004), as well as the canine GHS-receptor (U.S. Pat. No. 6,645,726), and their use in generally identifying agonists and antagonists thereof are known.

Appropriate methods for determining the functional activity of compounds of the present invention that interact at the human ghrelin receptor are also described below.

A. Competitive Radioligand Binding Assay (Ghrelin Receptor)

The competitive binding assay at the human ghrelin receptor (growth hormone secretagogue receptor, hGHS-R1a) was carried out analogously to assays described in the literature. (Bednarek M A et al. Structure-function studies on the new growth hormone-releasing peptide ghrelin: minimal sequence of ghrelin necessary for activation of growth hormone secretagogue receptor 1a; J. Med. Chem. 2000, 43, 4370-4376; Palucki, B. L. et al. Spiro(indoline-3,4'-piperidine) growth hormone secretagogues as ghrelin mimetics; Bioorg. Med. Chem. Lett. 2002, 11, 1955-1957.)

Materials

Membranes (GHS-R/HEK 293) were prepared from HEK-293 cells stably transfected with the human ghrelin receptor (hGHS-R1a). These membranes were provided by PerkinElmer BioSignal (#RBHGHSM) and utilized at a quantity of 0.71 µg/assay point.

1. [$^{125}$I]-Ghrelin (PerkinElmer, #NEX-388); final concentration: 0.0070-0.0085 nM
2. Ghrelin (Bachem, #H-4864); final concentration: 1 µM
3. Multiscreen Harvest plates-GF/C (Millipore, #MAHFC1H60)
4. Deep-well polypropylene titer plate (Beckman Coulter, #267006)
5. TopSeal-A (PerkinElmer, #6005185)
6. Bottom seal (Millipore, #MATAH0P00)
7. MicroScint-0 (PerkinElmer, #6013611)
8. Binding Buffer: 25 mM Hepes (pH 7.4), 1 mM CaCl$_2$, 5 mM MgCl$_2$, 2.5 mM EDTA, 0.4% BSA Assay Volumes Competition experiments were performed in a 300 µl filtration assay format.
1. 220 µL of membranes diluted in binding buffer
2. 40 µL of compound diluted in binding buffer
3. 40 µL of radioligand ([125I]-Ghrelin) diluted in binding buffer Final test concentrations (N=1) for compounds of the present invention:
10, 1, 0.5, 0.2, 0.1, 0.05, 0.02, 0.01, 0.005, 0.002, 0.001 µM.

Compound Handling

Compounds were provided frozen on dry ice at a stock concentration of 10 mM diluted in 100% DMSO and stored at −80° C. until the day of testing. On the test day, compounds were allowed to thaw at rt O/N and then diluted in assay buffer according to the desired test concentrations. Under these conditions, the maximal final DMSO concentration in the assay was 0.1%.

Assay Protocol

In deep-well plates, 220 µL of diluted cell membranes (final concentration: 0.71 µg/well) were combined with 40 µL of either binding buffer (total binding, N=5), 1 µM ghrelin (non-specific binding, N=3) or the appropriate concentration of test compound (N=2 for each test concentration). The reaction was initiated by addition of 40 µL of [$^{125}$I]-ghrelin (final conc. 0.0070-0.0085 nM) to each well. Plates were sealed with TopSeal-A, vortexed gently and incubated at rt for 30 min. The reaction was arrested by filtering samples through Multiscreen Harvest plates (pre-soaked in 0.5% polyethyleneimine) using a Tomtec Harvester, washed 9 times with 500 µL of cold 50 mM Tris-HCl (pH 7.4, 4° C.), and then plates were air-dried in a fumehood for 30 min. A bottom seal was applied to the plates prior to the addition of 25 µL of MicroScint-0 to each well. Plates were than sealed with TopSeal-A and counted for 30 sec per well on a Top-Count Microplate Scintillation and Luminescence Counter (PerkinElmer) using a count delay of 60 sec. Results were expressed as counts per minute (cpm).

Data were analyzed by GraphPad Prism (GraphPad Software, San Diego, Calif.) using a variable slope non-linear regression analysis. $K_i$ values were calculated using a $K_d$ value of 0.01 nM for [$^{125}$I]-ghrelin (previously determined during membrane characterization).

$D_{max}$ values were calculated using the following formula:

$$D_{max} = 1 - \frac{\text{test concentration with maximal displacement} - \text{non-specific binding}}{(\text{total binding} - \text{non-specific binding})} \times 100$$

where total and non-specific binding represent the cpm obtained in the absence or presence of 1 µM ghrelin, respectively.

B. Aequorin Functional Assay (Ghrelin Receptor)

The functional activity of compounds found to bind to the ghrelin (GHS-R1a) receptor can be determined using the method described below which can also be used as a primary screen for ghrelin receptor activity in a high throughput fashion. (U.S. Pat. No. 6,872,538; Intl. Pat. Appl. No. WO 00/002045; LePoul, E.; et al. Adaptation of aequorin functional assay to high throughput screening. J. Biomol. Screen. 2002, 7, 57-65; Bednarek, M. A.; et al. Structure-function studies on the new growth hormone-releasing peptide ghrelin: minimal sequence of ghrelin necessary for activation of growth hormone secretagogue receptor 1a. J. Med. Chem. 2000, 43, 4370-4376; Palucki, B. L.; et al. Spiro(indoline-3, 4'-piperidine) growth hormone secretagogues as ghrelin mimetics. Bioorg. Med. Chem. Lett. 2001, 11, 1955-1957.)

Materials

Membranes were prepared using AequoScreen™ (EURO-SCREEN, Belgium) cell lines expressing the human ghrelin receptor (cell line ES-410-A; receptor accession #60179). This cell line is typically constructed by transfection of the human ghrelin receptor into CHO-K1 cells co-expressing $G_{\alpha 16}$ and the mitochondrially targeted Aequorin (Ref #ES-WT-A5).
1. Ghrelin (reference agonist; Bachem, #H-4864)
2. Assay buffer: DMEM (Dulbecco's Modified Eagles Medium) containing 0.1% BSA (bovine serum albumin; pH 7.0).
3. Coelenterazine (Molecular Probes, Leiden, The Netherlands).

Test concentrations (N=8) for compounds of the invention: 10, 1, 0.3, 0.1, 0.03, 0.01, 0.003, 0.001 µM.

Compound Handling

Stock solutions of compounds (10 mM in 100% DMSO) were provided frozen on dry ice and stored at −20° C. prior to use. From the stock solution, mother solutions were made at a concentration of 500 µM by 20-fold dilution in 26% DMSO. Assay plates were then prepared by appropriate dilution in DMEM medium containing 0.1% BSA. Under these conditions, the maximal final DMSO concentration in the assay was <0.6%.

Cell Preparation

AequoScreen™ cells were collected from culture plates with $Ca^{2+}$ and $Mg^{2+}$-free phosphate buffered saline (PBS) supplemented with 5 mM EDTA, pelleted for 2 min at 1000× g, re-suspended in DMEM—Ham's F12 containing 0.1% BSA at a density of $5 \times 10^6$ cells/mL, and incubated O/N at rt in the presence of 5 µM coelenterazine. After loading, cells were diluted with assay buffer to a concentration of $5 \times 10^5$ cells/mL.

Assay Protocol

For agonist testing, 50 µL of the cell suspension was mixed with 50 µL of the appropriate concentration of test compound or ghrelin (reference agonist) in 96-well plates (duplicate samples). Ghrelin (reference agonist) was tested at several concentrations concurrently with the test compounds in order to validate the experiment. The emission of light resulting from receptor activation in response to ghrelin or test compounds was recorded using the Hamamatsu FDSS 6000 reader (Hamamatsu Photonics K.K., Japan).

Analysis and Expression of Results

Results were expressed as Relative Light Units (RLU). Concentration response curves were analyzed using GraphPad Prism (GraphPad Software, San Diego, Calif.) by non-linear regression analysis (sigmoidal dose-response) based on the equation $E=E_{max}/(1+EC_{50}/C)n$ where E was the measured RLU value at a given agonist concentration (C), $E_{max}$ was the maximal response, $EC_{50}$ was the concentration producing 50% stimulation and n was the slope index. For agonist testing, results for each concentration of test compound were expressed as percent activation relative to the signal induced by ghrelin at a concentration equal to the $EC_{80}$ (i.e. 3.7 nM). $EC_{50}$, Hill slope and % $E_{max}$ values are reported.

The results obtained show that the representative compounds examined act as agonists at the ghrelin receptor and are devoid of antagonist activity at the concentrations studied. In addition, these compounds were demonstrated to have high selectivity for the ghrelin receptor versus its closest counterpart, the motilin receptor, with which it has 52% sequence homology. (Feighner, S. D.; Tan, C. P.; McKee, K. K.; Palyha, O. C.; Hreniuk, D. L.; Pong, S.-S.; Austin, C. P.; Figueroa, D.; MacNeil, D.; Cascieri, M. A.; Nargund, R.; Bakshi, R.; Abramovitz, M.; Stocco, R.; Kargmnan, S.; O'Neill, G.; van der Ploeg, L. H. T.; Evans, J.; Patchett, A. A.; Smith, R. G.; Howard, A. D. Receptor for motilin identified in the human gastrointestinal system. Science 1999, 284, 2184-2188.) The endogenous peptides themselves have 36% of residues in common and ghrelin was even identified at one point as motilin-related peptide. (Tomasetto, C.; Karam, S. M.; Ribieras, S.; Masson, R.; Lefebvre, O.; Staub, A.; Alexander, G.; Chenard, M. P.; Rio, M. C. Identification and characterization of a novel gastric peptide hormone: the motilin-related peptide. Gastroenterology 2000, 119, 395-405.) Ghrelin does not interact appreciably at the motilin receptor, although GHRP-6 does. (Depoortere, I.; Thijs, T.; Thielemans, L.; Robberecht, P.; Peeters, T. L. Interaction of the growth hormone-releasing peptides ghrelin and growth hormone-releasing peptide-6 with the motilin receptor in the rabbit gastric antrum. J. Pharmacol. Exp. Ther. 2003, 305, 660-667.) On the other hand, motilin itself as been demonstrated to have some GH-releasing effects. (Samson, W. K.; Lumpkin, M. D.; Nilayer, G.; McCann, S. M. Motilin: a novel growth hormone releasing agent. Brain Res. Bull. 1984, 12, 57-62.)

A wider evaluation of receptor selectivity can be obtained through the use of "ExpresSProfile", a broad target screen offered commercially by CEREP (Poitiers, France). In this screen, a single-point (10 µM) binding assay is performed across 50 individual receptors from four distinct target classes: non-peptide G-Protein Coupled Receptors (GPCRs), peptide GPCRs, ion channels and amine transporters.

C. Cell Culture Assay for Growth Hormone Release

Cell culture assays for determining growth hormone release can be employed as described in Cheng, et al. Endocrinology 1989, 124, 2791-2798. In particular, anterior pituitary glands are obtained from male Sprague-Dawley rats and placed in cold culture medium. These pituitaries are sectioned, for example into one-eighth sections, then digested with trypsin. Cells are collected after digestion, pooled, and transferred into 24 well plates (minimum 200,000 cells per well). After a monolayer of cells has formed, generally after at least 4 d in culture, the cells are washed with medium prior to exposure to the test samples and controls. Varying concentrations of the test compounds and of ghrelin as a positive control were added to the medium. The cells are left for 15 min at 37° C., then the medium removed and the cells stored frozen. The amount of GH release was measured utilizing a standard radioimmunoassay as known to those in the art.

D. Gastric Emptying

A variety of methods and animal models can be used to investigate the effects of the test compounds on gastric emptying. (Fukuda, H.; Mizuta, Y.; Isomoto, H.; Takeshima, F.; Ohnita, K.; Ohba, K.; Omagari, K.; Taniyama, K.; Kohno, S. Ghrelin enhances gastric motility through direct stimulation of intrinsic neural pathways and capsaic insensitive afferent neurones in rats. Scand. J. Gastroenterol. 2004, 39, 1209-1214; Edholm, T.; Levin, F.; Hellström, P. M.; Schmidt, P. T. Ghrelin stimulates motility in the small intestine of rats through intrinsic cholinergic neurons. Regul. Pept. 2004, 121, 25-30; Levin, F.; Edholm, T.; Ehrstroem, M.; Wallin, B.; Schmidt, P. T.; Kirchgessner, A. M.; Hilsted, L. M.; Hellstrom, P. M.; Naeslund, E. Effect of peripherally administered ghrelin on gastric emptying and acid secretion in the rat. Regul. Pept. 2005, 131, 59-65; Tebbe, J. J.; Mronga, S.; Tebbe, C. G.; Ortmann, E.; Arnold, R.; Schaefer, M. K.-H. Ghrelin-induced stimulation of colonic propulsion is dependent on hypothalamic neuropeptide Y1- and corticotropin-releasing factor 1 receptor activation. J. Neuroendocrinol. 2005, 17, 570-576; Bassil, A. K.; Dass, N. B.; Murray, C. D.; Muir, A.; Sanger, G. J. Prokineticin-2, motilin, ghrelin and metoclopramide: prokinetic utility in mouse stomach and colon. Eur. J. Pharmacol. 2005, 524, 138-144; Depoortere, I.; DeWinter, B.; Thijs, T.; DeMan, J.; Pelckmans, P.; Peeters, T. Comparison of the gastroprokinetic effects of ghrelin, GHRP-6 and motilin in rats in vivo and in vitro. Eur. J. Pharmacol. 2005, 515, 160-168.)

To examine the effects of compounds of the invention in a model for gastroparesis, compounds were evaluated for possible effects on gastric emptying in fasted rats as described below.

Test Substances and Dosing Pattern

GHRP-6 and test samples were dissolved in vehicle of 9% HPBCD/0.9% NaCl. Immediately following oral administration of methylcellulose (2%) containing phenol red (0.05%) (2 mL/rat), test substances or vehicle (9% HPBCD/0.9% NaCl) were each administered intravenously (i.v.) at a dosing volume of 5 mL/kg.

Animals

Male Wistar rats were provided by LASCO (A Charles River Licensee Corporation, Taiwan). Space allocation for 6 animals was 45×23×15 cm. Animals were housed in APEC® cages and maintained in a controlled temperature (22° C.-24° C.) and humidity (60%-80%) environment with 12 h light, 12 h dark cycles for at least one week in the laboratory prior to being used. Free access to standard lab chow for rats (Lab Diet, Rodent Diet, PMI Nutrition International, USA) and tap water was granted. All aspects of this work including housing, experimentation and disposal of animals were performed in general accordance with the Guide for the Care and Use of Laboratory Animals (National Academy Press, Washington, D.C., 1996).

Chemicals

Glucose (Sigma, USA), Metoclopramide-HCl (Sigma, USA), Methylcellulose (Sigma, USA), NaOH (Sodium Hydroxide, Wako, Japan), Pyrogen free saline (Astar, Taiwan), Phenol Red-Sodium salt (Sigma, USA) and Trichloroacetic acid (Merck, USA).

Equipment 8-well strip (Costar, USA), 96-well plate (Costar, USA), Animal case (ShinTeh, R. O. C.), Centrifugal separator (Kokusan, H-107, Japan), Glass syringe (1 mL, 2 mL, Mitsuba, Japan), Hypodermic needle (25G×1", TOP Corporation, Japan), Microtube (Treff, Switzerland), pH-meter (Hanna, USA), Pipetman (P100, Gilson, France), Pipette tips (Costar, USA), Rat oral needle (Natsume, Japan), Spectra Fluor plus (Austria), Stainless scissors (Klappencker, Germany) and Stainless forceps (Klappencker, Germany).

Assay

Test substances were each administered intravenously to a group of 5 O/N-fasted Wistar derived male rats weighing 200±20 g immediately after methylcellulose (2%) containing phenol red (0.05%) was administered orally at 2 mL/animal. The animals were then sacrificed 15 minutes later. The stomach was immediately removed, homogenized in 0.1 N NaOH (5 mL) and centrifuged. Following protein precipitation by 20% trichloroacetic acid (0.5 mL) and re-alkalization of the supernatant with 0.1 N NaOH, total phenol red remaining in the stomach was determined by a colorimetric method at 560 nm. A 30 percent or more ($\geq$30%) increase in gastric emptying, detected as the decrease in phenol red concentration in the stomach relative to the vehicle control group, is considered significant.

Figure 2:
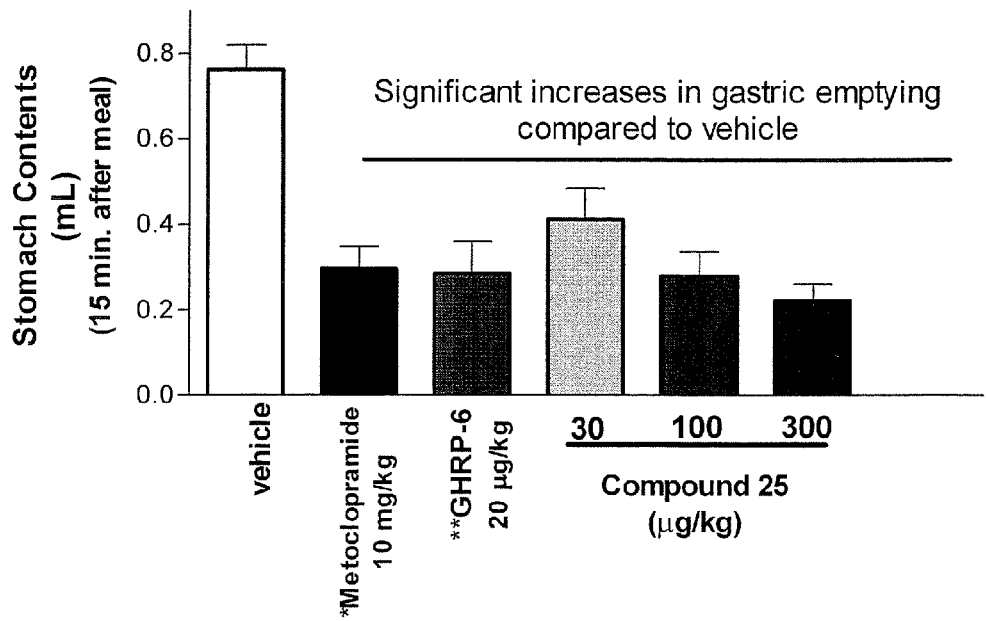
FIG. 2 (panels A and B) shows graphs presenting effects on gastric emptying for exemplary compounds of the present invention.
Figure 2:
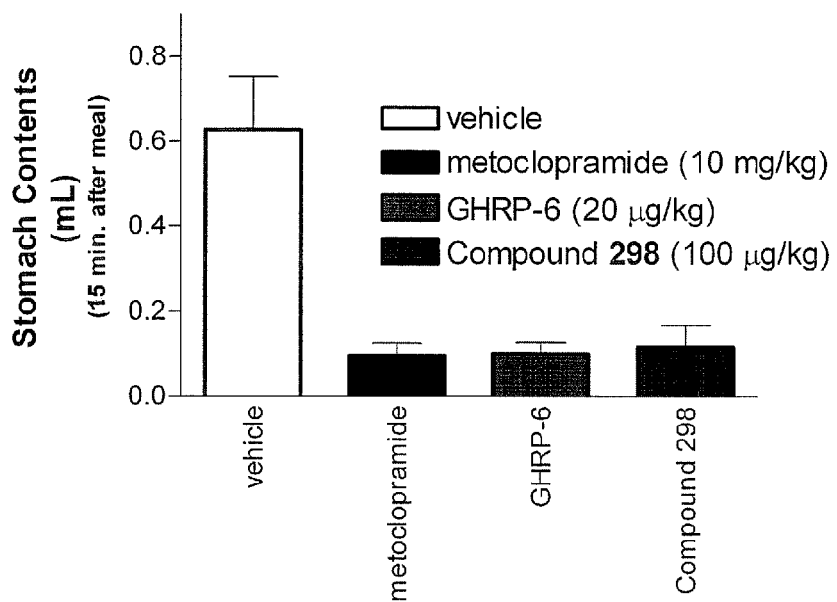

Results for two representative compounds of the invention are shown in FIG. 2 and presented in the Examples below.

E. Gastric Emptying and Intestinal Transit in Rat Model of Postoperative Ileus

This clinically relevant model for POI is adapted from that of Kalff. (Kalff, J. C.; Schraut, W. H.; Simmons, R. L.; Bauer, A. J. Surgical manipulation of the gut elicits an intestinal muscularis inflammatory response resulting in postsurgical ileus. Ann. Surg. 1998, 228, 652-663.) Other known models can also be used to study the effect of compounds of the invention. (Trudel, L.; Bouin, M.; Tomasetto, C.; Eberling, P.; St-Pierre, S.; Bannon, P.; L'Heureux, M. C.; Poitras, P. Two new peptides to improve post-operative gastric ileus in dog. Peptides 2003, 24, 531-534; Trudel, L.; Tomasetto, C.; Rio, M. C.; Bouin, M.; Plourde, V.; Eberling, P.; Poitras, P. Ghrelin/motilin-related peptide is a potent prokinetic to reverse gastric postoperative ileus in rats. Am. J. Physiol. 2002, 282, G948-G952.)

Animals
1. Rat, Sprague-Dawley, male, ~300 g.
2. Fasted O/N prior to study.

Induction of post-operative ileus (POI)
1. Isofluorane anaesthesia under sterile conditions.
2. Midline abdominal incision.
3. Intestines and caecum were eviscerated and kept moist with saline.
4. The intestines and caecum were manipulated along its entire length with moist cotton applicators analogous to the 'running of the bowel' in the clinical setting. This procedure was timed to last for 10 min.
5. Intestines were gently replaced into the abdomen and the abdominal wound was stitched closed under sterile conditions.

Dosing
1. Rat was allowed to recover from isofluorane anaesthesia.
2. Test compounds (or vehicle) were administered intravenously via previously implanted jugular catheter.
3. Immediate intragastric gavage of methylcellulose (2%) labeled with radioactive $^{99m}$Tc, t=0.

Experimental
1. At t=15 min, animal was euthanized with $CO_2$.
2. Stomach and 10 cm sections along the small intestine were immediately ligated, cut and placed in tubes for measuring of $^{99m}$Tc in gamma counter.
3. Stomach emptying and small intestinal transit were measured by calculation of the geometric mean.

Geometric mean=$\Sigma$(% total radioactivity×number of segment)/100

Figure 3:
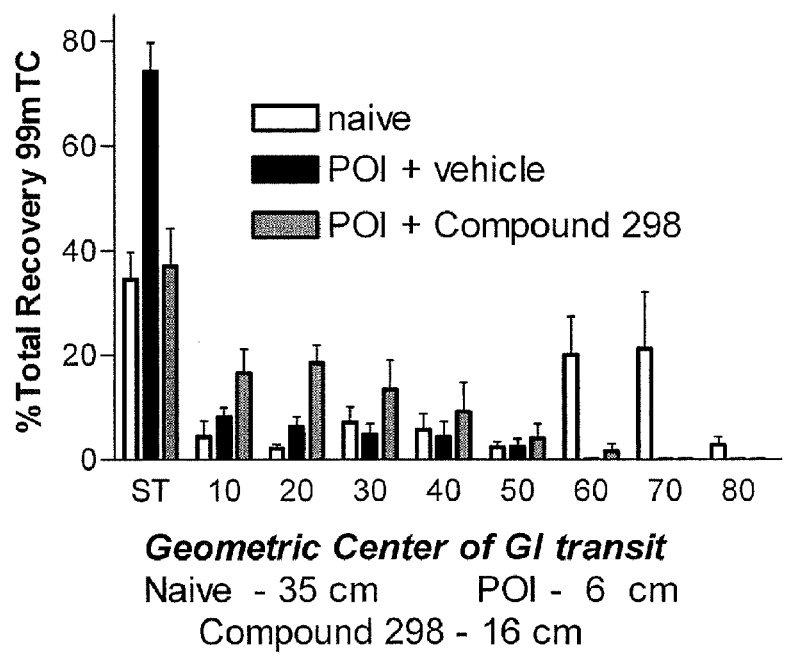
FIG. 3 shows a graph presenting effects on meal transit in an animal model of postoperative ileus for an exemplary compound of the present invention.
Figure 4:
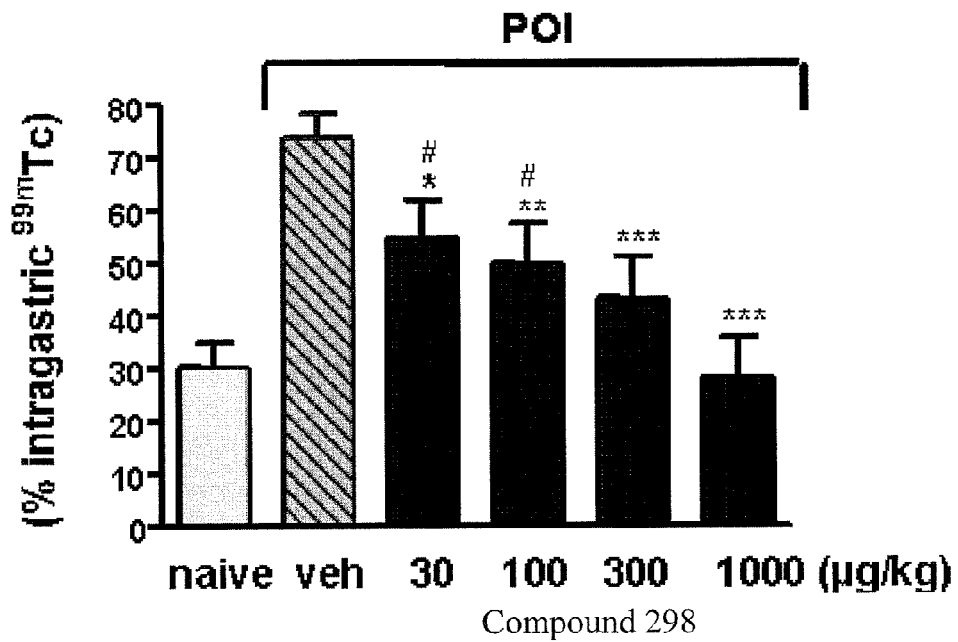
FIG. 4 shows a graph presenting effects on gastric emptying in an animal model of postoperative ileus for an exemplary compound of the present invention.

Results for a representative compound of the invention are depicted in the graph in FIGS. 3 and 4. Further results are presented in the Examples below.

F. Growth Hormone Response to Test Compounds

The compounds of the invention likewise can be tested in a number of animal models for their effect on GH release. For example, rats (Bowers, C. Y.; Momany, F.; Reynolds, G. A.; Chang, D.; Hong, A.; Chang, K. Endocrinology 1980, 106, 663-667), dogs (Hickey, G.; Jacks, T.; Judith, F.; Taylor, J.; Schoen, W. R.; Krupa, D.; Cunningham, P.; Clark, J.; Smith, R. G. Endocrinology 1994, 134, 695-701; Jacks, T.; Hickey, G.; Judith, F.; Taylor, J.; Chen, H.; Krupa, D.; Feeney, W.; Schoen, W. R.; Ok, D.; Fisher, M.; Wyvratt, M.; Smith, R. J. Endocrinology 1994, 143, 399-406; Hickey, G. J.; Jacks, T. M.; Schleim, K. D.; Frazier, E.; Chen, H. Y.; Krupa, D.; Feeney, W.; Nargund, R. P.; Patchett, A. A.; Smith, R. G. J. Endocrinol. 1997, 152, 183-192), and pigs (Chang, C. H.; Rickes, E. L.; Marsilio, F.; McGuire, L.; Cosgrove, S.; Taylor, J.; Chen, H. Y.; Feighner, S.; Clark, J. N.; Devita, R.; Schoen, W. R.; Wyvratt, M.; Fisher, M.; Smith, R. G.; Hickey, G. Endocrinology 1995, 136, 1065-1071; Peschke, B.; Hanse, B. S. Bioorg. Med. Chem. Lett. 1999, 9, 1295-1298) have all been successfully utilized for the in vivo study of the effects of GHS and would likewise be applicable for investigation of the effect of ghrelin agonists on GH levels. The measurement of ghrelin of GH levels in plasma after appropriate administration of compounds of the invention can be performed using radioimmunoassay via standard methods known to those in the art. (Deghenghi, R.; et al. Life Sciences 1994, 54, 1321-

1328.) Binding to tissue can be studied using whole body autoradiography after dosing of an animal with test substance containing a radioactive label. (Ahnfelt-Ronne, I.; Nowak, J.; Olsen, U. B. Do growth hormone-releasing peptides act as ghrelin secretagogues? Endocrine 2001, 14, 133-135.)

The following method is employed to determine the temporal pattern and magnitude of the growth hormone (GH) response to test compounds, administered either systemically or centrally.

Dosing and Sampling Procedures for In Vivo Studies of GH Release

Adult male Sprague Dawley rats (225-300 g) were purchased from Charles River Canada (St. Constant, Canada) and individually housed on a 12-h light, 12-h dark cycle (lights on, time: 0600-1800) in a temperature (22±1° C.)— and humidity-controlled room. Purina rat chow (Ralston Purina Co., St. Louis, Mo.) and tap water were freely available. For these studies, chronic intracerebroventricular (icv) and intracardiac venous cannulas were implanted under sodium pentobarbital (50 mg/kg, ip) anesthesia using known techniques. The placement of the icv cannula was verified by both a positive drinking response to icv carbachol (100 ng/10 µl) injection on the day after surgery and methylene blue dye at the time of sacrifice. After surgery, the rats were placed directly in isolation test chambers with food and water freely available until body weight returned to preoperative levels (usually within 5-7 d). During this time, the rats were handled daily to minimize any stress associated with handling on the day of the experiment. On the test day, food was removed 1.5 h before the start of sampling and was returned at the end. Free moving rats were iv injected with either test sample at various levels (3, 30, 300, 1000 µg/kg) or normal saline at two different time points during a 6-h sampling period. The times 1100 and 1300 were chosen because they reflect typical peak and trough periods of GH secretion, as previously documented. The human ghrelin peptide (5 µg, Phoenix Pharmaceuticals, Inc., Belmont, Calif.) was used as a positive control in the experiments and was diluted in normal saline just before use. To assess the central actions of test compounds on pulsatile GH release, a 10-fold lower dose of the test sample or normal saline was administered icv at the same time points, 1100 and 1300. Blood samples (0.35 mL) were withdrawn every 15 min over the 6-h sampling period (time: 1000-1600) from all animals. To document the rapidity of the GH response to the test compound, an additional blood sample was obtained 5 min after each injection. All blood samples were immediately centrifuged, and plasma was separated and stored at −20° C. for subsequent GH assay. To avoid hemodynamic disturbance, the red blood cells were resuspended in normal saline and returned to the animal after removal of the next blood sample. All animal studies were conducted under procedures approved by an animal care oversight committee.

GH Assay Method

Plasma GH concentrations were measured in duplicate by double antibody RIA using materials supplied by the NIDDK Hormone Distribution Program (Bethesda, Md.). The averaged plasma GH values for 5-6 rats per group are reported in terms of the rat GH reference preparation. The standard curve was linear within the range of interest; the least detectable concentration of plasma GH under the conditions used was approximately 1 ng/mL. All samples with values above the range of interest were reassayed at dilutions ranging from 1:2 to 1:10. The intra- and interassay coefficients of variation were acceptable for duplicate samples of pooled plasma containing a known GH concentration.

G. Animal model of Opioid-Induced Bowel Dysfunction

Opioid analgesics, such as morphine, are well known to delay gastrointestinal transit, which is a noted side effect for this class of drugs. (Greenwood-van Meerveld, B.; Gardner, C. J.; Little, P. J.; Hicks, G. A.; DeHaven-Hudkins, D. L. Preclinical studies of opioids and opioid antagonists on gastrointestinal function. Neurogastroenterol. Motil. 2004, 16, 46-53.) The clinical term for this syndrome is opioid-induced bowel dysfunction (OBD). The aim of this study was to determine whether test compounds can effectively reverse morphine-induced delayed gastric emptying and small intestinal transit in a rat model of opioid-induced bowel dysfunction.

Experimental Methods

Figure 5:
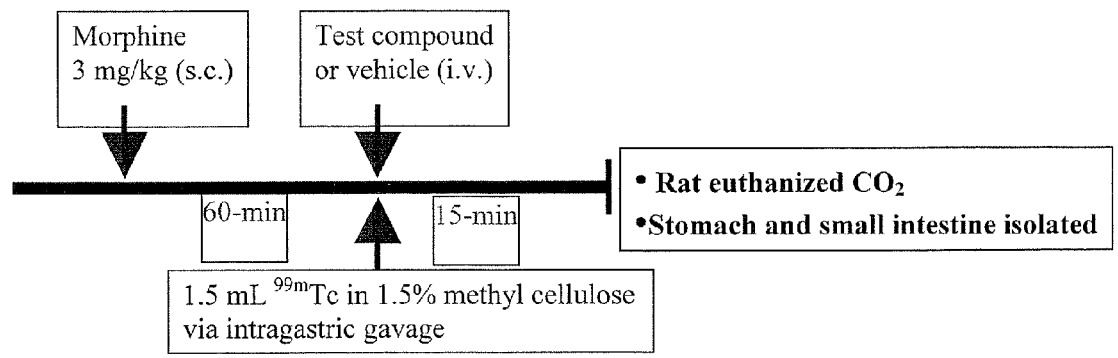
FIG. 5 shows a graphic representation of the experimental design for the study of opioid-induced bowel dysfunction.

1. Rats (male, Sprague-Dawley, 250-300 g, N=6-7/gp) were implanted with jugular vein catheters to accommodate dosing of test articles.
2. Overnight-fasted rats were administered morphine by sub-cutaneous injection (3 mg/kg).
3. After 60 minutes, rats were dosed (i.v. bolus) with vehicle, test compound (0.30, 1.0 mg/kg) or GHRP-6 (0.02 mg/kg) followed by intragastric gavage of $^{99m}$Tc methylcellulose (2%) meal.
4. After 15 minutes, the rats were euthanized and the stomach and consecutive 10 cm segments of the intestine are isolated. Radioactivity ($^{99m}$Tc) in each tissue isolate is measured as a means of measuring gastric emptying and small intestinal transit.
5. One-way ANOVA, Dunnet's post-hoc statistical test was applied.
6. The experimental design for the study is shown in FIG. 5.

Figure 6:
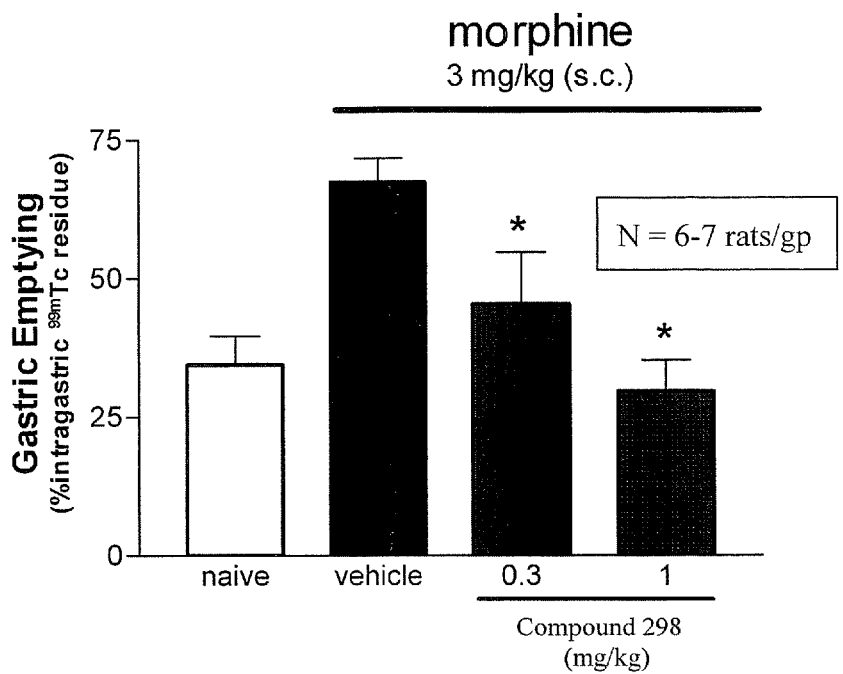
FIG. 6 shows a graph presenting effects on gastric emptying in an animal model of opioid-induced bowel dysfunction for an exemplary compound of the present invention.

Results for a representative compound of the invention are depicted in the graph in FIG. 6.

H. Gastroparesis Animal Model

High caloric meals are well known to impede gastric emptying. This observation has recently been exploited by Megens, A. A.; et al. (unpublished) to develop a rat model for delayed gastric emptying as experienced in gastroparesis. Such a model can be employed to demonstrate the utility of the compounds of the invention for the prevention and/or treatment of gastroparesis.

Materials

1. Wistar rats, male, 200-250 g
2. Chocolate test meal: 2 mL Clinutren ISO® (1.0 kcal/mL, Nestle SA, Vevey Switzerland)

Method

The test meal was given to the subjects by oral gavage at time=0. After 60 min, the subjects were sacrificed, the stomachs excised and the contents weighed. Untreated animals experienced a significant delay in gastric emptying as denoted by the higher residual stomach content.

Test compounds were administered intravenously as aqueous solutions, or solutions in normal saline, at time=0 at three dose levels (0.08 mg/kg; 0.30-0.31 mg/kg, 1.25 mg/kg). When necessary, for example compounds 21, 299 and 415, 10% cyclodextrin (CD) was added to solubilize the material. Test compounds examined utilizing subcutaneous injection are administered at time=−30 min. Four to five (4-5) rats were tested per group, except in the case of the cyclodextrin control in which ten (10) rats comprised the group.

Results were typically reported as percentage relative to the stomach weight for injection only of solvent as a control and illustrate the gastric emptying capability of the compounds of the present invention.

I. Combination Animal Model of Postoperative Ileus and Opioid-Induced Bowel Dysfunction Post-operative ileus patients are typically prescribed opioid analgesics for the treatment of post-surgical pain. Unfortunately, a well-known side effect of the opioid analgesics is to exacerbate the underlying ileus. The aim of this study was to determine whether a representative compound of the invention is effective in a POI-rat model concurrently dosed with typical opioid analgesics such as morphine.

Experimental Methods

Figure 7:
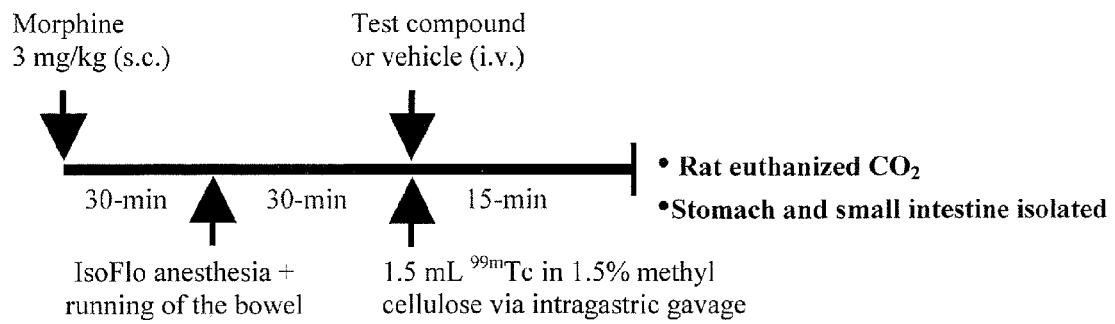
FIG. 7 shows a graphic representation of the experimental design for the combination study of post-operative ileus and opioid-induced bowel dysfunction.

1. POI model adapted from that of Kalff (Kalff, J. C.; Schraut, W. H.; Simmons, R. L.; Bauer, A. J. Surgical manipulation of the gut elicits an intestinal muscularis inflammatory response resulting in postsurgical ileus. Ann. Surg. 1998, 228, 652-663.) as described in Example F above.
2. Rats (male, Sprague-Dawley, 250-300 g, N=6-8/group) were implanted with jugular vein catheters to accommodate dosing of test articles.
3. Rats were fasted overnight, then dosed (s.c.) with morphine (3 mg/kg).
4. After 30 minutes, the rats were anesthetized with isoflurane and subjected to abdominal surgery.
5. Following an abdominal incision, the small intestine caecum and large intestine were eviscerated for a period of 15 minutes and kept moist with saline.
6. A "running of the bowel" was performed, a clinically-relevant manipulation of the intestines characterized by first pinching the upper small intestine and continuing this manipulation down through the large intestine.
7. 30 minutes after initial anesthesia, the rats are dosed (i.v. bolus) with vehicle or test compound (0.3, 1, 3 mg/kg) immediately after intragastric gavage of $^{99m}$Tc methylcellulose (2%) meal.
8. 15 minutes after the meal, the rats were euthanized and the stomach and consecutive 10 cm segments of the intestine were isolated. Radioactivity ($^{99m}$Tc) in each tissue isolate was measured to evaluate gastric emptying and small intestinal transit as previously described.
9. The experimental design for this study is depicted in FIG. 7.

Figure 8:
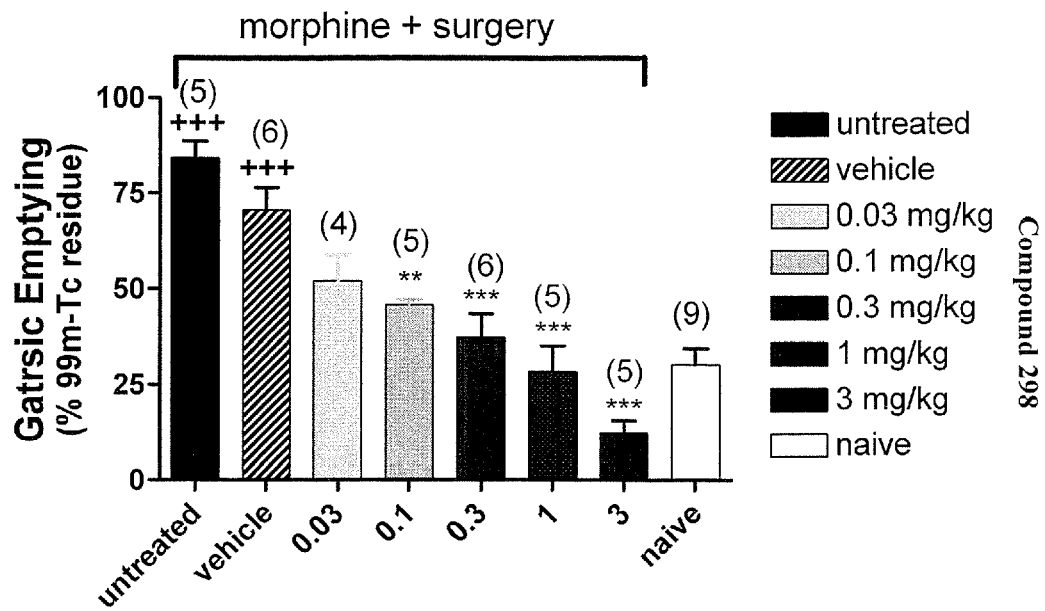
FIG. 8 shows a graph presenting effects on gastric emptying in a combination animal model of post-operative ileus and opioid-induced bowel dysfunction for an exemplary compound of the present invention.
Figure 9:
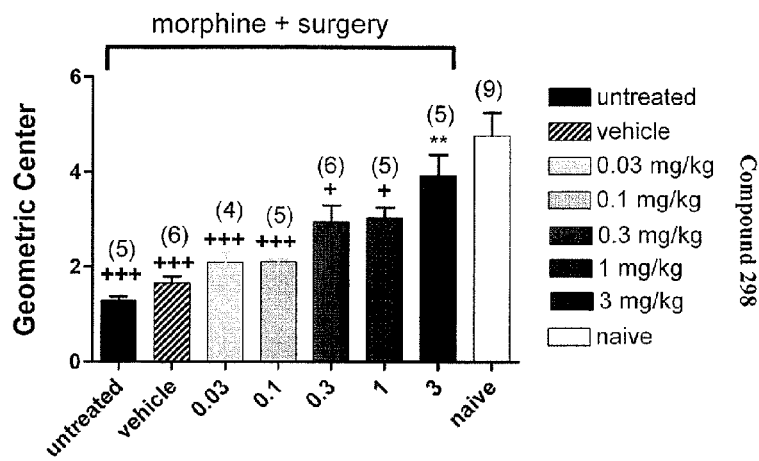
FIG. 9 (panels A and B) shows a graph presenting effects on meal transit in the combination animal model of post-operative ileus and opioid-induced bowel dysfunction for an exemplary compound of the present invention.
Figure 9:
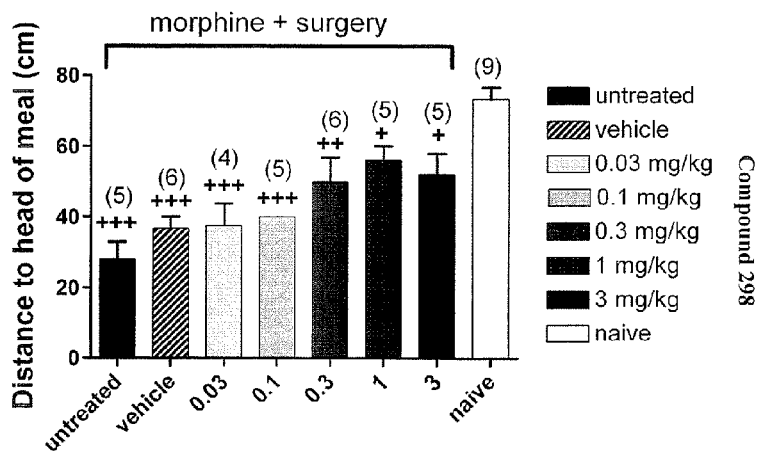

Results for a representative compound of the invention are depicted in FIGS. 8 and 9.

4. Pharmaceutical Compositions

The macrocyclic compounds of the present invention or pharmacologically acceptable salts thereof according to the invention may be formulated into pharmaceutical compositions of various dosage forms. To prepare the pharmaceutical compositions of the invention, one or more compounds, including optical isomers, enantiomers, diastereomers, racemates or stereochemical mixtures thereof, or pharmaceutically acceptable salts thereof as the active ingredient is intimately mixed with appropriate carriers and additives according to techniques known to those skilled in the art of pharmaceutical formulations.

A pharmaceutically acceptable salt refers to a salt form of the compounds of the present invention in order to permit their use or formulation as pharmaceuticals and which retains the biological effectiveness of the free acids and bases of the specified compound and that is not biologically or otherwise undesirable. Examples of such salts are described in Handbook of Pharmaceutical Salts: Properties, Selection, and Use, Wermuth, C. G. and Stahl, P. H. (eds.), Wiley-Verlag Helvetica Acta, Ztirich, 2002 [ISBN 3-906390-26-8]. Examples of such salts include alkali metal salts and addition salts of free acids and bases. Examples of pharmaceutically acceptable salts, without limitation, include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, xylenesulfonates, phenylacetates, phenylpropionates, phenylbutyrates, citrates, lactates, γ-hydroxybutyrates, glycollates, tartrates, methanesulfonates, ethane sulfonates, propanesulfonates, toluenesulfonates, naphthalene-1-sulfonates, naphthalene-2-sulfonates, and mandelates.

If an inventive compound is a base, a desired salt may be prepared by any suitable method known to those skilled in the art, including treatment of the free base with an inorganic acid, such as, without limitation, hydrochloric acid, hydrobromic acid, hydroiodic, carbonic acid, sulfuric acid, nitric acid, phosphoric acid, and the like, or with an organic acid, including, without limitation, formic acid, acetic acid, propionic acid, maleic acid, succinic acid, mandelic acid, fumaric acid, malonic acid, pyruvic acid, oxalic acid, stearic acid, ascorbic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, 2-hydroxyethanesulfonic acid, benzenesulfonic acid, cyclohexyl-aminosulfonic acid or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine, lysine and arginine; ammonia; primary, secondary, and tertiary amines such as ethylenediamine, N,N'-dibenzylethylenediamine, diethanolamine, choline, and procaine, and cyclic amines, such as piperidine, morpholine, and piperazine; as well as inorganic salts derived from sodium, calcium, potassium, magnesium, manganese, iron, copper, zinc, aluminum, and lithium.

The carriers and additives used for such pharmaceutical compositions can take a variety of forms depending on the anticipated mode of administration. Thus, compositions for oral administration may be, for example, solid preparations such as tablets, sugar-coated tablets, hard capsules, soft capsules, granules, powders and the like, with suitable carriers and additives being starches, sugars, binders, diluents, granulating agents, lubricants, disintegrating agents and the like. Because of their ease of use and higher patient compliance, tablets and capsules represent the most advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like. Typical preparations for parenteral administration comprise the active ingredient with a carrier such as sterile water or parenterally acceptable oil including polyethylene glycol, polyvinyl pyrrolidone, lecithin, arachis oil or sesame oil, with other additives for aiding solubility or preservation may also be included. In the case of a solution, it can be lyophilized to a powder and then reconstituted immediately prior to use. For dispersions and suspensions, appropriate carriers and additives include aqueous gums, celluloses, silicates or oils.

The pharmaceutical compositions according to embodiments of the present invention include those suitable for oral, rectal, topical, inhalation (e.g., via an aerosol) buccal (e.g., sub-lingual), vaginal, topical (i.e., both skin and mucosal surfaces, including airway surfaces), transdermal administration and parenteral (e.g., subcutaneous, intramuscular, intradermal, intraarticular, intrapleural, intraperitoneal, intrathecal, intracerebral, intracranially, intraarterial, or intravenous), although the most suitable route in any given case will depend on the nature and severity of the condition being treated and on the nature of the particular active agent which is being used.

Compositions for injection will include the active ingredient together with suitable carriers including propylene glycol-alcohol-water, isotonic water, sterile water for injection (USP), emulPhor™-alcohol-water, cremophor-EL™ or other suitable carriers known to those skilled in the art. These earners may be used alone or in combination with other conventional solubilizing agents such as ethanol, propylene glycol, or other agents known to those skilled in the art.

Where the macrocyclic compounds of the present invention are to be applied in the form of solutions or injections, the compounds may be used by dissolving or suspending in any conventional diluent. The diluents may include, for example, physiological saline, Ringer's solution, an aqueous glucose solution, an aqueous dextrose solution, an alcohol, a fatty acid ester, glycerol, a glycol, an oil derived from plant or animal sources, a paraffin and the like. These preparations may be prepared according to any conventional method known to those skilled in the art.

Compositions for nasal administration may be formulated as aerosols, drops, powders and gels. Aerosol formulations typically comprise a solution or fine suspension of the active ingredient in a physiologically acceptable aqueous or non-aqueous solvent. Such formulations are typically presented in single or multidose quantities in a sterile form in a sealed container. The sealed container can be a cartridge or refill for use with an atomizing device. Alternatively, the sealed container may be a unitary dispensing device such as a single use nasal inhaler, pump atomizer or an aerosol dispenser fitted with a metering valve set to deliver a therapeutically effective amount, which is intended for disposal once the contents have been completely used. When the dosage form comprises an aerosol dispenser, it will contain a propellant such as a compressed gas, air as an example, or an organic propellant including a fluorochlorohydrocarbon or fluorohydrocarbon.

Compositions suitable for buccal or sublingual administration include tablets, lozenges and pastilles, wherein the active ingredient is formulated with a carrier such as sugar and acacia, tragacanth or gelatin and glycerin.

Compositions for rectal administration include suppositories containing a conventional suppository base such as cocoa butter.

Compositions suitable for transdermal administration include ointments, gels and patches.

Other compositions known to those skilled in the art can also be applied for percutaneous or subcutaneous administration, such as plasters.

Further, in preparing such pharmaceutical compositions comprising the active ingredient or ingredients in admixture with components necessary for the formulation of the compositions, other conventional pharmacologically acceptable additives may be incorporated, for example, excipients, stabilizers, antiseptics, wetting agents, emulsifying agents, lubricants, sweetening agents, coloring agents, flavoring agents, isotonicity agents, buffering agents, antioxidants and the like. As the additives, there may be mentioned, for example, starch, sucrose, fructose, dextrose, lactose, glucose, mannitol, sorbitol, precipitated calcium carbonate, crystalline cellulose, carboxymethylcellulose, dextrin, gelatin, acacia, EDTA, magnesium stearate, talc, hydroxypropylmethylcellulose, sodium metabisulfite, and the like.

In some embodiments, the composition is provided in a unit dosage form such as a tablet or capsule.

In further embodiments, the present invention provides kits including one or more containers comprising pharmaceutical dosage units comprising an effective amount of one or more compounds of the present invention.

The present invention further provides prodrugs comprising the compounds described herein. The term "prodrug" is intended to mean a compound that is converted under physiological conditions or by solvolysis or metabolically to a specified compound that is pharmaceutically active. The "prodrug" can be a compound of the present invention that has been chemically derivatized such that, (i) it retains some, all or none of the bioactivity of its parent drug compound, and (ii) it is metabolized in a subject to yield the parent drug compound. The prodrug of the present invention may also be a "partial prodrug" in that the compound has been chemically derivatized such that, (i) it retains some, all or none of the bioactivity of its parent drug compound, and (ii) it is metabolized in a subject to yield a biologically active derivative of the compound. Known techniques for derivatizing compounds to provide prodrugs can be employed. Such methods may utilize formation of a hydrolyzable coupling to the compound.

The present invention further provides that the compounds of the present invention may be administered in combination with a therapeutic agent used to prevent and/or treat metabolic and/or endocrine disorders, gastrointestinal disorders, cardiovascular disorders, obesity and obesity-associated disorders, central nervous system disorders, genetic disorders, hyperproliferative disorders and inflammatory disorders. Exemplary agents include analgesics (including opioid analgesics), anesthetics, antifungals, antibiotics, antiinflammatories (including nonsteroidal anti-inflammatory agents), anthelmintics, antiemetics, antihistamines, antihypertensives, antipsychotics, antiarthritics, antitussives, antivirals, cardioactive drugs, cathartics, chemotherapeutic agents (such as DNA-interactive agents, antimetabolites, tubulin-interactive agents, hormonal agents, and agents such as asparaginase or hydroxyurea), corticoids (steroids), antidepressants, depressants, diuretics, hypnotics, minerals, nutritional supplements, parasympathomimetics, hormones (such as corticotrophin releasing hormone, adrenocorticotropin, growth hormone releasing hormone, growth hormone, thyrptropin-releasing hormone and thyroid stimulating hormone), sedatives, sulfonamides, stimulants, sympathomimetics, tranquilizers, vasoconstrictors, vasodilators, vitamins and xanthine derivatives.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, and for drug screening and drug development purposes.

In therapeutic use for treatment of conditions in mammals (i.e. humans or animals) for which a modulator, such as an agonist, of the ghrelin receptor is effective, the compounds of the present invention or an appropriate pharmaceutical composition thereof may be administered in an effective amount. Since the activity of the compounds and the degree of the therapeutic effect vary, the actual dosage administered will be determined based upon generally recognized factors such as age, condition of the subject, route of delivery and body weight of the subject. The dosage can be from about 0.1 to about 100 mg/kg, administered orally 1-4 times per day. In addition, compounds can be administered by injection at approximately 0.01-20 mg/kg per dose, with administration 1-4 times per day. Treatment could continue for weeks, months or longer. Determination of optimal dosages for a particular situation is within the capabilities of those skilled in the art.

5. Methods of Use

The compounds of formula I, II, III and/or IV of the present invention can be used for the prevention and treatment of a range of gastrointestinal disorders including postoperative ileus, gastroparesis, opioid-induced bowel dysfunction, short bowel syndrome, chronic intestinal pseudo-obstruction, irritable bowel syndrome (IBS), non-ulcer dyspepsia, Crohn's disease, gastroesophogeal reflux disorders, constipation, ulcerative colitis, pancreatitis, infantile hypertrophic pyloric stenosis, carcinoid syndrome, malabsorption syndrome, diarrhea, diabetes including diabetes mellitus (type II diabetes), obesity, atrophic colitis, gastritis, gastric stasis, gastrointestinal dumping syndrome, postgastroenterectomy syndrome, celiac disease, an eating disorder or obesity.

According to a further aspect of the invention, there is provided a method for the treatment of multiple gastrointestinal disorders including post-operative ileus, gastroparesis, such as that resulting from type I or type II diabetes or surgery, opioid-induced bowel dysfunction, short bowel syndrome, gastrointestinal dumping syndrome, postgastroenterectomy syndrome, celiac disease and other gastrointestinal disorders, which method comprises administering to said patient an effective amount of at least one member selected from the compounds disclosed herein having the ability to modulate the ghrelin receptor.

In particular embodiments, the macrocyclic compounds of the present invention can be used to treat post-operative ileus in combination with opioid-induced bowel dysfunction. In other embodiments, the compounds of the present invention can be used to treat gastroparesis in combination with opioid-induced bowel dysfunction. In still other embodiments, the compounds of the present invention can be used to treat post-surgical gastroparesis in combination with opioid-induced bowel dysfunction.

In another embodiment, the compounds of the present invention can be used to treat post-surgical gastroparesis.

As used herein, "treatment" is not necessarily meant to imply cure or complete abolition of the disorder or symptoms associated therewith.

The compounds of the present invention can further be utilized for the preparation of a medicament for the treatment of a range of medical conditions involving gastrointestinal motility disorders.

Further embodiments of the present invention will now be described with reference to the following examples. It should be appreciated that these examples are for the purposes of illustrating embodiments of the present invention, and do not limit the scope of the invention.

A. Biological Results

1. Effect of Compounds 25 and 298 on Gastric Emptying of a Solid Meal in Naïve Rat Objectives
   1. To ascertain data for representative compounds 25 and 298 as prokinetic agents with potent effects on gastric emptying, a model for gastroparesis.

Methods
   1. Overnight-fasted rats (male, Wistar, ~200 g, N=5/group) were given a meal of methylcellulose (2%) by intragastric gavage. The meal was labeled with phenol red (0.05%).
   2. Test articles (i.e. vehicle, compound 25, compound 298, metoclopramide, GHRP-6, etc.) were administered by intravenous injection immediately after meal.
   3. Animals were sacrificed 15 minutes later; the stomach was immediately removed and homogenized in 0.1 N NaOH and centrifuged.
   4. Total phenol red remaining in the stomach was quantified by a colorimetric method at 560 nm.
   5. A >30% increase in gastric emptying, detected based on the phenol red concentration in comparison to the control group, is considered significant.

Results

Metoclopramide (marketed gastroparesis product) and GHRP-6 (reference peptide agonists at hGHS-R1a) all demonstrated significant gastric emptying in the assay. Compounds 25 and 298 at 100 µg/kg caused a significant increase ($\geqq$30%) in gastric emptying relative to the vehicle control group. The relative efficacy (39% increase) of compounds 25 and 298 at 100 µg/kg i.v. was similar to concurrently run positive reference agents GHRP-6 at 20 µg/kg i.v. (40% increase) and metoclopramide at 10 mg/kg i.v. (41% increase). Accordingly, compounds 25 and 298 at a dose of 100 µg/kg demonstrated gastrokinetic activity in rats, with efficiency similar to GHRP-6 at 20 µg/kg and metoclopramide at 10 mg/kg. Compound 25 also demonstrated significant gastric emptying at 30 µg/kg. Further, compounds 25 (FIG. 2A) and 298 (FIG. 2B) resulted in gastric emptying in a dose-dependent manner with ~100-fold greater potency compared to metoclopramide, a currently used drug with prokinetic activity, based on the different dose levels. This result show that these compounds are more potent than other compounds interacting at this receptor previously found to enhance GI motility, which were unable to promote gastric emptying at 100 µg/kg (U.S. Pat. No. 6,548,501).

2. Effect of Compound 298 in the Treatment of Post-operative Ileus in Rat Objective To measure the therapeutic utility of compound 298 in a rat model of post-operative ileus (POI).

Methods
   1. Model adapted from Kälff. (Kalff, J. C.; Schraut, W. H.; Simmons, R. L.; Bauer, A. J. Surgical manipulation of the gut elicits an intestinal muscularis inflammatory response resulting in postsurgical ileus. Ann. Surg. 1998, 228, 652-663.)
   2. Rats (male, Sprague-Dawley, 250-300 g) were implanted with jugular vein catheters to accommodate dosing of test articles.

3. Rats were fasted O/N, anesthetized with isofluorane and subjected to abdominal surgery.
4. Following an abdominal incision, the small intestine caecum and large intestine were eviscerated for a period of 15 min and kept moist with saline.
5. A "running of the bowel" was performed, a clinically-relevant manipulation of the intestines characterized by first pinching the upper small intestine and continuing this manipulation down through the large intestine.
6. Rats were allowed a 15 min recovery beginning after the disappearance of any effects of the isofluorane anesthesia.
7. Rats were dosed with vehicle or compound 298 (30, 100, or 300 μg/kg, i.v., N=6/gp) followed by intragastric gavage of $^{99m}$Tc methylcellulose (2%) meal.
8. After 15 min, the rats were euthanized and the stomach and consecutive 10 cm segments of the intestine were isolated. Radioactivity ($^{99m}$Tc) in each tissue isolate was measured as a means of measuring the transit of the meal.

Results

In FIG. 3, the distribution of the bars indicates the distribution of the meal in the stomach ('ST') and consecutive 10 cm segments of the small intestine at 15 min post-oral gavage. Abdominal surgery coupled with a running of the bowel caused a significant ileus in rats as determined by comparison of the naïve (i.e. unoperated) and POI treatment groups. Compound 298 significantly increased gastric emptying and intestinal transit at test concentrations of 100 and 300 μg/kg (i.v.). The data corresponding to the 100 μg/kg dose is presented in FIG. 3. At 100 μg/kg (i.v.), compound 298 significantly promoted GI transit by 2.7× as measured by the geometric center of the meal in comparison to the POI+vehicle treatment group. FIG. 4 shows that even at doses as low as 30 μg/kg, compound 298 has an effect at improving gastric emptying in this model. Compound 298 improved gastric emptying and intestinal transit in rats with post-operative ileus. Compound 298 can treat an existing, post-surgical ileus; thus, prophylactic use prior to surgery can be employed, but is not required, as is the case for some, if not all, opioid antagonists currently in clinical development. (Greenwood-van Meerveld, B.; Gardner, C. J.; Little, P. J.; Hicks, G. A.; DeHaven-Hudkins, D. L. Preclinical studies of opioids and opioid antagonists on gastrointestinal function. Neurogastroenterol. Motil. 2004, 16, 46-53; Leslie, J. B. Alvimopan for the management of postoperative ileus. Ann. Pharmacother. 2005, 39, 1502-1510; Yuan, C.-S.; Israel, R. J. Methylnaltrexone, a novel peripheral opioid antagonist for the treatment of opioid side effects. Exp. Opin. Invest. Drugs 2006, 15, 541-552.)

3. Effect of Compound 298 on Gastric Emptying and Gastrointestinal Transit in a Model of Opioid-Delayed Gastric Emptying Opioid analgesics, such as morphine, are well known to delay gastrointestinal transit which is an important side-effect for this class of drugs. The clinical term for this syndrome is opioid bowel dysfunction (OBD). Importantly, patients recovering from abdominal surgery experience post-operative ileus that is further exacerbated by concomitant opioid therapy for post-surgical pain.

Objective
1. To determine whether compounds of the invention as represented by compound 298, may have therapeutic utility in the treatment of OBD.

Methods
1. Rats (male, Sprague-Dawley, 250-300 g) were implanted with jugular vein catheters to accommodate dosing of test articles.
2. Overnight-fasted rats were administered morphine (3 mg/kg s.c.).
3. After 60 min, rats were to be dosed with vehicle or compound 298 (300 or 1000 μg/kg, i.v., n=4-to-6/gp) followed by intragastric gavage of $^{99m}$Tc methylcellulose (2%) meal.
4. After 15 min, the rats were euthanized and the stomach and consecutive 10 cm segments of the intestine are isolated. Radioactivity ($^{99m}$Tc) in each tissue isolate was measured as a means of measuring the transit of the meal.
5. The experimental design is shown in FIG. 5.

Results

A preliminary study demonstrated that morphine (3 mg/kg, s.c.) significantly delayed gastric emptying and small intestinal transit in rats. Compound 298 significantly accelerated opioid-delayed gastric emptying and opioid-delayed small intestinal gastrointestinal transit in a dose-dependent manner (Table 1, data presented as mean±sem).

TABLE 1

Effect of compound 298 on opioid-delayed gastrointestinal transit

| Treatment | Intragastric Residue (%) | Geometric Center |
|---|---|---|
| Naïve | 0.35 ± 0.05 | 4.55 ± 0.90 |
| Vehicle | 0.67 ± 0.04 | 1.79 ± 0.22 |
| TZP-101 (0.30 mg/kg) | 0.45 ± 0.09 | 3.23 ± 0.82 |
| TZP-101 (1.0 mg/kg) | 0.30 ± 0.06 | 3.73 ± 0.61 |
| GHRP-6 | 0.48 ± 0.10 | 3.38 ± 0.76 |

Compound 298 decreased intragastric residue and increased geometric center relative to the difference between the vehicle and blank controls at both 0.30 mg/kg and 1.0 mg/kg dose levels (FIG. 6).

4. Effect of Compound 298 in an Animal Model of Postoperative Ileus and Opioid-Induced Bowel Dysfunction Post-operative ileus patients are typically prescribed opioid analgesics for the treatment of post-surgical pain. A side effect of the opioid analgesics is to exacerbate the underlying ileus. The aim of this study was to demonstrate whether representative compound 298 is effective in a POI rat model concurrently dosed with a representative opioid analgesic, morphine.

Experimental Method
1. POI model was adapted from that of Kalff (Kalff, J. C.; Schraut, W. H.; Simmons, R. L.; Bauer, A. J. Surgical manipulation of the gut elicits an intestinal muscularis inflammatory response resulting in postsurgical ileus. Ann. Surg. 1998, 228, 652-663.) as described in Example F above.
2. Rats (male, Sprague-Dawley, 250-300 g, N=6-8/group) were implanted with jugular vein catheters to accommodate dosing of test articles.
3. Rats were fasted overnight and dosed (s.c.) with morphine (3 mg/kg)
4. After 30 minutes, the rats were anesthetized with isoflurane and subjected to abdominal surgery.
5. Following an abdominal incision, the small intestine caecum and large intestine are eviscerated for a period of 15 minutes and kept moist with saline.
6. A "running of the bowel" was performed, a clinically-relevant manipulation of the intestines characterized by first pinching the upper small intestine and continuing this manipulation down through the large intestine.

7. 30 minutes after initial anesthesia, rats were dosed (i.v. bolus) with vehicle or compound 298 (0.03, 0.1, 0.3, 1, 3 mg/kg) immediately after intragastric gavage of $^{99m}$Tc methylcellulose (2%) meal
8. 15 minutes after the meal, the rats were euthanized and the stomach and consecutive 10 cm segments of the intestine are isolated. Radioactivity ($^{99m}$Tc) in each tissue isolate is measured to evaluate gastric emptying and small intestinal transit as previously described.
9. The experimental design for this study is depicted in FIG. 7.

Results and Discussion

The combination of morphine pre-treatment and abdominal surgery causes a significant delay in gastric emptying and small intestinal transit as determined by comparison of the naïve (historic) and vehicle groups. The results indicate that compound 298 (0.1, 0.3, 1, 3 mg/kg) significantly accelerates gastric emptying (FIG. 8) and small intestinal transit (FIG. 9) in this combination disease model of POI and opioid-induced bowel dysfunction. Compound 298 is effective when administered after induction of ileus and concurrent exposure to morphine indicating that compound 298 is not restricted to prophylactic use in this disease model as are alternative treatments such as selective peripheral opioid antagonists.

Compound 298 is effective at restoring GI motility at dose levels as low as 100 µg/kg. This level is consistent with the dose level required to induce GI motility in either POI (100 µg/kg) or OBD (300 µg/kg) alone.

The foregoing is illustrative of the present invention, and is not to be construed as limiting thereof. The invention is defined by the following claims, with equivalents of the claims to be included therein.

What is claimed is:

1. A method of stimulating gastrointestinal motility comprising administering to a subject suffering from at least two disorders caused by gastrointestinal dysmotility an effective amount of a compound having any of the following structures:

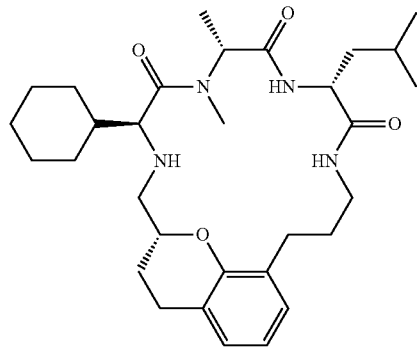

801

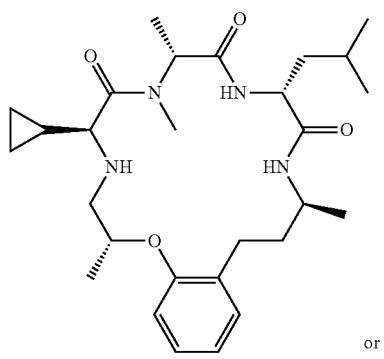

807 or

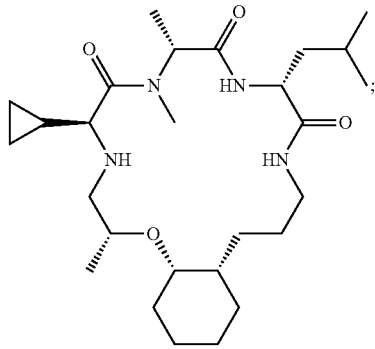

825 or a pharmaceutically acceptable salt thereof.

2. The method of claim 1, wherein the compound is administered orally.
3. The method of claim 1, wherein the compound is administered parenterally.
4. The method of claim 1, wherein the compound is administered intracranially.
5. The method of claim 1, wherein the subject is a mammal.
6. The method of claim 3, wherein the subject is a human.
7. The method of claim 1, wherein the compound is co-administered with an additional agent useful for stimulating gastrointestinal motility.
8. The method of claim 1, wherein the disorders caused by gastrointestinal dysmotility are selected from the group consisting of postoperative ileus, gastroparesis, idiopathic gastroparesis, diabetic gastroparesis and post-surgical gastroparesis, opioid-induced bowel dysfunction, chronic intestinal pseudo-obstruction, short bowel syndrome, emesis, constipation-predominant irritable bowel syndrome (IBS), delayed gastric emptying, gastroesophageal reflux disease (GERD), gastric ulcers, and Crohn's disease.
9. The method of claim 1, wherein one of the disorders is postoperative ileus.
10. The method of claim 1, wherein one of the disorders is diabetic gastroparesis or post-surgical gastroparesis.
11. The method of claim 1, wherein the disorders are postoperative ileus and opioid-induced bowel dysfunction.
12. The method of claim 1, wherein the disorders are post-surgical gastroparesis and opioid-induced bowel dysfunction.
13. The method of claim 1, wherein at least two disorders occur concurrently.
14. The method of claim 1, wherein at least two disorders occur sequentially.
15. The method of claim 1, wherein a dose level of the compound having the structure shown in claim 3 to treat the at least two disorders is an equivalent dose level to that required to treat a single disorder caused by gastrointestinal dysmotility.
16. The method of claim 1, wherein the dose level of the compound having the structure shown in claim 3 is in a range of about 50-150% of a dose level required to treat a single disorder caused by gastrointestinal dysmotility.

* * * * *

UNITED STATES PATENT AND TRADEMARK OFFICE
CERTIFICATE OF CORRECTION

PATENT NO. : 8,088,733 B2
APPLICATION NO. : 11/774185
DATED : January 3, 2012
INVENTOR(S) : Frasier et al.

It is certified that error appears in the above-identified patent and that said Letters Patent is hereby corrected as shown below:

In the Patent:
Column 25, Line 54: Please correct "$NR_rR^s$" to read -- $NR_rR_s$ --

Column 26, Line 5: Please correct "$R^{v'''}$" to read -- $R_v$ --
　　　　　　Line 51: Please correct "$-NR_{pp}SO_2N_{qq}R_{rr}$"
　　　　　　　　　to read -- $NR_{pp}SO_2NR_{qq}R_{rr}$ --

Column 32, Line 38: Please correct "$U_1$ is" to read -- $U_1$ is --
　　　　　　Line 43: Please correct "ITT and/or" to read -- III and/or --

Column 38, Line 2: Please correct "$-(CH_2)_{cc}-CH(CH_3)_2$"
　　　　　　　　　to read -- $-(CH_2)_{cc}CH(CH_3)_2$ --

Column 42, Please correct "following structure" to read -- following structures --

Column 59, Line 66: Please correct "[125I]" to read -- $[^{125}I]$ --

Signed and Sealed this
Tenth Day of April, 2012

David J. Kappos
*Director of the United States Patent and Trademark Office*